(12) United States Patent
Van Quaquebeke et al.

(10) Patent No.: US 7,320,971 B2
(45) Date of Patent: Jan. 22, 2008

(54) 2" OXO-VORUSCHARIN AND DERIVATIVES THEREOF

(75) Inventors: Eric Van Quaquebeke, Woluwe-Saint-Lambert (BE); Jean-Claude Braekman, Rhode-Saint-Genèse (BE); Gentiane Simon, Brussels (BE); Pierre Guissou, Ouagadougou (BF); Odile Germaine Nacoulma, Ouagadougou (BF); Janique Dewelle, Luttre (BE); Francis Darro, Uccle (BE); Robert Kiss, St-Pieters Leeuw (BE)

(73) Assignee: Unibioscreen S.A., Brussels (BE)

( * ) Notice: Subject to any disclaimer, the term of this patent is extended or adjusted under 35 U.S.C. 154(b) by 0 days.

(21) Appl. No.: 10/530,904

(22) PCT Filed: Oct. 9, 2003

(86) PCT No.: PCT/EP03/11194

§ 371 (c)(1),
(2), (4) Date: Dec. 23, 2005

(87) PCT Pub. No.: WO2004/033465

PCT Pub. Date: Apr. 22, 2004

(65) Prior Publication Data

US 2006/0166952 A1   Jul. 27, 2006

Related U.S. Application Data

(60) Provisional application No. 60/420,067, filed on Oct. 21, 2002.

(30) Foreign Application Priority Data

Oct. 9, 2002   (EP)   .................................. 02447192

(51) Int. Cl.
*A61K 31/585* (2006.01)
*C07J 71/00* (2006.01)

(52) U.S. Cl. ......................................... 514/175; 540/61

(58) Field of Classification Search ................. 540/61; 514/175

See application file for complete search history.

(56) References Cited

U.S. PATENT DOCUMENTS 5,645,988 A   7/1997   Vande Woude et al.

OTHER PUBLICATIONS

Desheesh et al., "Glycosidic cardenolides. I. Chemistry of isolation and purification from Calotropis procera plant." Alexandria Science Exchange, vol. 21(3), pp. 221-228, 2000. Abstract only.*
Cheung, et al. "Cardenolide Glycosides of the Asclepiadaceae. New Glycosides from *Asclepias fruticosa* and the Stereochemistry of Uscharin, Voruscharin and Calotoxin," *Journal of the Chemical Society, Perkin Transactions 1: Organic and Bio-Organic Chemistry*, (1972-1999) (1983), (12), pp. 2827-2835.
International Search Report, completed Feb. 23, 2004 and issued to a related foreign application.

* cited by examiner

*Primary Examiner*—Barbara P. Badio
(74) *Attorney, Agent, or Firm*—Knobbe, Martens, Olson & Bear, LLP

(57) ABSTRACT

2" oxo-voruscharin compound and derivatives thereof are disclosed as well as pharmaceutical compositions which include 2" oxo-voruscharin compound or derivatives thereof. The disclosed 2" oxo-voruscharin compound and its derivatives are useful for cancer treatment. Methods of treating cancer using the disclosed compounds are also disclosed.

28 Claims, 13 Drawing Sheets

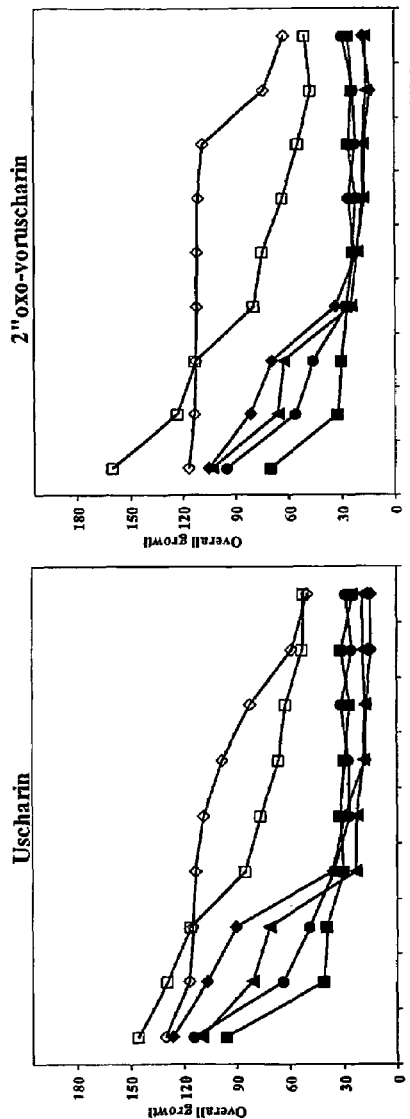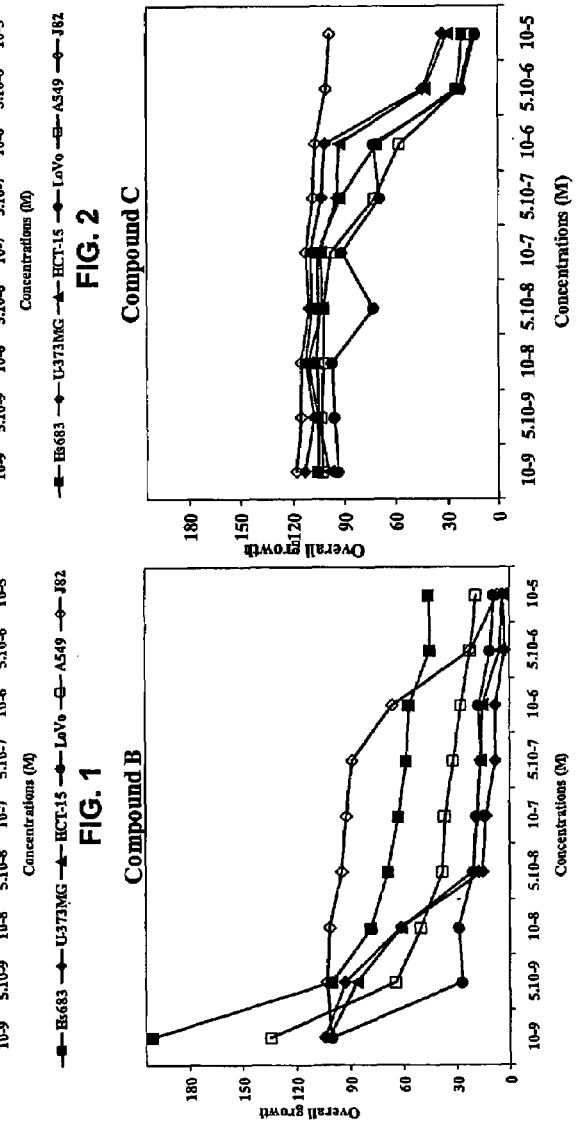

2" OXO-VORUSCHARIN AND DERIVATIVES THEREOF

This application is the U.S. National Phase under 35 U.S.C. § 371 of International Application PCT/EP2003/011194, filed Oct. 9, 2003, which claims priority of U.S. provisional application No. 60/420,067, filed Oct. 21, 2002 and EP 02447192.2, filed Oct. 9, 2002.

FIELD OF THE INVENTION

The present invention relates to novel 2" oxo-voruscharin and derivatives thereof. In addition, the present invention relates to pharmaceutical compositions comprising the novel 2" oxo-voruscharin or derivatives. The present invention further relates to the use of the 2" oxo-voruscharin and derivatives as a medicament and in the preparation of a medicament for treating cancer. The present invention also relates to a method of treating cancer.

BACKGROUND OF THE INVENTION

Plants of the family Asclepiadaceae are known to be extremely poisonous. A well-known representative of the Asclepiadaceae is *Calotropis procera*. Extracts from *Calotropis procera* plants have traditionally been used as an abortifacient, for infanticide, for rheumatic pain and to produce a purgative. The plant is poisonous, but has been used in small amounts for folk remedies for various ailments, and the plant continues to be studied for anti-coagulant and anti-cancer properties. The stems, flowers and leaves of *Calotropis procera* plants are known to contain certain compounds known as cardenolides. Examples of cardenolide glycosides found in *C. procera* include asclepin, voruscharin, uscharin, uscharidin, calotropin, calactin, calotoxin, calotropagenin and uzarigenin. Recently, cytotoxic activity has been attributed to these cardenolide glycosides, and they are exploited in human therapies for treating cardiac insufficiencies.

It has been described that the cardenolide uscharin is particularly useful for medical purposes. Uscharin has been isolated and its chemical structure was determined (structure I).

structure I:

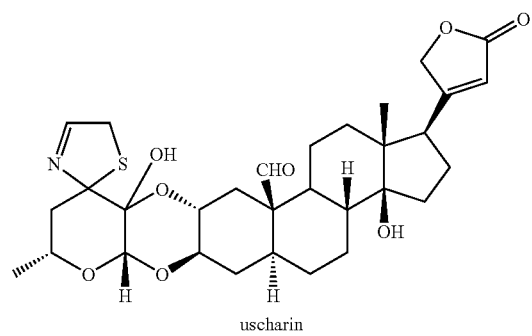

uscharin

Compositions comprising uscharin or salts thereof have been reported to be usable for treatment of medical conditions related to cell proliferation. For example, U.S. Pat. No. 6,342,490 and WO-9852562 both describe compositions comprising uscharin or salts thereof and the use of uscharin to combat cell proliferation, e.g. in the treatment of cancer.

Some of the known cardenolide glycosides, f.e. calotropin and uzarigenin, are cytotoxic for cell cultures but are not mentioned to show in vivo tumor-inhibiting activity. Also uscharin has been shown to have some cytotoxic activity on tumor cells in vitro. In addition, uscharin was also described to have in vivo tumor-inhibiting effects, as for instance described in U.S. Pat. No. 6,342,490. Derivatives of uscharin have not been reported so far to be useful for medical applications.

Cheung et al. (1983; J. Chem. Soc. Perkin Transactions 1: Organic and bio-organic chemistry (1971-1999) (12) 2827-235) disclose the stereochemistry of cardenolide glycosides of Asclepiadaceae including 19-deoxyuscharin, uscharin and voruscharin.

In U.S. Pat. No. 5,645,988 methods of identifying drugs with selective effects against cancer cells are presented. The drug indicated with 650362 shows some similarity with uscharin.

It is a general object of the present invention to provide novel cardenolide glycosides, which have a cytotoxic activity. It is another general object of the present invention to provide novel cardenolide glycosides, which can be exploited in medical applications.

SUMMARY

In a first aspect, the present invention relates to a compound of the formula I or a pharmaceutically acceptable salt thereof, formula I wherein $R^1$ is selected from the group comprising hydrogen, alkyl, alkenyl, alkynyl, alkyloxy, alkyloxyalkyl, alkylthioalkyl, alkyloxycarbonyl, alkylthiocarbonyl, alkanoyl, cycloalkylalkyl, cycloalkylcarbonyl, cycloalkylalkanoyl, cycloalkylthiocarbonyl, cycloalkylalkoxycarbonyl, cycloalkylalkoxythiocarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, arylthiocarbonyl, aralkoxycarbonyl, arylalkylthiocarbonyl, aryloxyalkyl, arylthioalkyl, haloalkyl, hydroxyalkyl, aralkanoyl, aroyl, aryloxycarbonylalkyl, aryloxyalkanoyl, carboxyl, formyl, alkenylcarbonyl, alkynylcarbonyl, $Het^1$, $Het^1$alkyl, $Het^1$oxyalkyl, $Het^1$aryl, $Het^1$aralkyl, $Het^1$cycloalkyl, $Het^1$carbonyl, $Het^1$alkoxycarbonyl, $Het^1$alkylthiocarbonyl, $Het^1$oxycarbonyl, $Het^1$thiocarbonyl, $Het^1$alkanoyl, $Het^1$aralkanoyl, $Het^1$aryloxyalkyl, $Het^1$alkyloxyalkyl, $Het^1$arylthioalkyl, $Het^1$aryloxycarbonyl, $Het^1$aralkoxycarbonyl, $Het^1$aroyl, $Het^1$oxyalkylcarbonyl, $Het^1$alkyloxyalkylcarbonyl, Het¹aryloxyalkylcarbonyl, Het¹carbonyloxyalkyl, Het¹alkylcarbonyloxyalkyl, Het¹aralkylcarbonyloxyalkyl, Het²alkyl; Het²oxyalkyl, Het²alkyloxyalkyl, Het²aralkyl, Het²carbonyl, Het²oxycarbonyl, Het²thiocarbonyl, Het²alkanoyl, Het²alkylthiocarbonyl, Het²alkoxycarbonyl, Het²aralkanoyl, Het²aralkoxycarbonyl, Het²aryloxycarbonyl, Het²aroyl, Het²aryloxyalkyl, Het²arylthioalkyl, Het²oxyalkylcarbonyl, Het²alkyloxyalkylcarbonyl, Het²aryloxyalkylcarbonyl, Het²carbonyloxyalkyl, Het²alkylcarbonyloxyalkyl, Het²aralkylcarbonyloxyalkyl, cyano, aminocarbonyl, aminoalkanoyl, aminoalkyl, $CR^6=NR^7$ or $CR^6=N(OR^7)$, with $R^6$ and $R^7$ being independently selected from the group comprising hydrogen, hydroxyl, alkyl, aryl, Het¹, Het¹alkyl, Het¹aryl, alkenyl, alkynyl, aminoalkyl, aminoaryl, alkylcarbonylamino, arylcarbonylamino, alkylthiocarbonylamino and arylthiocarbonylamino;

wherein $R^2$ and $R^3$ are independently selected from the group comprising hydroxyl, alkyloxy, alkylsilyloxy, arylsilyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, haloalkyloxy, hydroxyalkyloxy, aralkanoyloxy, aroyloxy, aryloxycarbonylalkyloxy, formyloxy, Het¹alkyloxy, Het¹oxy, Het¹oxyalkyloxy, Het¹aryloxy, Het¹aralkyloxy, Het¹cycloalkyloxy, Het¹carbonyloxy, Het¹oxycarbonyloxy, Het¹alkanoyloxy, Het¹aralkanoyloxy, Het¹aryloxyalkyloxy, Het¹aroyl, Het²oxy, Het²alkyloxy; Het²oxyalkyloxy, Het²aralkyloxy, Het²cycloalkyloxy, Het²alkanoyloxy, Het²aralkanoyloxy, Het²carbonyloxyl, Het²aryloxy, Het²aryloxyalkyloxy, wherein $R^1$ $R^2$ and $R^3$ are optionally substituted by one or more substituents independently selected from the group comprising alkyl, aralkyl, aryl, Het¹, Het², cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen or amino optionally mono- or disubstituted wherein the substituents are independently selected from the group comprising alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, aryithioalkoxy, arylthioalkylamino, aralkylthio, aryloxyalkylthio, arylaminoalkylthio, arylthioalkylthio, alkylamino, cycloalkyl, cycloalkylalkyl, Het¹, Het², Het¹alkyl, Het²alkyl, Het¹amino, Het²amino, Het¹alkylamino, Het²alkylamino, Het¹thio, Het²thio, Het¹alkylthio, Het²alkylthio, Het¹oxy and Het²oxy, $OR^8$, $SR^8$, $SO_2NR^8R^9$, $SO_2N(OH)R^8$, CN, $CR^8=NR^9$, $S(O)R^8$, $SO_2R^8$, $CR^8=N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, and $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, $P(O)(OR^8)(OR^9)$, with t being an integer between 1 and 2, and $R^8$ $R^9$ and $R^{10}$ being each independently selected from the group comprising hydrogen, hydroxyl, alkyl, aryl, Het¹, Het¹alkyl, Het¹aryl, alkenyl, alkynyl, aminoalkyl, aminoaryl, alkylcarbonylamino, arylcarbonylamino, alkylthiocarbonylamino and arylthiocarbonylamino;

wherein $R^4$ is selected from the group comprising hydrogen, oxo, is replaced by a double bond between the N atom and the C carbon atom on the N-containing heterocyclic ring of formula I; hydroxyl, alkyl, alkenyl, alkynyl, alkanediyl, alkyloxy, alklylthio, alkylamino, alkyloxyalkyl, arylcarbonylalkyl, alkylcarbonylalkyl, alkanoyl, cycloalkylcarbonylalkyl, cycloalkyl, cycloalkyloxy, cycloalkylthio, cycloalkylamino, cycloalkylalkyl, cycloalkylalkanoyl, aryl, aralkyl, arylalkenyl, arylcarbonyloxy, aryloxycarbonyloxy, aralkoxycarbonyloxy, aryloxyalkyl, haloalkyloxy, haloalkylthio, haloalkylamino, hydroxyalkyl, aralkanoyl, aryloxycarbonylalkyl, aryloxyalkanoyl, Het¹, Het¹alkyl, Het¹oxy, Het¹oxyalkyl, Het¹aryl, Het¹aralkyl, Het¹cycloalkyl, Het¹aryloxyalkyl, Het¹aroyl, Het², Het²oxy, Het²alkyl; Het²oxyalkyl, Het²aralkyl, Het²cycloalkyl, Het²aryl, Het²alkanoyl, Het²aralkanoyl, Het²aroyl, Het²aryloxyalkyl, aminocarbonyl, aminoalkanoyl, aminoalkyl, optionally substituted by one or more substituents independently selected from the group comprising alkyl, aralkyl, aryl, Het¹, Het², cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen or amino optionally mono- or disubstituted wherein the substituents are independently selected from the group comprising alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het¹, Het², Het¹alkyl, Het²alkyl, Het¹amino, Het²amino, Het¹alkylamino, Het²alkylamino, Het¹thio, Het²thio, Het¹alkylthio, Het²alkylthio, Het¹oxy and Het²oxy, $OR^{11}$, $SR^{11}$, $SO_2NR^{11}R^{12}$, $SO_2N(OH)R^{11}$, CN, $CR^{11}=NR^{12}$, $S(O)R^{11}$, $SO_2R^{11}$, $CR^{11}=N(OR^{12})$, $N_3$, $NO_2$, $NR^{11}R^{12}$, $N(OH)R^{11}$, $C(O)R^{11}$, $C(S)R^{11}$, $CO_2R^{11}$, $C(O)SR^{11}$, $C(O)NR^{11}R^{12}$, $C(S)NR^{11}R^{12}$, $C(O)N(OH)R^{12}$, $C(S)N(OH)R^{11}$, $NR^{11}C(O)R^{12}$, $NR^{11}C(S)R^{12}$, $N(OH)C(O)R^{12}$, $N(OH)C(S)R^{11}$, $NR^{11}CO_2R^{12}$, $NR^{11}C(O)NR^{12}R^{13}$, and $NR^{11}C(S)NR^{12}R^{13}$, $N(OH)CO_2R^{11}$, $NR^{11}C(O)SR^{12}$, $N(OH)C(O)NR^{11}R^{12}$, $N(OH)C(S)NR^{11}R^{12}$, $NR^{11}C(O)N(OH)R^{12}$, $NR^{11}C(S)N(OH)R^{12}$, $NR^{11}SO_2R^{12}$, $NHSO_2NR^{11}R^{12}$, $NR^{11}SO_2NHR^{12}$, $P(O)(OR^{11})(OR^{12})$, wherein t is an integer between 1 and 2, $R^{11}$, $R^{12}$ and $R^{13}$ are each independently selected from the group comprising hydrogen, alkyl, alkenyl, and alkynyl; and wherein $R^5$ is selected from the group comprising hydrogen, oxo, hydroxyl, alkyl, alkenyl, alkynyl, alkanediyl, alkyloxy, alkyloxyalkyl, arylcarbonylalkyl, alkylcarbonylalkyl, alkanoyl, cycloalkylcarbonylalkyl, cycloalkyl, cycloalkylalkyl, cycloalkylalkanoyl, aryl, aralkyl, arylalkenyl, arylcarbonyloxy, aryloxycarbonyloxy, aralkoxycarbonyloxy, aryloxyalkyl, haloalkyl, hydroxyalkyl, aralkanoyl, aryloxycarbonylalkyl, aryloxyalkanoyl, Het¹, Het¹alkyl, Het¹oxy, Het¹oxyalkyl, Het¹aryl, Het¹aralkyl, Het¹cycloalkyl, Het¹aryloxyalkyl, Het¹aroyl, Het², Het²oxy, Het²alkyl; Het²oxyalkyl, Het²aralkyl, Het²cycloalkyl, Het²aryl, Het²alkanoyl, Het²aralkanoyl, Het²aroyl, Het²aryloxyalkyl, aminocarbonyl, aminoalkanoyl, aminoalkyl, optionally substituted by one or more substituents independently selected from the group comprising alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen or amino optionally mono- or disubstituted wherein the substituents are independently selected from the group comprising alkyl, aryl, aralkyl, aryloxy, arylamino, arylthio, aryloxyalkyl, arylaminoalkyl, aralkoxy, alkylthio, alkoxy, aryloxyalkoxy, aylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^{11}$, $SR^{11}$, $SO_2NR^{11}R^{12}$, $SO_2N(OH)R^{11}$, CN, $CR^{11}=NR^{12}$, $S(O)R^{11}$, $SO_2R^{11}$, $CR^{11}=N(OR^{12})$, $N_3$, $NO_2$, $NR^{11}R^{12}$, $N(OH)R^{11}$, $C(O)R^{11}$, $C(S)R^{11}$, $CO_2R^{11}$, $C(O)SR^{11}$, $C(O)NR^{11}R^{12}$, $C(S)NR^{11}R^{12}$, $C(O)N(OH)R^{12}$, $C(S)N(OH)R^{11}$, $NR^{11}C(O)R^{12}$, $NR^{11}C(S)R^{12}$, $N(OH)C(O)R^{12}$, $N(OH)C(S)R^{11}$, $NR^{11}CO_2R^{12}$, $NR^{11}C(O)NR^{12}R^{13}$, and $NR^{11}C(S)NR^{12}R^{13}$, $N(OH)CO_2R^{11}$, $NR^{11}C(O)SR^{12}$, $N(OH)C(O)NR^{11}R^{12}$, $N(OH)C(S)NR^{11}R^{12}$, $NR^{11}C(O)N(OH)R^{12}$, $NR^{11}C(S)N(OH)R^{12}$, $NR^{11}SO_2R^{12}$, $NHSO_2NR^{11}R^{12}$, $NR^{11}SO_2NHR^{12}$, $P(O)(OR^{11})(OR^{12})$, wherein t is an integer between 1 and 2, $R^{11}$, $R^{12}$ and $R^{13}$ are each independently selected from the group comprising hydrogen, alkyl, alkenyl, and alkynyl.

In an embodiment, the present invention relates to a compound of the formula I, wherein $R^1$ is selected from the group comprising alkyl, alkenyl, alkynyl, alkyloxy, alkyloxyalkyl, alkylthioalkyl, alkyloxycarbonyl, alkylthiocarbonyl, alkanoyl, cycloalkylalkyl, cycloalkylcarbonyl, cycloalkylalkanoyl, cycloalkylthiocarbonyl, cycloalkylkoxycarbonyl, cycloalkylalkoxy thiocarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, arylthiocarbonyl, aralkoxycarbonyl, arylalkylthiocarbonyl, aryloxyalkyl, arylthioalkyl, haloalkyl, hydroxyalkyl, aralkanoyl, aroyl, aryloxycarbonylalkyl, aryloxyalkanoyl, carboxyl, formyl, alkenylcarbonyl, alkynylcarbonyl, $Het^1$, $Het^1$alkyl, $Het^1$oxyalkyl, $Het^1$aryl, $Het^1$aralkyl, $Het^1$cycloalkyl, $Het^1$carbonyl, $Het^1$alkoxycarbonyl, $Het^1$alkylthiocarbonyl, $Het^1$oxycarbonyl, $Het^1$thiocarbonyl, $Het^1$alkanoyl, $Het^1$aralkanoyl, $Het^1$aryloxyalkyl, $Het^1$alkyloxyalkyl, $Het^1$arylthioalkyl, $Het^1$aryloxycarbonyl, $Het^1$aralkoxycarbonyl, $Het^1$aroyl, $Het^1$oxyalkylcarbonyl, $Het^1$alkyloxyalkylcarbonyl, $Het^1$aryloxyalkylcarbonyl, $Het^1$carbonyloxyalkyl, $Het^1$alkylcarbonyloxyalkyl, $Het^1$aralkylcarbonyloxyalkyl, $Het^2$alkyl; $Het^2$oxyalkyl, $Het^2$alkyloxyalkyl, $Het^2$aralkyl, $Het^2$carbonyl, $Het^2$oxycarbonyl, $Het^2$thiocarbonyl, $Het^2$alkanoyl, $Het^2$alkylthiocarbonyl, $Het^2$alkoxycarbonyl, $Het^2$aralkanoyl, $Het^2$aralkoxycarbonyl, $Het^2$aryloxycarbonyl, $Het^2$aroyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $Het^2$carbonyloxyalkyl, $Het^2$alkylcarbonyloxyalkyl, $Het^2$aralkylcarbonyloxyalkyl, cyano, aminocarbonyl, aminoalkanoyl, aminoalkyl, $CR^6=NR^7$ or $CR^6=N(OR^7)$ with $R^6$ and $R^7$ being independently selected from the group comprising hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkylthiocarbonylamino and arylthiocarbonylamino;

wherein $R^2$ and $R^3$ are independently selected from the group comprising hydroxyl, alkyloxy, alkylsilyloxy, arylsilyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, haloalkyloxy, hydroxyalkyloxy, aralkanoyloxy, aroyloxy, aryloxycarbonylalkyloxy, formyloxy, $Het^1$alkyloxy, $Het^1$oxy, $Het^1$oxyalkyloxy, $Het^1$aryloxy, $Het^1$aralkyloxy, $Het^1$cycloalkyloxy, $Het^1$carbonyloxy, $Het^1$oxycarbonyloxy, $Het^1$alkanoyloxy, $Het^1$aralkanoyloxy, $Het^1$aryloxyalkyloxy, $Het^1$aroyl, $Het^2$oxy, $Het^2$alkyloxy; $Het^2$oxyalkyloxy, $Het^2$aralkyloxy, $Het^2$cycloalkyloxy, $Het^2$alkanoyloxy, $Het^2$aralkanoyloxy, $Het^2$carbonyloxyl, $Het^2$aryloxy, $Het^2$aryloxyalkyloxy, wherein $R^1$ $R^2$ and $R^3$ are optionally substituted by one or more substituents independently selected from the group comprising alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen or amino optionally mono- or disubstituted wherein the substituents are independently selected from the group comprising alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, CN, $CR^8=NR^9$, $S(O)R^8$, $SO_2R^8$, $CR^8=N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, and $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, $P(O)(OR^8)(OR^9)$, with t being an integer between 1 and 2, and $R^8$ $R^9$ and $R^{10}$ being each independently selected from the group comprising hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkylthiocarbonylamino and arylthiocarbonylamino;

and wherein $R^4$ is oxo and $R^5$ is hydrogen or alkyl.

In particular, the invention relates to a compound having the above-described formula I, wherein $R^1$ is formyl (—CHO); wherein $R^2$ and $R^3$ are hydroxyl; wherein $R^4$ is oxo; and wherein and $R^5$ is hydrogen. This particular compound is referred to as 2" oxo-voruscharin. Thus, the present invention provides novel 2" oxo-voruscharin and Its derivatives. Importantly, these compounds show in vitro as well as in vivo cytotoxic anti-tumor effects and are consequently very suitable for use in all kind of therapeutic applications as described below.

In addition, the present invention relates to pharmaceutical compositions comprising the above-described compounds. Furthermore, the present Invention relates to the use of said compounds as a medicament for the treatment of diseases associated with cell proliferation, in particular for treatment of cancer. The present invention further relates to the use of the above-described compounds in the preparation of a medicament for the treatment of cancer, and a method of treating cancer.

DETAILED DESCRIPTION OF THE FIGURES

FIG. 1 represents the anti-tumor activity of the compound uscharin on six human cancer cell lines.

FIG. 2 to 8 represent the anti-tumor activity of the different compounds according to the invention on six human cancer cell lines. FIG. 2 represents the activity of 2″ oxo-voruscharin. FIGS. 3, 4, 5, 6, 7 and 8 respectively represent the activity of compounds B, C, D, E, H and I.

FIG. 9 compares the cytotoxic activity of uscharin and 2″oxo-voruscharin on six human cancer cell lines.

FIG. 10 compares the cytotoxic activity of uscharin, 2″oxo-voruscharin and compounds B, C, D, E, H and I on six human cancer cell lines.

Figure 17:
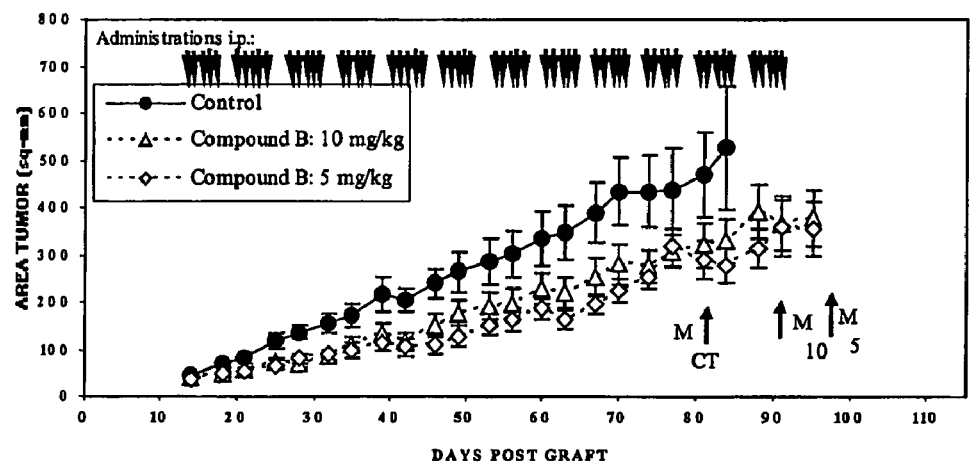
Figure 18:
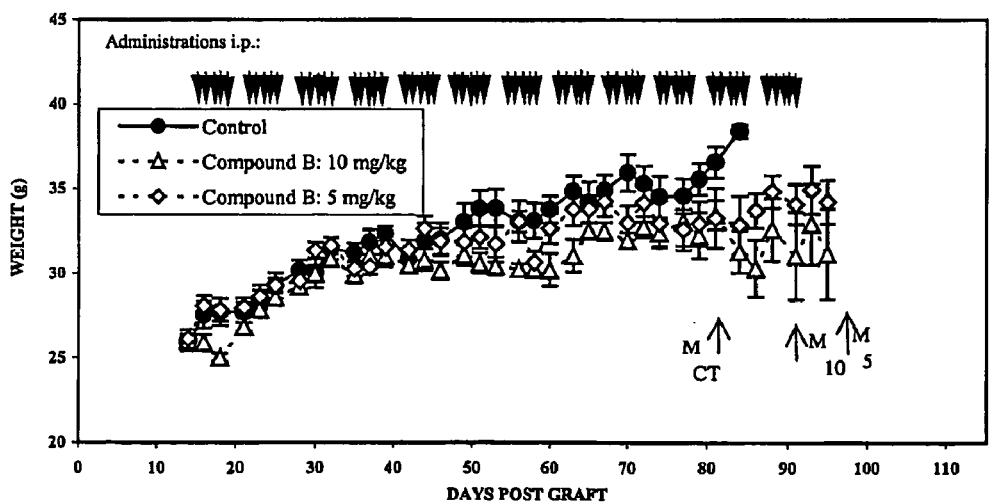
Figure 19:
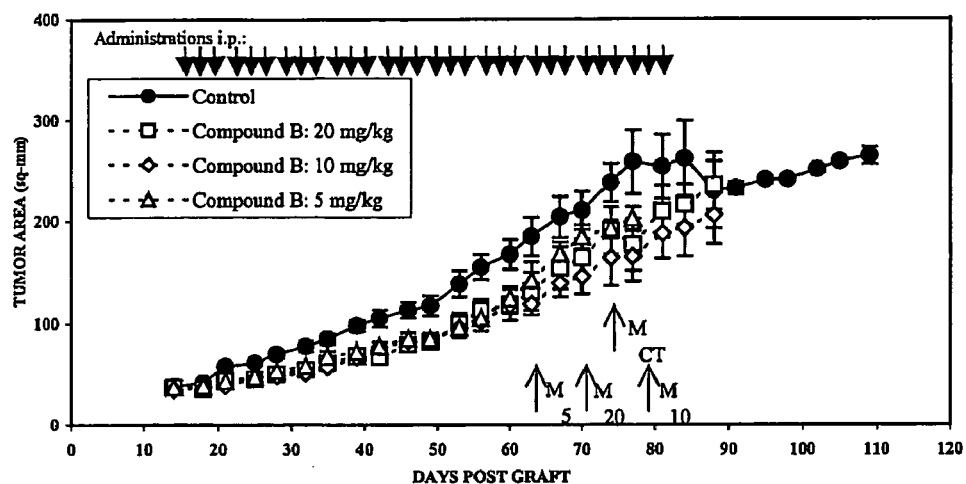
Figure 20:
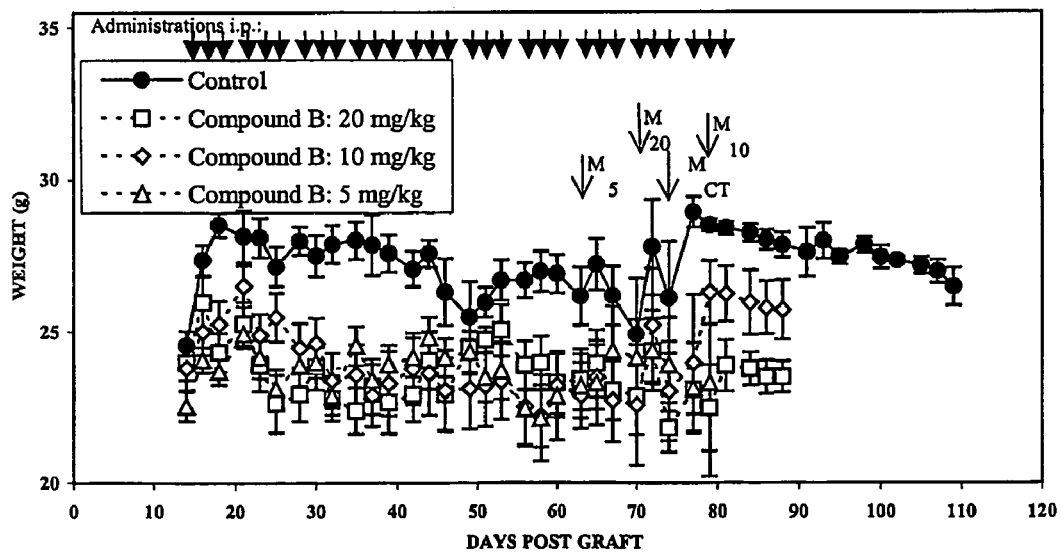
Figure 21:
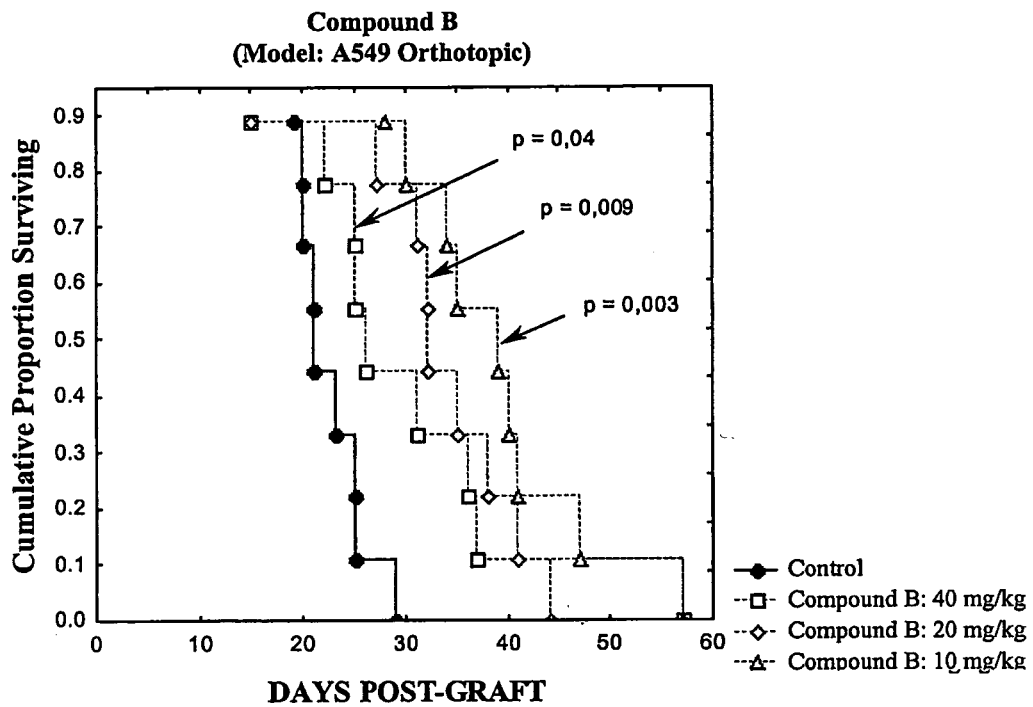
Figure 22:
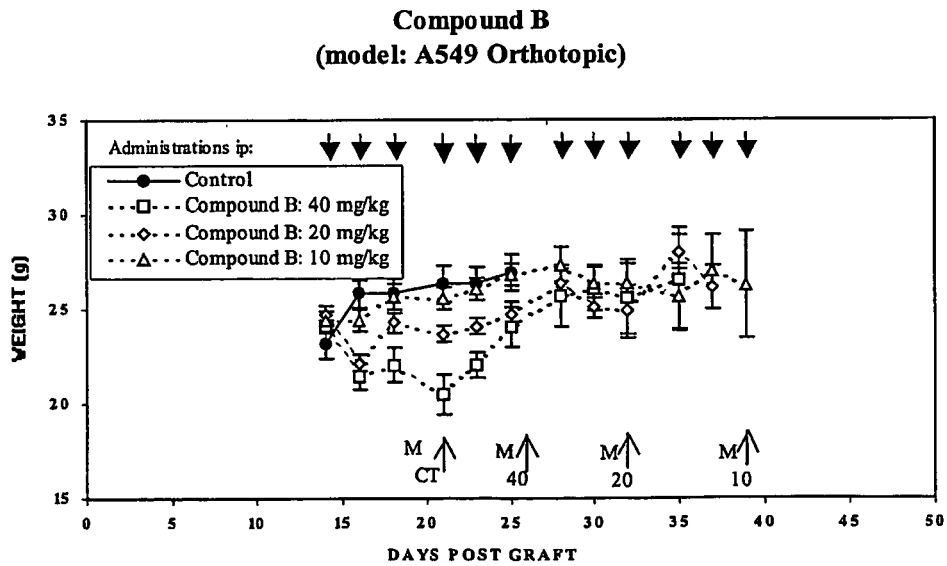

FIGS. 17 to 22 represent the anti-tumor effects of compound B on different models of tumor bearing mice. FIG. 17 represents the effect of compound B at different concentrations on the tumor size of MCF-7-TD5-tumor bearing mice. FIG. 18 represents the effect of compound B on the weight of mice bearing MCF-7-TD5 tumors. FIG. 19 represents the effect of compound B at different concentrations on the tumor size of C32-tumor bearing mice. FIG. 20 represents the effect of compound B on the weight of mice bearing C32 tumors. FIG. 21 represents the death rate of mice bearing A549 tumors after treatment with compound B. FIG. 22 represents the effect of compound B on the weight of mice bearing A549 tumors.

DETAILED DESCRIPTION

In a first embodiment, the present invention provides for a compound of the formula I or a pharmaceutically acceptable salt or ester thereof, formula I

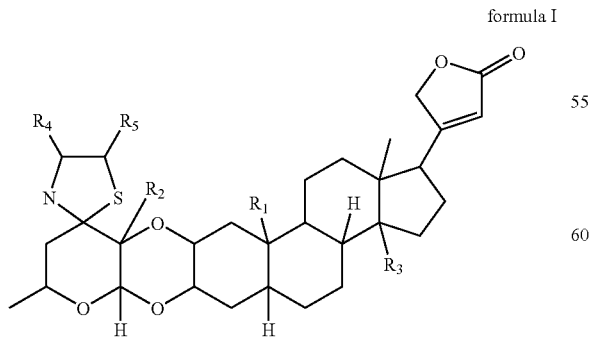

wherein $R^1$ is selected from the group comprising hydrogen, alkyl, alkenyl, alkynyl, alkyloxy, alkyloxyalkyl, alkylthioalkyl, alkyloxycarbonyl, alkylthiocarbonyl, alkanoyl, cycloalkylalkyl, cycloalkylcarbonyl, cycloalkylalkanoyl, cycloalkylthiocarbonyl, cycloalkylalkoxycarbonyl, cycloalkylalkoxythiocarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, arylthiocarbonyl, aralkoxycarbonyl, arylalkylthiocarbonyl, aryloxyalkyl, arylthioalkyl, haloalkyl, hydroxyalkyl, aralkanoyl, aroyl, aryloxycarbonylalkyl, aryloxyalkanoyl, carboxyl, formyl, alkenylcarbonyl, alkynylcarbonyl, $Het^1$, $Het^1$alkyl, $Het^1$oxyalkyl, $Het^1$aryl, $Het^1$aralkyl, $Het^1$cycloalkyl, $Het^1$carbonyl, $Het^1$alkoxycarbonyl, $Het^1$alkylthiocarbonyl, $Het^1$oxycarbonyl, $Het^1$thiocarbonyl, $Het^1$alkanoyl, $Het^1$aralkanoyl, $Het^1$aryloxyalkyl, $Het^1$alkyloxyalkyl, $Het^1$arylthioalkyl, $Het^1$aryloxycarbonyl, $Het^1$aralkoxycarbonyl, $Het^1$aroyl, $Het^1$oxyalkylcarbonyl, $Het^1$alkyloxyalkylcarbonyl, $Het^1$aryloxyalkylcarbonyl, $Het^1$carbonyloxyalkyl, $Het^1$alkylcarbonyloxyalkyl, $Het^1$aralkylcarbonyloxyalkyl, $Het^2$alkyl; $Het^2$oxyalkyl, $Het^2$alkyloxyalkyl, $Het^2$aralkyl, $Het^2$carbonyl, $Het^2$oxycarbonyl, $Het^2$thiocarbonyl, $Het^2$alkanoyl, $Het^1$alkylthiocarbonyl, $Het^2$alkoxycarbonyl, $Het^2$aralkanoyl, $Het^2$aralkoxycarbonyl, $Het^2$aryloxycarbonyl, $Het^2$aroyl, $Het^2$aryloxyalkyl, $Het^2$arylthioalkyl, $Hat^2$oxyalkylcarbonyl, $Het^2$alkyloxyalkylcarbonyl, $Het^2$aryloxyalkylcarbonyl, $Het^2$carbonyloxyalkyl, $Het^2$alkylcarbonyloxyalkyl, $Het^2$aralkylcarbonyloxyalkyl, cyano, aminocarbonyl, aminoalkanoyl, aminoalkyl, $CR^6=NR^7$ or $CR^6=N(OR^7)$, with $R^6$ and $R^7$ being independently selected from the group comprising hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkylthiocarbonylamino and arylthiocarbonylamino;

wherein $R^2$ and $R^3$ are independently selected from the group comprising hydroxyl, alkyloxy, alkylsilyloxy, arylsilyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, haloalkyloxy, hydroxyalkyloxy, aralkanoyloxy, aroyloxy, aryloxycarbonylalkyloxy, formyloxy, $Het^1$alkyloxy, $Het^1$oxy, $Het^1$oxyalkyloxy, $Het^1$aryloxy, $Het^1$aralkyloxy, $Het^1$cycloalkyloxy, $Het^1$carbonyloxy, $Het^1$oxycarbonyloxy, $Het^1$alkanoyloxy, $Het^1$aralkanoyloxy, $Het^1$aryloxyalkyloxy, $Het^1$aroyl, $Het^2$oxy, $Het^2$alkyloxy; $Het^2$oxyalkyloxy, $Het^2$aralkyloxy, $Het^2$cycloalkyloxy, $Het^2$alkanoyloxy, $Het^2$aralkanoyloxy, $Het^2$carbonyloxyl, $Het^2$aryloxy, $Het^2$aryloxyalkyloxy, wherein $R^1$ $R^2$ and $R^3$ are optionally substituted by one or more substituents independently selected from the group comprising alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen or amino optionally mono- or disubstituted wherein the substituents are independently selected from the group comprising alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het$^1$, Het$^2$, Het$^1$alkyl, Het$^2$alkyl, Het$^1$amino, Het$^2$amino, Het$^1$alkylamino, Het$^2$alkylamino, Het$^1$thio, Het$^2$thio, Het$^1$alkylthio, Het$^2$alkylthio, Het$^1$oxy and Het$^2$oxy, OR$^8$, SR$^8$, SO$_2$NR$^8$R$^9$, SO$_2$N(OH)R$^8$, CN, CR$^8$=NR$^9$, S(O)R$^8$, SO$_2$R$^8$, CR$^8$=N(OR$^9$), N$_3$, NO$_2$, NR$^8$R$^9$, N(OH)R$^8$, C(O)R$^8$, C(S)R$^8$, CO$_2$R$^8$, C(O)SR$^8$, C(O)NR$^8$R$^9$, C(S)NR$^8$R$^9$, C(O)N(OH)R$^9$, C(S)N(OH)R$^8$, NR$^8$C(O)R$^9$, NR$^8$C(S)R$^9$, N(OH)C(O)R$^9$, N(OH)C(S)R$^8$, NR$^8$CO$_2$R$^9$, NR$^8$C(O)NR$^9$R$^{10}$, and NR$^8$C(S)NR$^9$R$^{10}$, N(OH)CO$_2$R$^8$, NR$^8$C(O)SR$^9$, N(OH)C(O)NR$^8$R$^9$, N(OH)C(S)NR$^8$R$^9$, NR$^8$C(O)N(OH)R$^9$, NR$^8$C(S)N(OH)R$^9$, NR$^8$SO$_2$R$^9$, NHSO$_2$NR$^8$R$^9$, NR$^8$SO$_2$NHR$^9$, P(O)(OR$^8$)(OR$^9$), with t being an integer between 1 and 2, and R$^8$ R$^9$ and R$^{10}$ being each independently selected from the group comprising hydrogen, hydroxyl, alkyl, aryl, Het$^1$, Het$^1$alkyl, Het$^1$aryl, alkenyl, alkynyl, aminoalkyl, aminoaryl, alkylcarbonylamino, arylcarbonylamino, alkylthiocarbonylamino and arylthiocarbonylamino;

wherein R$^4$ is selected from the group comprising hydrogen, oxo, is replaced by a double bond between the N atom and the C carbon atom on the N-containing heterocyclic ring of formula I; hydroxyl, alkyl, alkenyl, alkynyl, alkanediyl, alkyloxy, alklylthio, alkylamino, alkyloxyalkyl, arylcarbonylalkyl, alkylcarbonylalkyl, alkanoyl, cycloalkylcarbonylalkyl, cycloalkyl, cycloalkyloxy, cycloalkylthio, cycloalkylamino, cycloalkylalkyl, cycloalkylalkanoyl, aryl, aralkyl, arylalkenyl, arylcarbonyloxy, aryloxycarbonyloxy, aralkoxycarbonyloxy, aryloxyalkyl, haloalkyloxy, haloalkylthio, haloalkylamino, hydroxyalkyl, aralkanoyl, aryloxycarbonylalkyl, aryloxyalkanoyl, Het$^1$, Het$^1$alkyl, Het$^1$oxy, Het$^1$oxyalkyl, Het$^1$aryl, Het$^1$aralkyl, Het$^1$cycloalkyl, Het$^1$aryloxyalkyl, Het$^1$aroyl, Het$^2$, Het$^2$oxy, Het$^2$alkyl, Het$^2$oxyalkyl, Het$^2$aralkyl, Het$^2$cycloalkyl, Het$^2$aryl, Het$^2$alkanoyl, Het$^2$aralkanoyl, Het$^2$aroyl, Het$^2$aryloxyalkyl, aminocarbonyl, aminoalkanoyl, aminoalkyl, optionally substituted by one or more substituents independently selected from the group comprising alkyl, aralkyl, aryl, Het$^1$, Het$^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen or amino optionally mono- or disubstituted wherein the substituents are independently selected from the group comprising alkyl, aryl, aralkyl, aryloxy, arylamino, arylthio, aryloxyalkyl, arylaminoalkyl, aralkoxy, alkylthio, alkoxy, aryloxyalkoxy, aylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het$^1$, Het$^2$, Het$^1$alkyl, Het$^2$alkyl, Het$^1$amino, Het$^2$amino, Het$^1$alkylamino, Het$^2$alkylamino, Het$^1$thio, Het$^2$thio, Het$^1$alkylthio, Het$^2$alkylthio, Het$^1$oxy and Het$^2$oxy, OR$^{11}$, SR$^{11}$, SO$_2$NR$^{11}$R$^{12}$, SO$_2$N(OH)R$^{11}$, CN, CR$^{11}$=NR$^{12}$, S(O)R$^{11}$, SO$_2$R$^{11}$, CR$^{11}$=N(OR$^{12}$), N$_3$, NO$_2$, NR$^{11}$R$^{12}$, N(OH)R$^{11}$, C(O)R$^{11}$, C(S)R$^{11}$, CO$_2$R$^{11}$, C(O)SR$^{11}$, C(O)NR$^{11}$R$^{12}$, C(S)NR$^{11}$R$^{12}$, C(O)N(OH)R$^{12}$, C(S)N(OH)R$^{11}$, NR$^{11}$C(O)R$^{12}$, NR$^{11}$C(S)R$^{12}$, N(OH)C(O)R$^{12}$, N(OH)C(S)R$^{11}$, NR$^{11}$CO$_2$R$^{12}$, NR$^{11}$C(O)NR$^{12}$R$^{13}$, and NR$^{11}$C(S)NR$^{12}$R$^{13}$, N(OH)CO$_2$R$^{11}$, NR$^{11}$C(O)SR$^{12}$, N(OH)C(O)NR$^{11}$R$^{12}$, N(OH)C(S)NR$^{11}$R$^{12}$, NR$^{11}$C(O)N(OH)R$^{12}$, NR$^{11}$C(S)N(OH)R$^{12}$, NR$^{11}$SO$_2$R$^{12}$, NHSO$_2$NR$^{11}$R$^{12}$, NR$^{11}$SO$_2$NHR$^{12}$, P(O)(OR$^{11}$)(OR$^{12}$), wherein t is an integer between 1 and 2, R$^{11}$, R$^{12}$ and R$^{13}$ are each independently selected from the group comprising hydrogen, alkyl, alkenyl, and alkynyl; and wherein R$^5$ is selected from the group comprising hydrogen, oxo, hydroxyl, alkyl, alkenyl, alkynyl, alkanediyl, alkyloxy, alkyloxyalkyl, arylcarbonylalkyl, alkylcarbonylalkyl, alkanoyl, cycloalkylcarbonylalkyl, cycloalkyl, cycloalkylalkyl, cycloalkylalkanoyl, aryl, aralkyl, arylalkenyl, arylcarbonyloxy, aryloxycarbonyloxy, aralkoxycarbonyloxy, aryloxyalkyl, haloalkyl, hydroxyalkyl, aralkanoyl, aryloxycarbonylalkyl, aryloxyalkanoyl, Het$^1$, Het$^1$alkyl, Het$^1$oxy, Het$^1$oxyalkyl, Het$^1$aryl, Het$^1$aralkyl, Het$^1$cycloalkyl, Het$^1$aryloxyalkyl, Het$^1$aroyl, Het$^2$, Het$^2$oxy, Het$^2$alkyl, Het$^2$oxyalkyl, Het$^2$aralkyl, Het$^2$cycloalkyl, Het$^2$aryl, Het$^2$alkanoyl, Het$^2$aralkanoyl, Het$^2$aroyl, Het$^2$aryloxyalkyl, aminocarbonyl, aminoalkanoyl, aminoalkyl, optionally substituted by one or more substituents independently selected from the group comprising alkyl, aralkyl, aryl, Het$^1$, Het$^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen or amino optionally mono- or disubstituted wherein the substituents are independently selected from the group comprising alkyl, aryl, aralkyl, aryloxy, arylamino, arylthio, aryloxyalkyl, arylaminoalkyl, aralkoxy, alkylthio, alkoxy, aryloxyalkoxy, aylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het$^1$, Het$^2$, Het$^1$alkyl, Het$^2$alkyl, Het$^1$amino, Het$^2$amino, Het$^1$alkylamino, Het$^2$alkylamino, Het$^1$thio, Het$^2$thio, Het$^1$alkylthio, Het$^2$alkylthio, Het$^1$oxy and Het$^2$oxy, OR$^{11}$, SR$^{11}$, SO$_2$NR$^{11}$R$^{12}$, SO$_2$N(OH)R$^{11}$, CN, CR$^{11}$=NR$^{12}$, S(O)R$^{11}$, SO$_2$R$^{11}$, CR$^{11}$=N(OR$^{12}$), N$_3$, NO$_2$, NR$^{11}$R$^{12}$, N(OH)R$^{11}$, C(O)R$^{11}$, C(S)R$^{11}$, CO$_2$R$^{11}$, C(O)SR$^{11}$, C(O)NR$^{11}$R$^{12}$, C(S)NR$^{11}$R$^{12}$, C(O)N(OH)R$^{12}$, C(S)N(OH)R$^{11}$, NR$^{11}$C(O)R$^{12}$, NR$^{11}$C(S)R$^{12}$, N(OH)C(O)R$^{12}$, N(OH)C(S)R$^{11}$, NR$^{11}$CO$_2$R$^{12}$, NR$^{11}$C(O)NR$^{12}$R$^{13}$, and NR$^{11}$C(S)NR$^{12}$R$^{13}$, N(OH)CO$_2$R$^{11}$, NR$^{11}$C(O)SR$^{12}$, N(OH)C(O)NR$^{11}$R$^{12}$, N(OH)C(S)NR$^{11}$R$^{12}$, NR$^{11}$C(O)N(OH)R$^{12}$, NR$^{11}$C(S)N(OH)R$^{12}$, NR$^{11}$SO$_2$R$^{12}$, NHSO$_2$NR$^{11}$R$^{12}$, NR$^{11}$SO$_2$NHR$^{12}$, P(O)(OR$^{11}$)(OR$^{12}$), wherein t is an integer between 1 and 2, R$^{11}$, R$^{12}$ and R$^{13}$ are each independently selected from the group comprising hydrogen, alkyl, alkenyl, and alkynyl.

In another embodiment, the present invention relates to a compound of the formula I, wherein R$^1$ is selected from the group comprising alkyl, alkenyl, alkynyl, alkyloxy, alkyloxyalkyl, alkylthioalkyl, alkyloxycarbonyl, alkylthiocarbonyl, alkanoyl, cycloalkylalkyl, cycloalkylcarbonyl, cycloalkylalkanoyl, cycloalkylthiocarbonyl, cycloalkylalkoxycarbonyl, cycloalkylalkoxythiocarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, arylthiocarbonyl, aralkoxycarbonyl, arylalkylthiocarbonyl, aryloxyalkyl, arylthioalkyl, haloalkyl, hydroxyalkyl, aralkanoyl, aroyl, aryloxycarbonylalkyl, aryloxyalkanoyl, carboxyl, formyl, alkenylcarbonyl, alkynylcarbonyl, Het$^1$, Het$^1$alkyl, Het$^1$oxyalkyl, Het$^1$aryl, Het$^1$aralkyl, Het$^1$cycloalkyl, Het¹carbonyl, Het¹alkoxycarbonyl, Het¹alkylthiocarbonyl, Het¹oxycarbonyl, Het¹thiocarbonyl, Het¹alkanoyl, Het¹aralkanoyl, Het¹aryloxyalkyl, Het¹alkyloxyalkyl, Het¹arylthioalkyl, Het¹aryloxycarbonyl, Het¹aralkoxycarbonyl, Het¹aroyl, Het¹oxyalkylcarbonyl, Het¹alkyloxyalkylcarbonyl, Het¹aryloxyalkylcarbonyl, Het¹carbonyloxyalkyl, Het¹alkylcarbonyloxyalkyl, Het¹aralkylcarbonyloxyalkyl, Het¹alkyl; Het²oxyalkyl, Het²alkyloxyalkyl, Het²aralkyl, Het²carbonyl, Het²oxycarbonyl, Het²thiocarbonyl, Het²alkanoyl, Het²alkylthiocarbonyl, Het²alkoxycarbonyl, Het²aralkanoyl, Het²aralkoxycarbonyl, Het²aryloxycarbonyl, Het²aroyl, Het²aryloxyalkyl, Het²arylthioalkyl, Het²oxyalkylcarbonyl, Het²alkyloxyalkylcarbonyl, Het²aryloxyalkylcarbonyl, Het²carbonyloxyalkyl, Het²alkylcarbonyloxyalkyl, Het²aralkylcarbonyloxyalkyl, cyano, aminocarbonyl, aminoalkanoyl, aminoalkyl, $CR^6=NR^7$ or $CR^6=N(OR^7)$ with $R^6$ and $R^7$ being independently selected from the group comprising hydrogen, hydroxyl, alkyl, aryl, Het¹, Het¹alkyl, Het¹aryl, alkenyl, alkynyl, aminoalkyl, aminoaryl, alkylcarbonylamino, arylcarbonylamino, alkylthiocarbonylamino and arylthiocarbonylamino;

wherein $R^2$ and $R^3$ are independently selected from the group comprising hydroxyl, alkyloxy, alkylsilyloxy, arylsilyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, haloalkyloxy, hydroxyalkyloxy, aralkanoyloxy, aroyloxy, aryloxycarbonylalkyloxy, formyloxy, Het¹alkyloxy, Het¹oxy, Het¹oxyalkyloxy, Het¹aryloxy, Het¹aralkyloxy, Het¹cycloalkyloxy, Het¹carbonyloxy, Het¹oxycarbonyloxy, Het¹alkanoyloxy, Het¹aralkanoyloxy, Het¹aryloxyalkyloxy, Het¹aroyl, Het²oxy, Het²alkyloxy; Het²oxyalkyloxy, Het²aralkyloxy, Het²cycloalkyloxy, Het²alkanoyloxy, Het²aralkanoyloxy, Het²carbonyloxyl, Het²aryloxy, Het²aryloxyalkyloxy, wherein $R^1$ $R^2$ and $R^3$ are optionally substituted by one or more substituents independently selected from the group comprising alkyl, aralkyl, aryl, Het¹, Het², cycloalkyl, alkyloxycarbonyl, carboxyl, aminocarbonyl, mono- or di(alkyl)aminocarbonyl, aminosulfonyl, $alkylS(=O)_t$, hydroxy, cyano, halogen or amino optionally mono- or disubstituted wherein the substituents are independently selected from the group comprising alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het¹, Het², Het¹alkyl, Het²alkyl, Het¹amino, Het²amino, Het¹alkylamino, Het²alkylamino, Het¹thio, Het²thio, Het¹alkylthio, Het²alkylthio, Het¹oxy and Het²oxy, $OR^8$, $SR^8$, $SO_2NR^8R^9$, $SO_2N(OH)R^8$, $CN$, $CR^8=NR^9$, $S(O)R^8$, $SO_2R^8$, $CR^8=N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, and $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, $P(O)(OR^8)(OR^9)$, with t being an integer between 1 and 2, and $R^8$ $R^9$ and $R^{10}$ being each independently selected from the group comprising hydrogen, hydroxyl, alkyl, aryl, Het¹, Het¹alkyl, Het¹aryl, alkenyl, alkynyl, aminoalkyl, aminoaryl, alkylcarbonylamino, arylcarbonylamino, alkylthiocarbonylamino and arylthiocarbonylamino;

and wherein $R^4$ is oxo and $R^6$ is hydrogen or alkyl.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "alkyl", alone or in combination, means straight and branched chained saturated hydrocarbon radicals containing from 1 to 10 carbon atoms, preferably from 1 to 8 carbon atoms, more preferably 1 to 6 carbon atoms. Examples of such radicals include methyl, ethyl, n-propyl, isopropyl, n-butyl, isobutyl, sec-butyl, tert-butyl, 2-methylbutyl, pentyl, iso-amyl, hexyl, 3-methylpentyl, octyl and the like.

The term "alkenyl", alone or in combination, defines straight and branched chained hydrocarbon radicals containing from 2 to about 18 carbon atoms, preferably from 2 to 8 carbon atoms, more preferably 2-6 carbon atoms containing at least one double bond such as, for example, ethenyl, propenyl, butenyl, pentenyl, hexenyl and the like.

The term "alkynyl", alone or in combination, defines straight and branched chained hydrocarbon radicals having from 2 to 10 carbon atoms containing at least one triple bond, more preferably from 2 to about 6 carbon atoms. Examples of alkynyl radicals include ethynyl, propynyl, (propargyl), butynyl, pentynyl, hexynyl and the like.

The term "cycloalkyl" alone or in combination, means a saturated or partially saturated monocyclic, bicyclic or polycyclic alkyl radical wherein each cyclic moiety contains from about 3 to about 8 carbon atoms, more preferably from about 3 to about 7 carbon atoms. Examples of monocyclic cycloalkyl radicals include cyclopropyl, cyclobutyl, cyclopentyl, cyclohexyl, cycloheptyl, cyclooctyl and the like. Examples of polycyclic cycloalkyl radicals include decahydronaphthyl, bicyclo [5.4.0] undecyl, adamantyl, and the like.

The term "cycloalkylalkyl" means an alkyl radical as defined herein, in which at least one hydrogen atom on the alkyl radical is replaced by a cycloalkyl radical as defined herein. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "aryl" alone or in combination, is meant to include phenyl and naphtyl which both may be optionally substituted with one or more substituents independently selected from alkyl, alkoxy, halogen, hydroxy, amino, nitro, cyano, haloalkyl, carboxy, alkoxycarbonyl, cycloalkyl, Het¹, amido, optionally mono- or disubstituted aminocarbonyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, haloC$_{1-6}$alkyl, carboxyl, C$_{1-6}$alkoxycarbonyl, C$_{3-7}$cycloalkyl, Het$^1$, optionally mono- or disubstituted aminocarbonyl, methylthio and methylsulfonyl; whereby the optional substituents on any amino function are independently selected from alkyl, alkyloxy, Het$^1$, Het$^1$alkyl, Het$^1$alkyl, Het$^1$oxy, Het$^1$oxyalkyl, phenyl, phenyloxy, phenyloxyalkyl, phenylalkyl, alkyloxycarbonylamino, amino, and aminoalkyl whereby each of the amino groups may optionally be mono- or where possible di-substituted with alkyl. Examples of aryl includes phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4dimethyl-3-aminophenyl, 4-hydroxyphenyl, 3-methyl-4hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl and the like.

The term "aralkyl" alone or in combination, means an alkyl as defined herein, wherein an alkyl hydrogen atom is replaced by an aryl as defined herein. Examples of aralkyl radicals include benzyl, phenethyl, dibenzylmethyl, methylphenylmethyl, 3-(2-naphthyl)-butyl, and the like.

As used herein, the term "oxo" or "=O" forms a carbonyl moiety with the carbon atom to which it is attached. The term "formyl" or "—CHO" is an aldehyde moiety whereby the C atom binds to the carbon atom to which it is attached. As used herein, the term "formyloxy" or "—OCHO" forms a formic ester moiety whereby the oxygen atom binds to the carbon atom to which it is attached. As used herein, the term "carboxyl" or "—COOH" is an acid moiety whereby the carbon atom binds to the carbon atom to which it is attached.

The term "haloalkyl" alone or in combination, means an alkyl radical having the meaning as defined above wherein one or more hydrogens are replaced with a halogen, preferably, chloro or fluoro atoms, more preferably fluoro atoms. Examples of such haloalkyl radicals include chloromethyl, 1-bromoethyl, fluoromethyl, difluoromethyl, trifluoromethyl, 1,1,1-trifluoroethyl and the like.

The term "Het$^1$" alone or in combination, is defined as a saturated or partially unsaturated monocyclic, bicyclic or polycyclic heterocycle having preferably 3 to 12 ring members, more preferably 5 to 10 ring members and more preferably 5 to 6 ring members, which contains one or more heteroatom ring members selected from nitrogen, oxygen or sulfur and which is optionally substituted on one or more carbon atoms by alkyl, alkyloxy, halogen, hydroxy, oxo, optionally mono- or disubstituted amino, nitro, cyano, haloalkyl, carboxyl, alkoxycarbonyl, cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are independently selected from alkyl, alkyloxy, Het$^2$, Het$^2$alkyl, Het$^2$oxy, Het$^2$oxyalkyl, aryl, aryloxy, aryloxyalkyl, aralkyl, alkyloxycarbonylamino, amino, and aminoalkyl whereby each of the amino groups may optionally be mono- or where possible di-substituted with alkyl.

The term "Het$^2$" as a group or part of a group is defined as an aromatic monocyclic, bicyclic or tricyclic heterocycle having preferably 3 to 12 ring members, more preferably 5 to 10 ring members and more preferably 5 to 6 ring members, which contains one or more heteroatom ring members selected from nitrogen, oxygen or sulfur and which is optionally substituted on one or more carbon atoms by alkyl, alkyloxy, halogen, hydroxy, optionally mono- or disubstituted amino, nitro, cyano, haloalkyl, carboxyl, alkoxycarbonyl, cycloalkyl, optionally mono- or disubstituted aminocarbonyl, methylthio, methylsulfonyl, aryl, Het$^1$ and an aromatic monocyclic, bicyclic or tricyclic heterocycle having 3 to 12 ring members; whereby the optional substituents on any amino function are independently selected from alkyl, alkyloxy, Het$^1$, Het$^1$alkyl, Het$^1$oxy, Het$^1$oxyalkyl, aryl, aryloxy, aryloxyalkyl, aralkyl, alkyloxycarbonylamino, amino, and aminoalkyl whereby each of the amino groups may optionally be mono- or where possible di-substituted with alkyl.

The term "alkoxy" or "alkyloxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy, hexanoxy and the like.

The term "arylthioalkoxy" means alkoxy as defined herein, wherein an alkyl hydrogen atom is replaced by an arylthio as defined herein. Examples of (arylthio) alkoxy radicals include 2-(phenylthio)-ethoxy, and the like.

The term "alkanoyl" or "alkylcarbonyl", alone or in combination, means an acyl radical derived from an alkanecarboxylic acid, examples of which include acetyl, propionyl, butyryl, valeryl, 4-methylvaleryl, and the like.

The term "alkylamino" means an alkyl amine radical, wherein the term "alkyl" is defined as above. Examples of alkylamino radicals include methylamino (NHCH$_3$), ethylamino (NHCH$_2$CH$_3$), n-propylamino, isopropylamino, n-butylamino, isobutylamino, sec-butylamino, tert-butylamino, n-hexylamino, and the like.

The term "alkylthio" means an alkyl thioether radical, wherein the term "alkyl" is defined as above. Examples of alkylthio radicals include methylthio (SCH$_3$), ethylthio (SCH$_2$CH$_3$), n-propylthio, isopropylthio, n-butylthio, isobutylthio, sec-butylthio, tert-butylthio, n-hexylthio, and the like.

The term "aminoalkanoyl" means an acyl group derived from an amino-substituted alkylcarboxylic acid wherein the amino group can be a primary, secondary or tertiary amino group containing substituents selected from alkyl, aryl, aralkyl, cycloalkyl, cycloalkylalkyl radicals and the like.

The term "aminocarbonyl" alone or in combination, means an amino-substituted carbonyl (carbamoyl) group wherein the amino group can be a primary, secondary or tertiary amino group containing substituents selected from alkyl, aryl, aralkyl, cycloalkyl, cycloalkylalkyl radicals and the like.

The term "aralkanoyl" means an acyl radical derived from an aryl-substituted alkanecarboxylic acid such as phenylacetyl, 3-phenylpropionyl(hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like.

The term "aralkoxy" means alkoxy as defined herein, wherein an alkyl hydrogen atom is replaced by an aryl as defined herein. Examples of aralkoxy radicals include 2-phenylethoxy, 2-phenyl-1-propoxy, and the like.

The term "aralkoxycarbonyl", alone or in combination, means a radical of the formula aralkyl-O—C(O)— in which the term "aralkyl" has the significance given above. Examples of an aralkoxycarbonyl radical are benzyloxycarbonyl and 4-methoxyphenylmethoxycarbonyl.

The term "aralkylamino" means alkylamino as defined herein, wherein an alkyl hydrogen atom is replaced by an aryl as defined herein. Examples of aralkylamino radicals include 2-phenethylamino, 4-phenyl-n-butylamino, and the like.

The term "aralkylthio" means alkylthio as defined herein, wherein an alkyl hydrogen atom is replaced by an aryl as defined herein. Examples of aralkylthio radicals include 3-phenyl-2-propylthio, 2-(2-naphthyl)-ethylthio, and the like.

The term "aroyl" means an acyl radical derived from an arylcarboxylic acid, aryl having the meaning given above. Examples of such arylcarboxylic acid radicals include substituted and unsubstituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamidol-2-naphthoyl, and the like.

The term "arylaminoalkoxy" means alkoxy as defined herein, wherein an alkyl hydrogen atom is replaced by an arylamino as defined herein. Examples of (arylamino)alkoxy radicals include 2-(phenylamino)-ethoxy, 2-(2-naphthylamino)-1-butoxy, and the like.

The term "arylaminoalkyl" means alkyl as defined herein, wherein an alkyl hydrogen atom is replaced by an arylamino as defined herein. Examples of arylaminoalkyl radicals include phenylaminoethyl, 4-(3-methoxyphenylamino)-1-butyl, and the like.

The term "arylaminoalkylamino" means alkylamino as defined herein, wherein an alkyl hydrogen atom is replaced by an arylamino as defined herein. Examples of (arylamino)alkylamino radicals include 3-(naphthylamino)-propylamino, 4-(phenylamino)-1-butylamino, and the like.

The term "arylaminoalkylthio" means alkylthio as defined herein, wherein an alkyl hydrogen atom is replaced by an arylamino as defined herein. Examples of (arylamino)alkylthio radicals include 2-(phenylamino)-ethylthio, 3-(2-naphthylamino)-n-propylthio, and the like.

The term "aryloxy" means a radical of the formula aryl-O— in which the term aryl has the significance given above.

The term "aryloxyalkanoyl" means an acyl radical of the formula aryl-O-alkanoyl wherein aryl and alkanoyl have the meaning given above.

The term "aryloxyalkoxy" means alkoxy as defined herein, wherein an alkyl hydrogen atom is replaced by an aryloxy as defined herein. Examples of (aryloxy)alkoxy radicals include 2-phenoxyethoxy, 4-(3-aminophenoxy)-1-butoxy, and the like.

The term "aryloxyalkyl" means alkyl as defined herein, wherein an alkyl hydrogen atom is replaced by an aryloxy as defined herein. Examples of aryloxyalkyl radicals include phenoxyethyl, 4-(3-aminophenoxy-butyl, and the like.

The term "aryloxyalkylamino" means alkylamino as defined herein, wherein an alkyl hydrogen atom is replaced by an aryloxy as defined herein. Examples of (aryloxy) alkylamino radicals include 3-phenoxy-npropylamino, 4-phenoxybutylamino, and the like.

The term "aryloxyalkylthio" means alkylthio as defined herein, wherein an alkyl hydrogen atom is replaced by an aryloxy as defined herein. Examples of (aryloxy)alkylthio radicals include 3-phenoxypropylthio, 4 (2-fluorophenoxy)-butylthio, and the like.

The term "arylthioalkylamino" means alkylamino as defined herein, wherein an alkyl hydrogen atom is replaced by an arylthio as defined herein. Examples of (arylthio) alkylamino radicals include 2-(phenylthio)-ethylamino, and the like.

The term "arylthioalkylthio" means alkylthio as defined herein, wherein an alkyl hydrogen atom is replaced by an arylthio as defined herein. Examples of (arylthio)alkylthio radicals include 2-(naphthylthio)-ethylthio, 3-(phenylthio)-propylthio, and the like.

The term "cycloalkylalkoxycarbonyl" means an acyl group derived from a cycloalkylalkoxycarboxylic acid of the formula cycloalkylalkyl-O—COOH wherein cycloalkylalkyl has the meaning given above.

The term "cycloalkylcarbonyl" means an acyl group derived from a monocyclic or bridged cycloalkanecarboxylic acid such as cyclopropylcarbonyl, cyclohexylcarbonyl, adamantylcarbonyl, and the like, or from a benz-fused monocyclic cycloalkanecarboxylic acid which is optionally substituted by one or more substituents selected from alkyl, alkoxy, halogen, hydroxy, amino, nitro, cyano, haloalkyl, carboxy, alkoxycarbonyl, cycloalkyl, heterocycloalkyl, alkanoylamino, amido, mono and dialkyl substituted amino, mono and dialkyl substituted amido and the like, such as 1,2,3,4-tetrahydro-2-naphthoyl, 2-acetamido-1,2,3,4-tetrahydro-2-naphthoyl.

The term "$Het^2$alkoxy" means alkoxy as defined herein, wherein an alkyl hydrogen atom is replaced by a $Het^2$ as defined herein. Examples of $Het^2$alkoxy radicals include 2-pyridylmethoxy, 4-(I-imidazolyl)-butoxy, and the like.

The term "$Het^2$alkyl" means alkyl as defined herein, wherein an alkyl hydrogen atom is replaced by a Het as defined herein. Examples of $Het^2$alkyl radicals include 2-pyridylmethyl, 3-(4-thiazolyl)-propyl, and the like.

The term "$Het^2$alkylamino" means alkylamino as defined herein, wherein an alkyl hydrogen atom is replaced by a $Het^2$ as defined herein. Examples of $Het^2$alkylamino radicals include 4-pyridylmethylamino, 3 (2-furanyl)-propylamino, and the like.

The term "$Het^2$alkylthio" means alkylthio as defined herein, wherein an alkyl hydrogen atom is replaced by a $Het^2$ as defined herein. Examples of $Het^2$alkylthio radicals include 3-pyridylmethylthio, 3 (4-thiazolyl)-propylthio, and the like.

The term "$Het^2$amino" means $Het^2$ as defined herein, wherein a hydrogen atom on the $Het^2$ ring is replaced by a nitrogen. $Het^2$amino radicals include, for example, 4-thiazolylamino, 2-pyridylamino, and the like.

The term "$Het^2$oxy" means $Het^2$ as defined herein, wherein a hydrogen atom on the $Het^2$ ring is replaced by an oxygen. $Het^2$oxy radicals include, for example, 4-pyridyloxy, 5-quinolyloxy, and the like.

The term "$Het^2$oxycarbonyl" means an acyl radical derived from a carbonic acid represented by $Het^2$-O—COOH wherein $Het^2$ has the meaning given above.

The term "$Het^2$thio" means $Het^2$ as defined herein, wherein a hydrogen atom on the $Het^2$ ring is replaced by a sulfur. $Het^2$thio radicals include, for example, 3-pyridylthio, 3-quinolylthio, 4-imidazolylthio, and the like.

The term "$Het^1$alkanoyl" is an acyl radical derived from a $Het^1$-substituted alkylcarboxylic acid wherein $Het^1$ has the meaning given above.

The term "$Het^1$alkoxycarbonyl" means an acyl group derived from $Het^1$-O—COOH wherein $Het^1$ is as defined above.

As used herein before, the term "one or more" covers the possibility of all the available C-atoms, where appropriate, to be substituted, preferably, one, two or three. When any variable, e.g. halogen or alkyl, occurs more than one time in any constituent, each definition is independent.

According to another embodiment, the present invention relates to a compound having the formula I, wherein $R^1$ is selected from the group comprising hydrogen, alkyl, hydroxyalkyl, alkenyl, alkynyl, alkyloxyalkyl, alkylthioalkyl, alkyloxycarbonyl, alkanoyl, cycloalkylalkyl, cycloalkylcarbonyl, cycloalkylalkanoyl, cycloalkylalkoxycarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, aralkoxycarbonyl, arylthioalkyl, aralkanoyl, aroyl, carboxyl, formyl, alkenylcarbonyl, alkynylcarbonyl, $Het^1$oxyalkyl, $Het^1$alkoxycarbonyl, $Het^1$oxycarbonyl, $Het^1$aryloxyalkyl, $Het^1$alkyloxyalkyl, $Het^1$arylthioalkyl, $Het^1$aryloxycarbonyl, $Het^1$aralkoxycarbonyl, $Het^1$oxyalkylcarbonyl, $Het^1$alkyloxyalkylcarbonyl, $Het^1$aryloxyalkylcarbonyl, $Het^1$carbonyloxyalkyl, $Het^1$alkylcarbonyloxyalkyl, $Het^1$aralkylcarbonyloxyalkyl, $Het^2$oxyalkyl, $Het^2$alkyloxyalkyl, $Het^2$oxycarbonyl, $Het^2$alkoxycarbonyl, $Het^2$aralkoxycarbonyl, $Het^2$aryloxycarbonyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $Het^2$carbonyloxyalkyl, $Het^2$alkylcarbonyloxyalkyl, $Het^2$aralkylcarbonyloxyalkyl, $CR^6$=$NR^7$, $CR^6$=$N(OR^7)$, with $R^6$ and $R^7$ being independently selected from the group comprising hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkylthiocarbonylamino and arylthiocarbonylamino;

wherein $R^2$ and $R^3$ are independently selected from the group comprising hydroxyl, alkyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, aryloxycarbonylalkyloxy, formyloxy, $Het^1$alkyloxy, $Het^1$oxy, $Het^1$oxyalkyloxy, $Het^1$aryloxy, $Het^1$aralkyloxy, $Het^1$cycloalkyloxy, $Het^1$carbonyloxy, $Het^1$alkanoyloxy, $Het^1$aralkanoyloxy, $Het^1$aryloxyalkyloxy, $Het^2$oxy, $Het^2$alkyloxy; $Het^2$oxyalkyloxy, $Het^2$aralkyloxy, $Het^2$cycloalkyloxy, $Het^2$alkanoyloxy, $Het^2$aralkanoyloxy, $Het^2$carbonyloxyl, $Het^2$aryloxy, $Het^2$aryloxyalkyloxy, wherein $R^1$ $R^2$ and $R^3$ are optionally substituted by one or more substituents independently selected from the group indicated in claim 1; and wherein $R^4$ is selected from the group comprising, oxo, hydroxyalkyl, alkyl, alkenyl, alkylcarbonylalkyl, arylcarbonylalkyl and $R^5$ is hydrogen, oxo, hydroxyl, hydroxyalkyl, alkyl, alkenyl, alkylcarbonylalkyl, arylcarbonylalkyl.

According to a further embodiment, the present invention relates to a compound having the formula I, wherein $R^1$ is selected from the group comprising alkyl, alkenyl, alkynyl, alkyloxyalkyl, alkylthioalkyl, alkyloxycarbonyl, alkanoyl, cycloalkylalkyl, cycloalkylcarbonyl, cycloalkylalkanoyl, cycloalkylalkoxycarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, aralkoxycarbonyl, arylthioalkyl, aralkanoyl, aroyl, carboxyl, formyl, alkenylcarbonyl, alkynylcarbonyl, $Het^1$oxyalkyl, $Het^1$alkoxycarbonyl, $Het^1$oxycarbonyl, $Het^1$aryloxyalkyl, $Het^1$alkyloxyalkyl, $Het^1$arylthioalkyl, $Het^1$aryloxycarbonyl, $Het^1$aralkoxycarbonyl, $Het^1$oxyalkylcarbonyl, $Het^1$alkyloxyalkylcarbonyl, $Het^1$aryloxyalkylcarbonyl, $Het^1$carbonyloxyalkyl, $Het^1$alkylcarbonyloxyalkyl, $Het^1$aralkylcarbonyloxyalkyl, $Het^2$oxyalkyl, $Het^2$alkyloxyalkyl, $Het^2$oxycarbonyl, $Het^2$alkoxycarbonyl, $Het^2$aralkoxycarbonyl, $Het^2$aryloxycarbonyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $Het^2$carbonyloxyalkyl, $Het^2$alkylcarbonyloxyalkyl, $Het^2$aralkylcarbonyloxyalkyl, $CR^6$=$NR^7$, $CR^6$=$N(OR^7)$, with $R^6$ and $R^7$ being independently selected from the group comprising hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkylthiocarbonylamino and arylthiocarbonylamino;

wherein $R^2$ and $R^3$ are independently selected from the group comprising hydroxyl, alkyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, aryloxycarbonylalkyloxy, formyloxy, $Het^1$alkyloxy, $Het^1$oxy, $Het^1$oxyalkyloxy, $Het^1$aryloxy, $Het^1$aralkyloxy, $Het^1$cycloalkyloxy, $Het^1$carbonyloxy, $Het^1$alkanoyloxy, $Het^1$aralkanoyloxy, $Het^1$aryloxyalkyloxy, $Het^2$oxy, $Het^2$alkyloxy; $Het^2$oxyalkyloxy, $Het^2$aralkyloxy, $Het^2$cycloalkyloxy, $Het^2$alkanoyloxy, $Het^2$aralkanoyloxy, $Het^2$carbonyloxyl, $Het^2$aryloxy, $Het^2$aryloxyalkyloxy, wherein $R^1$ $R^2$ and $R^3$ are optionally substituted by one or more substituents independently selected from the group indicated above; and wherein $R^4$ is oxo and $R^5$ is hydrogen or alkyl.

According to a preferred embodiment, the present invention relates to a compound having the formula I, wherein $R^1$ is selected from the group comprising alkyl, alkenyl, alkynyl, alkyloxyalkyl, alkylthioalkyl, alkanoyl, cycloalkylalkyl, cycloalkylcarbonyl, cycloalkylalkanoyl, cycloalkylthioalkyl, silyloxyalkyl, aralkyl, arylalkenyl, arylcarbonyl, arylthioalkyl, aralkanoyl, aroyl, carboxyl, formyl, alkenylcarbonyl, alkynylcarbonyl, $Het^1$oxyalkyl, $Het^1$aryloxyalkyl, $Het^1$alkyloxyalkyl, $Het^1$arylthioalkyl, $Het^1$oxyalkylcarbonyl, $Het^1$alkyloxyalkylcarbonyl, $Het^1$aryloxyalkylcarbonyl, $Het^2$oxyalkyl, $Het^2$alkyloxyalkyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $CR^6$=$NR^7$, $CR^6$=$N(OR^7)$, with $R^6$ and $R^7$ being independently selected from the group comprising hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkylthiocarbonylamino and arylthiocarbonylamino;

wherein $R^2$ and $R^3$ are independently selected from the group comprising hydroxyl, alkylcarbonyloxy, arylcarbonyloxy, cycloalkylcarbonyloxy, formyloxy, $Het^1$carbonyloxy, $Het^1$alkanoyloxy, $Het^1$aralkanoyloxy, $Het^2$carbonyloxyl, $Het^2$alkanoyloxy, $Het^2$aralkanoyloxy, wherein $R^1$ $R^2$ and $R^3$ are optionally substituted by one or more substituents independently selected from the group indicated above; and wherein $R^4$ is oxo and $R^5$ is hydrogen or alkyl.

According to yet another preferred embodiment, the present invention relates to a compound having the formula I wherein $R^1$ is selected from the group comprising alkyl, alkenyl, alkynyl, alkyloxyalkyl, alkylthioalkyl, cycloalkylalkyl, cycloalkylthioalkyl, silyloxyalkyl, aralkyl, arylalkenyl, arylthioalkyl, carboxyl, formyl, $Het^1$oxyalkyl, $Het^1$aryloxyalkyl, $Het^1$alkyloxyalkyl, $Het^1$arylthioalkyl, $Het^2$oxyalkyl, $Het^2$alkyloxyalkyl, $Het^2$aryloxyalkyl, $Het^2$arylthioalkyl, optionally substituted by one or more substituents independently selected from the group indicated above; wherein $R^2$ and $R^3$ are hydroxyl and wherein $R^4$ is oxo and $R^5$ is hydrogen.

According to an even more preferred embodiment, the present invention relates to a compound having the formula I wherein $R^1$ is selected from the group comprising alkyl, alkenyl, alkynyl, alkyloxyalkyl, cycloalkylalkyl, silyloxyalkyl, aralkyl, arylalkenyl, carboxyl, formyl, $Het^1$oxyalkyl, $Het^1$aryloxyalkyl, $Het^1$alkyloxyalkyl, $Het^2$oxyalkyl, $Het^2$alkyloxyalkyl, $Het^2$aryloxyalkyl, optionally substituted by one or more substituents independently selected from the group indicated above; an wherein $R^2$ and $R^3$ are hydroxyl, $R^4$ is oxo and $R^5$ is hydrogen.

Even more preferred, the compound according to any the invention has an $R^1$ being selected from the group comprising alkyl, carboxyl, formyl; an $R^2$ and $R^3$ group being hydroxyl, an $R^4$ group being oxo and a $R^5$ being hydrogen.

In a preferred embodiment, the present invention relates to a compound having formula I, wherein $R^1$ is formyl, $R^2$ and $R^3$ are hydroxyl $R^4$ is oxo and $R^5$ is hydrogen. This particular compound is referred to herein as 2" oxo-voruscharin and is represented by the formula II:

formula II:

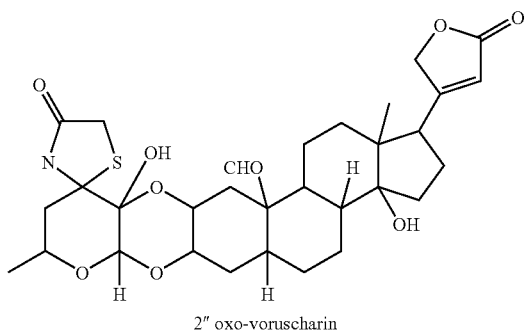

2" oxo-voruscharin

According to another embodiment, the present invention relates to a compound having the formula I, wherein $R^1$ is selected from the group comprising hydrogen, alkyl, alkenyl, alkynyl, alkyloxyalkyl, hydroxyalkyl, alkylthioalkyl, alkanoyl, cycloalkylalkyl, cycloalkylcarbonyl, cycloalkylalkanoyl, cycloalkylthioalkyl, silyloxyalkyl, aralkyl, arylalkenyl, arylcarbonyl, arylthioalkyl, aralkanoyl, aroyl, carboxyl, formyl, alkenylcarbonyl, alkynylcarbonyl, $Het^1$oxyalkyl, $Het^1$aryloxyalkyl, $Het^1$alkyloxyalkyl, $Het^1$arylthioalkyl, $Het^1$oxyalkylcarbonyl, $Het^1$alkyloxyalkylcarbonyl, $Het^1$aryloxyalkylcarbonyl, $Het^2$oxyalkyl, $Het^2$alkyloxyalkyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $CR^6=NR^7$, $CR^6=N(OR^7)$,

- with $R^6$ and $R^7$ being independently selected from the group comprising hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkylthiocarbonylamino and arylthiocarbonylamino;
- wherein $R^2$ and $R^3$ are independently selected from the group comprising hydroxyl, alkylcarbonyloxy, arylcarbonyloxy, cycloalkylcarbonyloxy, formyloxy, $Het^1$carbonyloxy, $Het^1$alkanoyloxy, $Het^1$aralkanoyloxy, $Het^2$carbonyloxyl, $Het^2$alkanoyloxy, $Het^2$aralkanoyloxy,
- wherein $R^1$ $R^2$ and $R^3$ are optionally substituted by one or more substituents independently selected from the group indicated in claim 1; and wherein $R^4$ is oxo, hydroxyalkyl, alkyl, alkenyl, arylcarbonylaryl, alkylcarbonylalkyl and $R^5$ is hydrogen or alkyl.

In yet another preferred embodiment, the present invention relates to a compound of formula I, wherein $R^1$ is selected from the group comprising hydrogen, alkyl, alkenyl, alkynyl, hydroxyalkyl, alkyloxyalkyl, alkylthioalkyl, cycloalkylalkyl, cycloalkylthioalkyl, silyloxyalkyl, aralkyl, arylalkenyl, arylthioalkyl, carboxyl, formyl, $Het^1$oxyalkyl, $Het^1$aryloxyalkyl, $Het^1$alkyloxyalkyl, $Het^1$arylthioalkyl, $Het^2$oxyalkyl, $Het^2$alkyloxyalkyl, $Het^2$aryloxyalkyl, $Het^2$arylthioalkyl, optionally substituted by one or more substituents independently selected from the group indicated in claim 1; wherein $R^2$ and $R^3$ are hydroxyl and wherein $R^4$ is hydroxyalkyl, arylcarbonylalkyl, alkylcarbonylalkyl and $R^5$ is hydrogen.

In a more preferred embodiment, the compound of the formula I has $R^1$ which is selected from the group comprising hydrogen, alkyl, alkenyl, alkynyl, hydroxyalkyl, alkyloxyalkyl, cycloalkylalkyl, silyloxyalkyl, aralkyl, arylalkenyl, carboxyl, formyl, $Het^1$oxyalkyl, $Het^1$aryloxyalkyl, $Het^1$alkyloxyalkyl, $Het^2$oxyalkyl, $Het^2$alkyloxyalkyl, $Het^2$aryloxyalkyl, optionally substituted by one or more substituents independently selected from the group indicated in claim 1; wherein $R^2$ and $R^3$ are hydroxyl, $R^4$ is hydroxyalkyl, arylcarbonylalkyl, alkylcarbonylalkyl and $R^5$ is hydrogen.

In particular, the present invention relates to compounds of the formula I wherein $R^1$ is selected from the group comprising alkyl, hydroxyalkyl, carboxyl, formyl; wherein $R^2$ and $R^3$ are hydroxyl, and wherein $R^4$ is arylcarbonylalkyl and $R^5$ is hydrogen. More in particular, the present invention relates to compounds of the formula 1 wherein $R^1$ is hydroxyalkyl, $R^2$ and $R^3$ are hydroxyl, $R^4$ is arylcarbonylalkyl and $R^5$ is hydrogen.

The present invention aims to provide novel cardenolide glycosides, which have a cytotoxic activity, and which can consequently be used for in medical applications.

As explained above, the present invention provides novel 2" oxo-voruscharin and its derivatives. In another aspect, the present invention also relate to novel derivatives of the C. procera cardenolide glycoside uscharin. The novel uscharin derivatives according to the invention may be either extracted from the plant or synthesized.

In another embodiment the present invention thus relates to a compound of the formula Ia or a pharmaceutically acceptable salt thereof, formula Ia

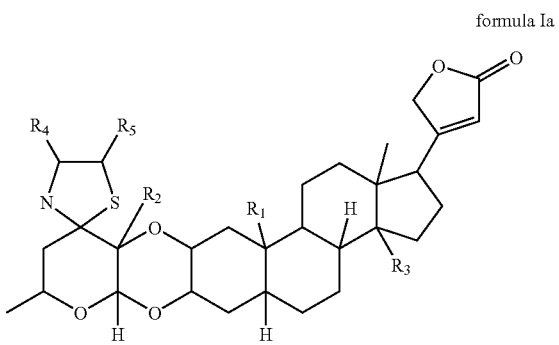

wherein $R^1$ is selected from the group comprising alkyl, alkenyl, alkynyl, alkyloxyalkyl, alkylthioalkyl, alkyloxycarbonyl, alkanoyl, cycloalkylalkyl, cycloalkylcarbonyl, cycloalkylalkanoyl, cycloalkylalkoxycarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, aralkoxycarbonyl, arylthioalkyl, aralkanoyl, aroyl, silyloxyalkyl, carboxyl, alkenylcarbonyl, alkynylcarbonyl, Het$^1$oxyalkyl, Het$^1$alkoxycarbonyl, Het$^1$oxycarbonyl, Het$^1$aryloxyalkyl, Het$^1$alkyloxyalkyl, Het$^1$arylthioalkyl, Het$^1$aryloxycarbonyl, Het$^1$aralkoxycarbonyl, Het$^1$oxyalkylcarbonyl, Het$^1$alkyloxyalkylcarbonyl, Het$^1$aryloxyalkylcarbonyl, Het$^1$carbonyloxyalkyl, Het$^1$alkylcarbonyloxyalkyl, Het$^1$aralkylcarbonyloxyalkyl, Het$^2$oxyalkyl, Het$^2$alkyloxyalkyl, Het$^2$oxycarbonyl, Het$^2$alkoxycarbonyl, Het$^2$aralkoxycarbonyl, Het$^2$aryloxycarbonyl, Het$^2$aryloxyalkyl, Het$^2$arylthioalkyl, Het$^2$oxyalkylcarbonyl, Het$^2$alkyloxyalkylcarbonyl, Het$^2$aryloxyalkylcarbonyl, Het$^2$carbonyloxyalkyl, Het$^2$alkylcarbonyloxyalkyl, Het$^2$aralkylcarbonyloxyalkyl, CR$^6$=NR$^7$, CR$^6$=N(OR$^7$), with R$^6$ and R$^7$ being independently selected from the group comprising hydrogen, hydroxyl, alkyl, aryl, Het$^1$, Het$^1$alkyl, Het$^1$aryl, alkenyl, alkynyl, aminoalkyl, aminoaryl, alkylcarbonylamino, arylcarbonylamino, alkylthiocarbonylamino and arylthiocarbonylamino;

wherein R$^2$ and R$^3$ have the same definition as indicated above;

wherein R$^1$ R$^2$ and R$^3$ are optionally substituted by one or more substituents independently selected from the group as indicated above, and wherein R$^4$ and R$^5$ are hydrogen or alkyl.

In a preferred embodiment the uscharin derivative according to the invention is a compound having the formula Ia, wherein R$^1$ is selected from the group comprising alkyl, alkenyl, alkynyl, alkyloxyalkyl, alkylthioalkyl, alkanoyl, cycloalkylalkyl, cycloalkylcarbonyl, cycloalkylalkanoyl, cycloalkylthioalkyl, silyloxyalkyl, aralkyl, arylalkenyl, arylcarbonyl, arylthioalkyl, aralkanoyl, aroyl, silyloxyalkyl, carboxyl, alkenylcarbonyl, alkynylcarbonyl, Het$^1$oxyalkyl, Het$^1$aryloxyalkyl, Het$^1$alkyloxyalkyl, Het$^1$arylthioalkyl, Het$^1$oxyalkylcarbonyl, Het$^1$alkyloxyalkylcarbonyl, Het$^1$aryloxyalkylcarbonyl, Het$^2$oxyalkyl, Het$^2$alkyloxyalkyl, Het$^2$aryloxyalkyl, Het$^2$arylthioalkyl, Het$^2$oxyalkylcarbonyl, Het$^2$alkyloxyalkylcarbonyl, Het$^2$aryloxyalkylcarbonyl, CR$^6$=NR$^7$, CR$^6$=N(OR$^7$), with R$^6$ and R$^7$ being independently selected from the group comprising hydrogen, hydroxyl, alkyl, aryl, Het$^1$, Het$^1$alkyl, Het$^1$aryl, alkenyl, alkynyl, aminoalkyl, aminoaryl, alkylcarbonylamino, arylcarbonylamino, alkylthiocarbonylamino and arylthiocarbonylamino; wherein R$^2$ and R$^3$ have the same definition as above indicated; wherein R$^1$ R$^2$ and R$^3$ are optionally substituted by one or more substituents independently selected from the group as indicated above, and wherein R$^4$ and R$^5$ are hydrogen or alkyl.

In a even more preferred embodiment, the invention relates to an uscharin derivative having the formula Ia, wherein R$^1$ is selected from the group comprising alkyl, alkenyl, alkynyl, alkyloxyalkyl, alkylthioalkyl, cycloalkylalkyl, cycloalkylthioalkyl, silyloxyalkyl, aralkyl, arylalkenyl, arylthioalkyl, silyloxyalkyl, carboxyl, Het$^1$oxyalkyl, Het$^1$aryloxyalkyl, Het$^1$alkyloxyalkyl, Het$^1$arylthioalkyl, Het$^2$oxyalkyl, Het$^2$alkyloxyalkyl, Het$^2$aryloxyalkyl, Het$^2$arylthioalkyl, optionally substituted by one or more substituents independently selected from the group indicated in above; wherein R$^2$ and R$^3$ are hydroxyl and wherein R$^4$ and R$^5$ are hydrogen or alkyl.

In another preferred embodiment, the invention relates to an uscharin derivative having the formula Ia, wherein R$^1$ is selected from the group comprising alkyl, alkenyl, alkynyl, alkyloxyalkyl, cycloalkylalkyl, silyloxyalkyl, aralkyl, arylalkenyl, carboxyl, Het$^1$oxyalkyl, Het$^1$aryloxyalkyl, Het$^1$alkyloxyalkyl, Het$^2$oxyalkyl, Het$^2$alkyloxyalkyl, Het$^2$aryloxyalkyl, optionally substituted by one or more substituents independently selected from the group indicated above; wherein R$^2$ and R$^3$ are hydroxyl and wherein R$^4$ and R$^5$ are hydrogen.

Another further embodiment of the invention relates to a compound of formula Ib,

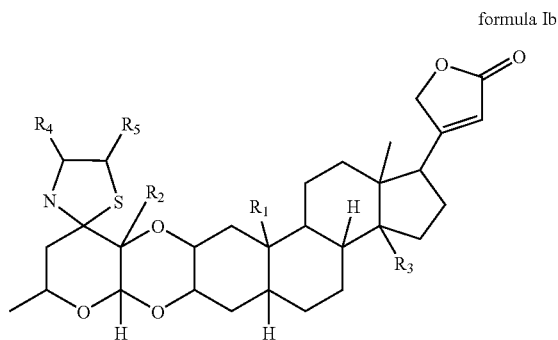

formula Ib wherein R$^1$ is selected from the group comprising alkenyl, alkynyl, alkyloxyalkyl, alkylthioalkyl, alkyloxycarbonyl, alkanoyl, cycloalkylalkyl, cycloalkylcarbonyl, cycloalkylalkanoyl, cycloalkylalkoxycarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, aralkoxycarbonyl, arylthioalkyl, aralkanoyl, aroyl, silyloxyalkyl, carboxyl, alkenylcarbonyl, alkynylcarbonyl, Het$^1$oxyalkyl, Het$^1$alkoxycarbonyl, Het$^1$oxycarbonyl, Het$^1$aryloxyalkyl, Het$^1$alkyloxyalkyl, Het$^1$arylthioalkyl, Het$^1$aryloxycarbonyl, Het$^1$aralkoxycarbonyl, Het$^1$oxyalkylcarbonyl, Het$^1$alkyloxyalkylcarbonyl, Het$^1$aryloxyalkylcarbonyl, Het$^1$carbonyloxyalkyl, Het$^1$alkylcarbonyloxyalkyl, Het$^1$aralkylcarbonyloxyalkyl, Het$^1$oxyalkyl, Het$^2$alkyloxyalkyl, Het$^2$oxycarbonyl, Het$^2$alkoxycarbonyl, Het$^2$aralkoxycarbonyl, Het$^2$aryloxycarbonyl, Het$^2$aryloxyalkyl, Het$^2$arylthioalkyl, Het$^2$oxyalkylcarbonyl, Het$^2$alkyloxyalkylcarbonyl, Het$^2$aryloxyalkylcarbonyl, Het$^2$carbonyloxyalkyl, Het$^2$alkylcarbonyloxyalkyl, Het$^2$aralkylcarbonyloxyalkyl, CR$^6$=NR$^7$, CR$^6$=N(OR$^7$), with R$^6$ and R$^7$ being independently selected from the group comprising hydrogen, hydroxyl, alkyl, aryl, Het$^1$, Het$^1$alkyl, Het$^1$aryl, alkenyl, alkynyl, aminoalkyl, aminoaryl, alkylcarbonylamino, arylcarbonylamino, alkylthiocarbonylamino and arylthiocarbonylamino;

wherein R$^1$ is optionally substituted by one or more substituents independently selected from the group as indicated above, wherein R$^2$ and R$^3$ are hydroxyl and wherein R$^4$ is replaced by a double bond between the N atom and the C carbon atom of the N-containing heterocyclic ring of formula I; and wherein R$^5$ is hydrogen.

According to this embodiment, this compound may also be represented by the formula III:

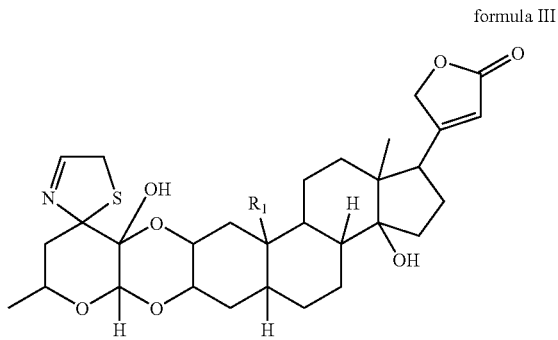

formula III

In a further embodiment, the present invention relates to a compound of formula III, wherein $R^1$ is selected from the group comprising alkenyl, alkynyl, alkyloxyalkyl, cycloalkylalkyl, silyloxyalkyl, aralkyl, arylalkenyl, carboxyl, $Het^1$oxyalkyl, $Het^1$aryloxyalkyl, $Het^1$alkyloxyalkyl, $Het^2$oxyalkyl, $Het^2$alkyloxyalkyl, $Het^2$aryloxyalkyl, optionally substituted by one or more substituents independently selected from the group indicated in above.

Non-limiting examples of compounds according to the present invention include compound of the formula I wherein $R^1$ is formyl, $R^2$ and $R^3$ are hydroxyl, $R^4$ is oxo and $R^5$ is hydrogen; compound of the formula I wherein $R^1$ is hydroxymethylene, $R^2$ and $R^3$ are hydroxyl, $R^4$ is phenylcarbonylmethylene and $R^5$ is hydrogen, compound of the formula I with $R^1$ being hydroxymethylene, $R^2$ and $R^3$ are hydroxyl, $R^4$ is oxo and $R^5$ is hydrogen, compound of the formula I with $R^1$ being acetyloxymethylene, $R^2$ and $R^3$ are hydroxyl, $R^4$ is oxo and $R^5$ is hydrogen; compound of the formula I wherein $R^1$ is benzoyloxymethylene, $R^2$ and $R^3$ are hydroxyl, $R^4$ is oxo and $R^5$ is hydrogen; compound of the formula I, wherein $R^1$ is hydroxymethylene, $R^2$ and $R^3$ are hydroxyl, $R^4$ is replaced by a double bond between the N atom and the C carbon atom of the N-containing heterocyclic ring of formula I; and $R^5$ is hydrogen; compound of the formula I wherein $R^1$ is acetyloxymethylene, $R^2$ and $R^3$ are hydroxyl, $R^4$ is replaced by a double bond between the N atom and the C carbon atom of the N-containing heterocyclic ring of formula I; and $R^5$ is hydrogen; compound of the formula I wherein $R^1$ is benzoyloxymethylene, $R^2$ and $R^3$ are hydroxyl, $R^4$ is replaced by a double bond between the N atom and the C carbon atom of the N-containing heterocyclic ring of formula I; and $R^5$ is hydrogen.

Whenever used hereinafter, the term "Compounds of the invention" or "derivatives" or "analogues" or a similar term is meant to include the compounds of general formula I, formula II or formula III, i.e. the 2" oxo-voruscharin and its derivatives, the uscharin derivatives and any subgroup thereof. This term also refers to the compounds as depicted in Table A and their N-oxides, salts, stereoisomeric forms, racemic mixtures, pro-drugs, esters and metabolites, as well as their quaternized nitrogen derivatives. The N-oxide forms of said compounds are meant to comprise compounds wherein one or several nitrogen atoms are oxidized to the so-called N-oxide.

The term "pro-drug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing prodrugs generally is hereby incorporated. Pro-drugs of the compounds of the invention can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792 all incorporated herein by reference. Pro-drugs are characterized by excellent aqueous solubility, increased bioavailability and are readily metabolized into the active inhibitors in vivo.

The compounds according to the invention may also exist in their tautomeric forms. Such forms, although not explicitly indicated in the compounds described herein, are intended to be included within the scope of the present invention.

The term stereochemically isomeric forms of the compounds according to the invention, as used herein, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound herein encompasses the mixture of all possible stereochemically isomeric forms, which said compound may possess. Said mixture may contain all diastereomers and/or enantiomers of the basic molecular structure of said compound. All stereochemically isomeric forms of the compounds of the invention either in pure form or in admixture with each other are intended to be embraced within the scope of the present invention.

For therapeutic use, the salts of the compounds according to the invention are those wherein the counterion is pharmaceutically or physiologically acceptable.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such a sarginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

The pharmaceutically acceptable esters of the compounds according to the invention refer to non-toxic esters, preferably the alkyl esters such as methyl, ethyl, propyl, isopropyl, butyl, isobutyl, or pentyl esters, of which the methyl ester is preferred. However, other esters such as phenyl-alkyl may be employed if desired.

The compounds according to the invention show cytotoxic activities, which implies that the may be used in various medical applications. As is demonstrated in the examples given below, the compounds according to the invention have in vitro anti-tumor activity.

Furthermore, the compounds according to the invenbon exhibit a low toxicity level. "Toxicity" is related to the detrimental effect a compound may exhibit on healthy cells, tissues or organs. The toxicity level of the compounds according to the invention is surprisingly low. The compounds according to the invention combine the essential features of a good anti-tumor activity and a low level of toxicity. Consequently the compounds according to the invention may be used in pharmaceutical compositions for the treatment of various diseases. In addition, because they have a low level of toxicity the compounds according to the invention may be used during longer periods of treatments.

The present invention also relates to a pharmaceutical composition comprising a pharmaceutically acceptable excipient and a therapeutic amount of a compound according to the invention. More in particular, the present invention relates to a pharmaceutical composition comprising a therapeutically effective amount of 2" oxo-voruscharin and a pharmaceutically acceptable excipient.

The term "therapeutically effective amount" as used herein means that amount of active compound or component or pharmaceutical agent that elicits the biological or medicinal response in a tissue, system, animal or human that is being sought by a researcher, veterinarian, medical doctor or other clinician, which includes alleviation of the symptoms of the disease being treated.

The pharmaceutical composition can be prepared in a manner known per se to one of skill in the art. For this purpose, at least one compound according to the invention having formula I or any subgroup or derivative thereof, one or more solid or liquid pharmaceutical excipients and, if desired, in combination with other pharmaceutical active compounds, are brought into a suitable administration form or dosage form which can then be used as a pharmaceutical in human medicine or veterinary medicine.

Particular forms of the pharmaceutical composition may be, for example, solutions, suspensions, emulsions, creams, tablets, capsules, nasal sprays, liposomes or micro-reservoirs, especially compositions in orally ingestible or sterile injectable form, for example, as sterile injectable aqueous or oleaginous suspensions or suppositories. The preferred form of composition contemplated is the dry solid form, which includes capsules, granules, tablets, pills, boluses and powders. The solid carrier may comprise one or more excipients, e.g. lactose, fillers, disintegrating agents, binders, e.g. cellulose, carboxymethylcellulose or starch or anti-stick agents, e.g. magnesium stearate, to prevent tablets from adhering to tabletting equipment. Tablets, pills and boluses may be formed so as to disintegrate rapidly or to provide slow release of the active ingredient.

In order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the compounds of the invention are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkyloxycarbonylalkyl or carboxyalkyloxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxy groups are etherified with different groups such as, for example, hydroxypropyl and hydroxyethyl. An interesting way of formulating the compounds according to the invention in combination with a cyclodextrin or a derivative thereof has been described in EP-A-721, 331. Although the formulations described therein are with antifungal active ingredients, they are equally interesting for formulating the compounds according to the invention. Said formulations may also be rendered more palatable by adding pharmaceutically acceptable sweeteners and/or flavors.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered. The term "a solid dispersion" also comprises dispersions that are less homogenous throughout than solid solutions. Such dispersions are not chemically and physically uniform throughout or comprise more than one phase.

The water-soluble polymer is conveniently a polymer that has an apparent viscosity of 1 to 100 mPa.s when dissolved in a 2% aqueous solution at 20° C. solution. Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule. The compounds according to the invention as defined hereinabove can be prepared by first preparing a solid dispersion of the compounds according to the invention, and then optionally grinding or milling that dispersion. Various techniques exist for preparing solid dispersions including melt-extrusion, spray-drying and solution-evaporation, melt-extrusion being preferred.

It may further be convenient to formulate the compounds according to the invention in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Said beads comprise (a) a central, rounded or spherical core, (b) a coating film of a hydrophilic polymer and an antiretroviral agent and (c) a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

Another important feature attributed to the compounds according to the invention is their broad application possibility. The compounds according to the invention are highly active against several types of cancers. As will be shown in the examples described below, the compounds according to the invention exert significant anti-tumor effects on several tumor models tested, including glioma, colon, lung and bladder cancer (see examples). Importantly, the compounds according to the invention exhibit anti-tumor activity on a broad panel of histological tumor types.

Therefore, due to their favorable pharmacological properties the compounds according to the present invention are particularly suitable for use as medicaments in the treatment of individuals suffering from diseases associated with cell proliferation. In another embodiment, the compounds according to the present invention are used as a medicament. In yet another embodiment, the compounds according to the present invention are used in the preparation of a medicament for treating diseases associated with cell proliferation. In particular the compounds according to the present invention are used in the preparation of a medicament for treating cancer.

The term "individual," as used herein refers to an animal, preferably a mammal, and most preferably a human, who has been the object of treatment, observation or experiment.

The term "diseases associated with cell proliferation" as used herein refers to, but is not limited to, any type of cancer or condition involving cell proliferation. The compounds of the invention may be especially used in the treatment of cancers such as, but not limited to, leukemia, non-small cell lung cancer, small cell lung cancer, colon cancer, CNS cancer, melanoma, ovarian cancer, renal cancer, prostate cancer, breast cancer, glioma, bladder cancer, head and neck cancer, pancreas cancer, skin cancer, liver cancer, bone cancer and lymphoma.

In addition, the compounds according to the invention may also be very suitable in the treatment of scar tissue and wounds. It is believed that most, if not all, of the compounds of the present invention can act as active ingredients in treating scar tissue and in promoting wound healing and tissue regeneration.

In another embodiment, the invention relates to a method of treatment of diseases associated with cell proliferation comprising administrating to an individual in need of such treatment a pharmaceutical composition according to the invention. In particular, the invention relates to a method of treating cancer comprising administrating to an individual in need of such treatment a pharmaceutical composition according to the invention.

For these purposes, the pharmaceutical composition of the present invention may be administered orally, parenterally, i.e. including subcutaneous injections, intravenous, intramuscular, intrasternal injection or infusion techniques, by inhalation spray, or rectally, in dosage unit formulations containing conventional non-toxic pharmaceutically acceptable carriers, adjuvants and vehicles.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

Essentially, the primary modes of treatment of solid tumor cancers comprise surgery, radiation therapy and chemotherapy, separately and in combination. The compounds according to the invention are suitable for use in combination with these medicinal techniques. The compounds of the invention may be useful in increasing the sensitivity of tumor cells to radiation in radiotherapy and also in potentiating or enhancing damage to tumors by chemotherapeutic agents. The compounds and their pharmaceutically acceptable salts may also be useful for sensitizing multidrug-resistant tumor cells. The compounds according to the invention are useful therapeutic compounds for administration in conjunction with other DNA-damaging cytotoxic drugs or radiation used in radiotherapy to potentiate their effect.

In another embodiment of the method of the invention, the administration may be performed with food, e.g., a high-fat meal. The term 'with food' means the consumption of a meal either during or no more than about one hour before or after administration of a pharmaceutical composition according to the invention.

For an oral administration form, the compositions of the present invention can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

The oral administration of a pharmaceutical composition comprising a compound according to the invention, or a pharmaceutically acceptable salt or ester thereof, is suitably accomplished by uniformly and intimately blending together a suitable amount of a compound according to the invention in the form of a powder, optionally also including a finely divided solid carrier, and encapsulating the blend in, for example, a hard gelatin capsule. The solid carrier can include one or more substances, which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Oral administration of a pharmaceutical composition comprising a compound according to the invention, or a pharmaceutically acceptable salt or ester thereof can also be accomplished by preparing capsules or tablets containing the desired amount of a compound according to the invention, optionally blended with a solid carrier as described above. Compressed tablets containing the pharmaceutical composition of the invention can be prepared by uniformly and intimately mixing the active ingredient with a solid carrier such as described above to provide a mixture having the necessary compression properties, and then compacting the mixture in a suitable machine to the shape and size desired. Molded tablets maybe made by molding in a suitable machine, a mixture of powdered compound according to the invention moistened with an inert liquid diluent.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the active compounds of the invention, if desired with the substances customary therefor such as solubilizers, emulsifiers or further auxiliaries, are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquidify and/or dissolve in the rectal cavity to release the drug.

The pharmaceutical compositions of this invention can be administered to humans in dosage ranges specific for each compound of the invention comprised in said compositions. The compounds comprised in said composition can be administered together or separately.

It will be understood, however, that specific dose level and frequency of dosage for any particular patient may be varied and will depend upon a variety of factors including the activity of the specific compound of the invention employed, the metabolic stability and length of action of that compound, the age, body weight, general health, sex, diet, mode and time of administration, rate of excretion, drug combination, the severity of the particular condition, and the host undergoing therapy.

The compounds according to the invention may be prepared by a method of chemical synthesis, starting from 2"oxo-voruscharin or uscharin or other compounds. The methods of synthesis of the compounds according to the invention involve chemical modifications of 2"oxo-voruscharin or uscharin or derivatives thereof. 2"oxo-voruscharin or uscharin can be obtained by any convenient method, for example by chemical synthesis. Alternatively, it may also be obtained from extraction and purification from e.g. plants of the Asclepiadacaeae family, which produce 2"oxo-voruscharin and uscharin naturally, e.g. *Calotropis procera*.

The following examples are meant to illustrate the present invention. These examples are presented to exemplify the invention and are not to be considered as limiting the scope of the invention.

EXAMPLES

Example 1 provides a non-limiting list of examples of compounds according to the invention. Example 2 illustrates the preparation of certain compounds according to the invention. Example 3 and 4 illustrate the in vitro anti-tumor effects of several compounds according to the invention. The anti-tumor effects of the compounds according to the invention are compared to the anti-tumor activity of uscharin. Example 5 relates to the determination of the Maximum Tolerated Dose for the compounds according to the invention. Example 6 relates to the determination of the in-vivo anti-tumor pharmacology of the compounds according to the invention, in different cancer models.

Example 1

Non-limiting Examples of Compounds According to the Invention are Listed Hereunder in Table A

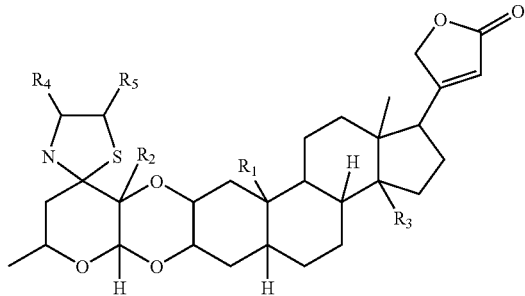

| R¹ | R² | R³ | R⁴ | R⁵ |
|---|---|---|---|---|
| —COOH | —OH | —OH | =O | —H |
| —CO$_2$CH$_3$ | —OH | —OH | =O | —H |
| —CO$_2$C$_2$H$_5$ | —OH | —OH | =O | —H |
| —CHO | —OH | —OH | =O | —H |
| —CH$_2$OH | —OH | —OH | =O | —H |
| —CHOHCH$_3$ | —OH | —OH | =O | —H |
| —CH$_2$—CH$_2$—CH=CH$_2$ | —OH | —OH | =O | —H |
| —COOCH$_3$ | —OH | —OH | =O | —H |
| —CH$_2$OCH$_3$ | —OH | —OH | =O | —H |
| —CH$_2$OCH$_2$CH$_3$ | —OH | —OH | =O | —H |
| —CH$_2$SCH$_3$ | —OH | —OH | =O | —H |
| —CH=N—OH | —OH | —OH | =O | —H |
| 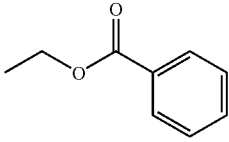 | —OH | —OH | =O | —H |
| 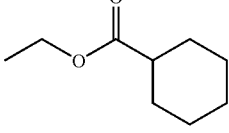 | —OH | —OH | =O | —H |
| 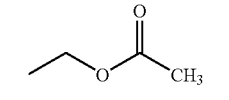 | —OH | —OH | =O | —H |
| 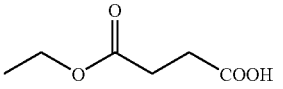 | —OH | —OH | =O | —H |
| 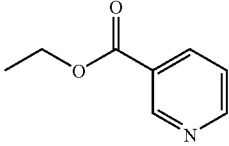 | —OH | —OH | =O | —H |
| 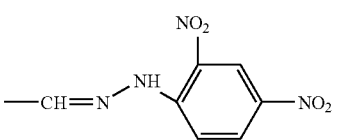 | —OH | —OH | =O | —H |

-continued

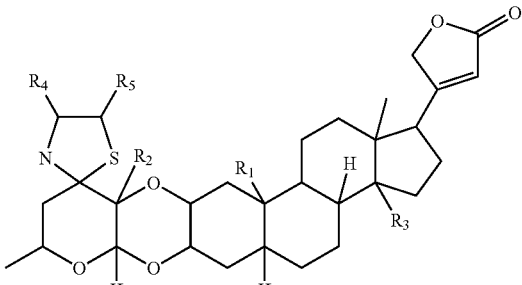

| R¹ | R² | R³ | R⁴ | R⁵ |
|---|---|---|---|---|
| —CH=N—Ph | —OH | —OH | =O | —H |
| —C(O)CH₃ (acetyl) | —OH | —OH | =O | —H |
| —C(O)Ph (benzoyl) | —OH | —OH | =O | —H |
| —CH(OH)CH₂CH₂CH₃ (2-hydroxypentyl) | —OH | —OH | =O | —H |
| —CH(OH)CH₃ (isopropanol) | —OH | —OH | =O | —H |
| —OC(O)Ph (phenyl acetate) | —OH | —OH | =O | —H |
| —C(O)CH₂CH₂CH₃ | —OH | —OH | =O | —H |
| —COOH | —O—CH₂CH₃ | —O—CH₃ | —H | =O |
| —CO₂CH₃ | —O—CH₂CH₃ | —O—CH₃ | —H | =O |
| —CO₂C₂H₅ | —O—CH₂CH₃ | —O—CH₃ | —H | =O |
| —CHO | —O—CH₂CH₃ | —O—CH₃ | —H | =O |
| —CH₂OH | —O—CH₂CH₃ | —O—CH₃ | —H | =O |
| —CHOHCH₃ | —O—CH₂CH₃ | —O—CH₃ | —H | =O |
| —CH₂—CH₂—CH=CH₂ | —O—CH₂CH₃ | —O—CH₃ | —H | =O |
| —COOCH₃ | —O—CH₂CH₃ | —O—CH₃ | =O | —H |
| —CH₂OCH₃ | —O—CH₂CH₃ | —O—CH₃ | =O | —H |
| —CH₂OCH₂CH₃ | —O—CH₂CH₃ | —O—CH₃ | =O | —H |
| —CH₂SCH₃ | —O—CH₂CH₃ | —O—CH₃ | =O | —H |
| —CH=N—OH | —O—CH₂CH₃ | —O—CH₃ | =O | —H |
| ethyl benzoate group | —O—CH₂CH₃ | —O—CH₃ | =O | —H |

-continued

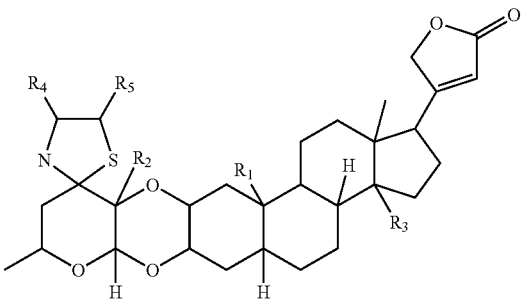

| R¹ | R² | R³ | R⁴ | R⁵ |
|---|---|---|---|---|
| ethyl cyclohexanecarboxylate group | —O—CH₂CH₃ | —O—CH₃ | =O | —H |
| ethyl acetate group | —O—CH₂CH₃ | —O—CH₃ | =O | —H |
| ethyl succinate group (—COOH) | —O—CH₂CH₃ | —O—CH₃ | =O | —H |
| ethyl nicotinate group | —O—CH₂CH₃ | —O—CH₃ | =O | —H |
| —CH=N—NH—(2,4-dinitrophenyl) | —O—CH₂CH₃ | —O—CH₃ | =O | —H |
| —CH=N—phenyl | —O—CH₂CH₃ | —O—CH₃ | =O | —H |
| acetyl (COCH₃) | —O—CH₂CH₃ | —O—CH₃ | =O | —H |
| benzoyl group | —O—CH₂CH₃ | —O—CH₃ | =O | —H |
| 2-hydroxypentyl (OH, CH₃) | —O—CH₂CH₃ | —O—CH₃ | =O | —H |
| 2-hydroxypropyl (OH, CH₃) | —O—CH₂CH₃ | —O—CH₃ | =O | —H |

-continued

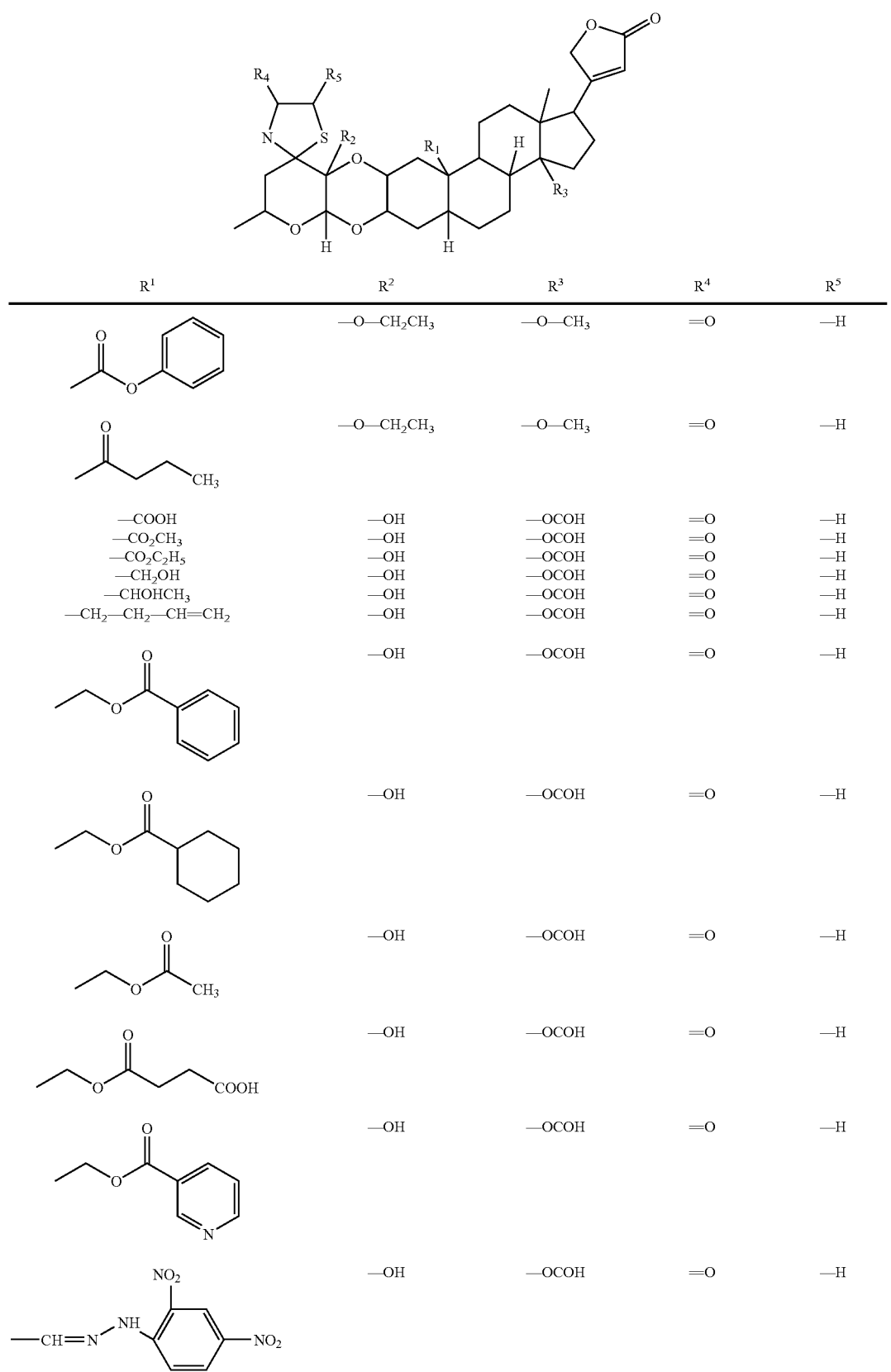

| R¹ | R² | R³ | R⁴ | R⁵ |
|---|---|---|---|---|
| phenyl acetate group | —O—CH$_2$CH$_3$ | —O—CH$_3$ | =O | —H |
| pentan-2-one group | —O—CH$_2$CH$_3$ | —O—CH$_3$ | =O | —H |
| —COOH | —OH | —OCOH | =O | —H |
| —CO$_2$CH$_3$ | —OH | —OCOH | =O | —H |
| —CO$_2$C$_2$H$_5$ | —OH | —OCOH | =O | —H |
| —CH$_2$OH | —OH | —OCOH | =O | —H |
| —CHOHCH$_3$ | —OH | —OCOH | =O | —H |
| —CH$_2$—CH$_2$—CH=CH$_2$ | —OH | —OCOH | =O | —H |
| ethyl benzoate group | —OH | —OCOH | =O | —H |
| ethyl cyclohexanecarboxylate group | —OH | —OCOH | =O | —H |
| ethyl acetate group | —OH | —OCOH | =O | —H |
| ethyl succinate group | —OH | —OCOH | =O | —H |
| ethyl nicotinate group | —OH | —OCOH | =O | —H |
| —CH=N—NH-(2,4-dinitrophenyl) | —OH | —OCOH | =O | —H |

-continued

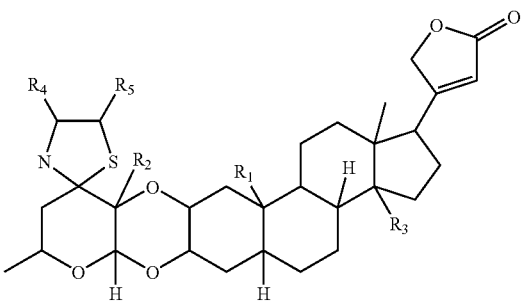

| R¹ | R² | R³ | R⁴ | R⁵ |
|---|---|---|---|---|
| —CH=N—C₆H₅ | —OH | —OCOH | =O | —H |
| —COCH₃ (acetone group) | —OH | —OCOH | =O | —H |
| —CO—C₆H₅ (phenyl ketone) | —OH | —OCOH | =O | —H |
| CH(OH)CH₂CH₂CH₃ (2-pentanol group) | —OH | —OCOH | =O | —H |
| CH(OH)CH₃ (isopropanol group) | —OH | —OCOH | =O | —H |
| —OC(O)—C₆H₅ (phenyl acetate) | —OH | —OCOH | =O | —H |
| —COCH₂CH₂CH₃ (2-pentanone group) | —OH | —OCOH | =O | —H |
| —COOH | —OH | —OH | —H | —H |
| —CO₂CH₃ | —OH | —OH | —H | —H |
| —CO₂C₂H₅ | —OH | —OH | —H | —H |
| —OH | —OH | —OH | —H | —H |
| —CH₂OH | —OH | —OCOH | —H | —H |
| —CHOHCH₃ | —OH | —OCOH | —H | —H |
| —CH₂—CH₂—CH=CH₂ | —OH | —OCOH | —H | —H |
| ethyl benzoate group | —OH | —OCOH | H | —H |

-continued
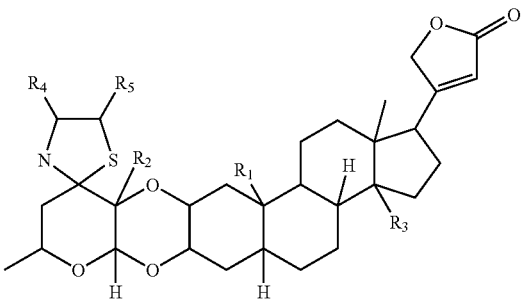
| R¹ | R² | R³ | R⁴ | R⁵ |
|---|---|---|---|---|
| ethyl cyclohexanecarboxylate group | —OH | —OH | —H | —H |
| ethyl acetate group | —OH | —OH | —H | —H |
| ethyl succinate (COOH) group | —OH | —OH | —H | —H |
| ethyl nicotinate group | —OH | —OH | —H | —H |
| —CH=N-NH-(2,4-dinitrophenyl) | —OH | —OCOH | —H | —H |
| —CH=N-phenyl | —OH | —OCOH | —H | —H |
| acetone (COCH₃) group | —OH | —OCOH | —H | —H |
| acetophenone group | —OH | —OCOH | H | —H |
| 2-hydroxypentyl group | —OH | —OH | —H | —H |
| 2-hydroxyisopropyl group | —OH | —OH | —H | —H |

-continued

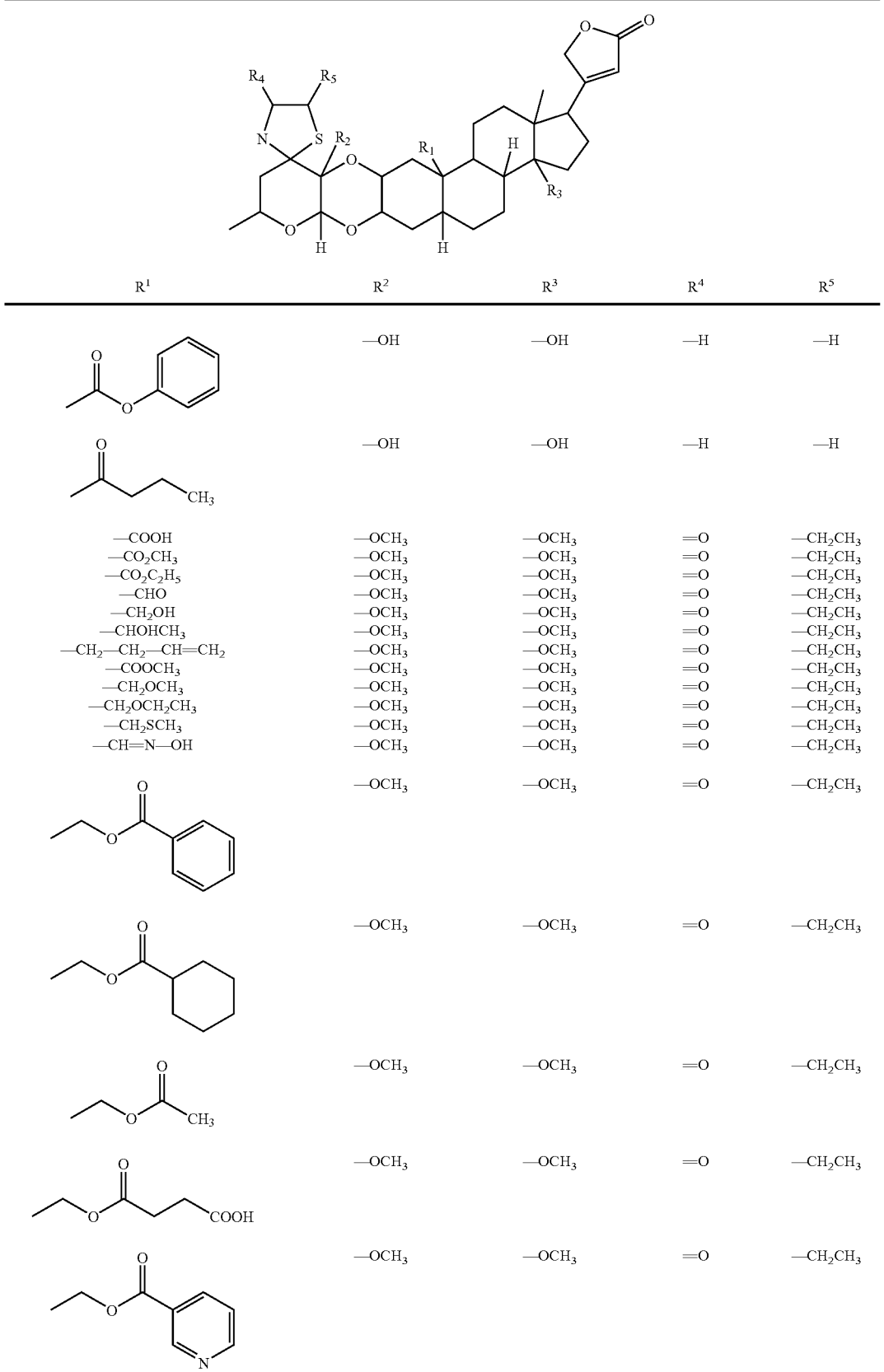

| R¹ | R² | R³ | R⁴ | R⁵ |
|---|---|---|---|---|
| (phenyl acetate group) | —OH | —OH | —H | —H |
| (pentan-2-one group) | —OH | —OH | —H | —H |
| —COOH | —OCH$_3$ | —OCH$_3$ | =O | —CH$_2$CH$_3$ |
| —CO$_2$CH$_3$ | —OCH$_3$ | —OCH$_3$ | =O | —CH$_2$CH$_3$ |
| —CO$_2$C$_2$H$_5$ | —OCH$_3$ | —OCH$_3$ | =O | —CH$_2$CH$_3$ |
| —CHO | —OCH$_3$ | —OCH$_3$ | =O | —CH$_2$CH$_3$ |
| —CH$_2$OH | —OCH$_3$ | —OCH$_3$ | =O | —CH$_2$CH$_3$ |
| —CHOHCH$_3$ | —OCH$_3$ | —OCH$_3$ | =O | —CH$_2$CH$_3$ |
| —CH$_2$—CH$_2$—CH=CH$_2$ | —OCH$_3$ | —OCH$_3$ | =O | —CH$_2$CH$_3$ |
| —COOCH$_3$ | —OCH$_3$ | —OCH$_3$ | =O | —CH$_2$CH$_3$ |
| —CH$_2$OCH$_3$ | —OCH$_3$ | —OCH$_3$ | =O | —CH$_2$CH$_3$ |
| —CH$_2$OCH$_2$CH$_3$ | —OCH$_3$ | —OCH$_3$ | =O | —CH$_2$CH$_3$ |
| —CH$_2$SCH$_3$ | —OCH$_3$ | —OCH$_3$ | =O | —CH$_2$CH$_3$ |
| —CH=N—OH | —OCH$_3$ | —OCH$_3$ | =O | —CH$_2$CH$_3$ |
| (ethyl benzoate group) | —OCH$_3$ | —OCH$_3$ | =O | —CH$_2$CH$_3$ |
| (ethyl cyclohexanecarboxylate group) | —OCH$_3$ | —OCH$_3$ | =O | —CH$_2$CH$_3$ |
| (ethyl acetate group) | —OCH$_3$ | —OCH$_3$ | =O | —CH$_2$CH$_3$ |
| (ethyl succinate group) | —OCH$_3$ | —OCH$_3$ | =O | —CH$_2$CH$_3$ |
| (ethyl nicotinate group) | —OCH$_3$ | —OCH$_3$ | =O | —CH$_2$CH$_3$ |

-continued

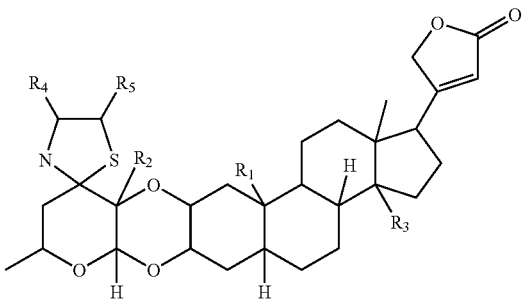

| R¹ | R² | R³ | R⁴ | R⁵ |
|---|---|---|---|---|
| —CH=N—NH—(2,4-dinitrophenyl) | —OCH₃ | —OCH₃ | =O | —CH₂CH₃ |
| —CH=N—phenyl | —OCH₃ | —OCH₃ | =O | —CH₂CH₃ |
| —C(=O)CH₃ | —OCH₃ | —OCH₃ | =O | —CH₂CH₃ |
| —C(=O)phenyl | —OCH₃ | —OCH₃ | =O | —CH₂CH₃ |
| —CH(OH)CH₂CH₂CH₃ (with CH₃) | —OCH₃ | —OCH₃ | =O | —CH₂CH₃ |
| —CH(OH)CH₃ | —OCH₃ | —OCH₃ | =O | —CH₂CH₃ |
| —C(=O)O-phenyl | —OCH₃ | —OCH₃ | =O | —CH₂CH₃ |
| —C(=O)CH₂CH₂CH₃ | —OCH₃ | —OCH₃ | =O | —CH₂CH₃ |
| —COOH | —O—CH₂-cyclohexyl | —OCH₂CH₃ | —H | —CH₂CH₃ |
| —CO₂CH₃ | —O—CH₂-cyclohexyl | —OCH₂CH₃ | —H | —CH₂CH₃ |
| —CO₂C₂H₅ | —O—CH₂-cyclohexyl | —OCH₂CH₃ | —H | —CH₂CH₃ |

-continued

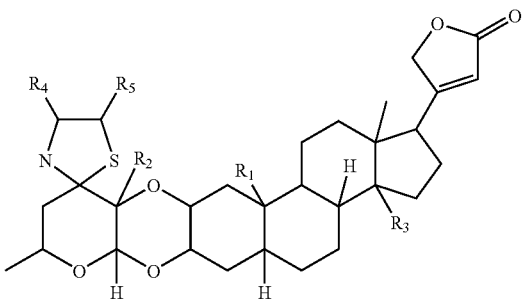

| R¹ | R² | R³ | R⁴ | R⁵ |
|---|---|---|---|---|
| —CHO | —O—CH₂—C₆H₁₁ | —OCH₂CH₃ | —H | —CH₂CH₃ |
| —CH₂OH | —O—CH₂—C₆H₁₁ | —OCH₂CH₃ | —H | —CH₂CH₃ |
| —CHOHCH₃ | —O—CH₂—C₆H₁₁ | —OCH₂CH₃ | —H | —CH₂CH₃ |
| —CH₂—CH₂—CH=CH₂ | —O—CH₂—C₆H₁₁ | —OCH₂CH₃ | —H | —CH₂CH₃ |
| —COOCH₃ | —O—CH₂—C₆H₁₁ | —OCH₂CH₃ | —H | —CH₂CH₃ |
| —CH₂OCH₃ | —O—CH₂—C₆H₁₁ | —OCH₂CH₃ | —H | —CH₂CH₃ |
| —CH₂OCH₂CH₃ | —O—CH₂—C₆H₁₁ | —OCH₂CH₃ | —H | —CH₂CH₃ |
| —CH₂SCH₃ | —O—CH₂—C₆H₁₁ | —OCH₂CH₃ | —H | —CH₂CH₃ |
| —CH=N—OH | —O—CH₂—C₆H₁₁ | —OCH₂CH₃ | —H | —CH₂CH₃ |
| ethyl benzoate group | —O—CH₂—C₆H₁₁ | —OCH₂CH₃ | —H | —CH₂CH₃ |
| ethyl cyclohexanecarboxylate group | —O—CH₂—C₆H₁₁ | —OCH₂CH₃ | —H | —CH₂CH₃ |

-continued
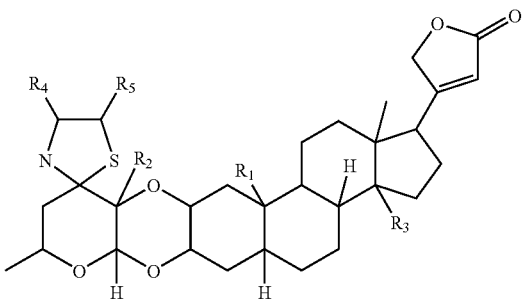
| R¹ | R² | R³ | R⁴ | R⁵ |
|---|---|---|---|---|
|  | 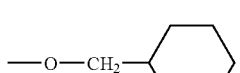 | —OCH₂CH₃ | —H | —CH₂CH₃ |
| 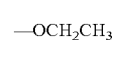 | 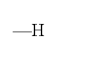 | —OCH₂CH₃ | —H | —CH₂CH₃ |
|  |  | —OCH₂CH₃ | —H | —CH₂CH₃ |
| 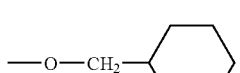 | 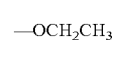 | —OCH₂CH₃ | —H | —CH₂CH₃ |
| 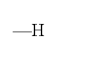 |  | —OCH₂CH₃ | —H | —CH₂CH₃ |
| 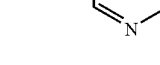 | 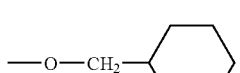 | —OCH₂CH₃ | —H | —CH₂CH₃ |
| 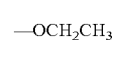 | 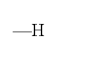 | —OCH₂CH₃ | —H | —CH₂CH₃ |
|  |  | —OCH₂CH₃ | —H | —CH₂CH₃ |
| 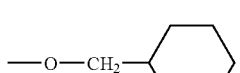 | 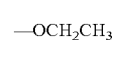 | —OCH₂CH₃ | —H | —CH₂CH₃ |
| 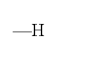 |  | —OCH₂CH₃ | —H | —CH₂CH₃ |

-continued

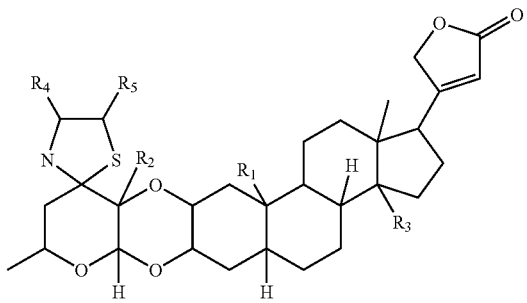

| R¹ | R² | R³ | R⁴ | R⁵ |
|---|---|---|---|---|
| ![ketone]  CH₃C(O)CH₂CH₂CH₃ (2-pentanone-yl) | —O—CH₂—cyclohexyl | —OCH₂CH₃ | —H | —CH₂CH₃ |
| —COOH | —O—CH₂CH₃ | —O—Si(CH₃)₃ | —CH₂CH₃ | —H |
| —CO₂CH₃ | —O—CH₂CH₃ | —O—Si(CH₃)₃ | —CH₂CH₃ | —H |
| —CO₂C₂H₅ | —O—CH₂CH₃ | —O—Si(CH₃)₃ | —CH₂CH₃ | —H |
| —CHO | —O—CH₂CH₃ | —O—Si(CH₃)₃ | —CH₂CH₃ | —H |
| —CH₂OH | —O—CH₂—CH₃ | —O—Si(CH₃)₃ | —CH₂CH₃ | —H |
| —CHOHCH₃ | —O—CH₂CH₃ | —O—Si(CH₃)₃ | —CH₂CH₃ | —H |
| —CH₂—CH₂—CH=CH₂ | —O—CH₂CH₃ | —O—Si(CH₃)₃ | —CH₂CH₃ | —H |
| —COOCH₃ | —O—CH₂CH₃ | —O—Si(CH₃)₃ | —CH₂CH₃ | —H |
| —CH₂OCH₃ | —O—CH₂CH₃ | —O—Si(CH₃)₃ | —CH₂CH₃ | —H |

-continued

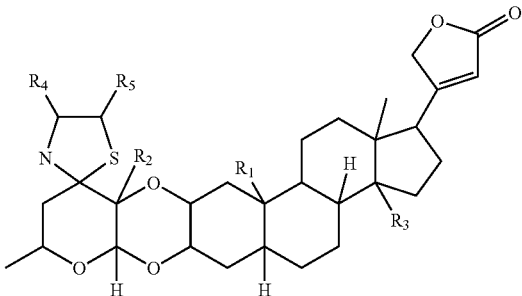

| R¹ | R² | R³ | R⁴ | R⁵ |
|---|---|---|---|---|
| —CH₂OCH₂CH₃ | —O—CH₂CH₃ | —O—Si(CH₃)₂—O—Si(CH₃)₃ | —CH₂CH₃ | —H |
| —CH₂SCH₃ | —O—CH₂CH₃ | —O—Si(CH₃)₂—O—Si(CH₃)₃ | —CH₂CH₃ | —H |
| —CH=N—OH | —O—CH₂CH₃ | —O—Si(CH₃)₂—O—Si(CH₃)₃ | —CH₂CH₃ | —H |
| ethyl benzoate group 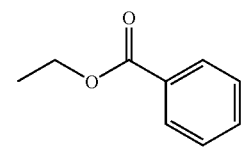 | —O—CH₂CH₃ | —O—Si(CH₃)₂—O—Si(CH₃)₃ | —CH₂CH₃ | —H |
| ethyl cyclohexanecarboxylate group 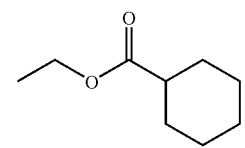 | —O—CH₂CH₃ | —O—Si(CH₃)₂—O—Si(CH₃)₃ | —CH₂CH₃ | —H |
| ethyl acetate group 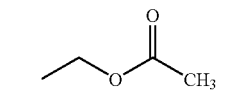 | —O—CH₂CH₃ | —O—Si(CH₃)₂—O—Si(CH₃)₃ | —CH₂CH₃ | —H |
| ethyl succinate group 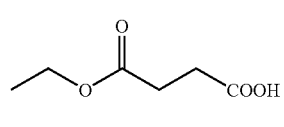 | —O—CH₂CH₃ | —O—Si(CH₃)₂—O—Si(CH₃)₃ | —CH₂CH₃ | —H |
| ethyl nicotinate group 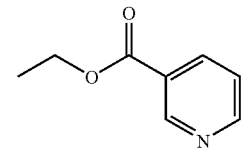 | —O—CH₂CH₃ | —O—Si(CH₃)₂—O—Si(CH₃)₃ | —CH₂CH₃ | —H |
| —CH=N—NH—(2,4-dinitrophenyl) 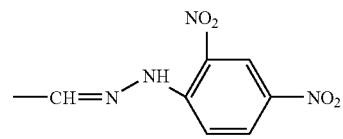 | —O—CH₂CH₃ | —O—Si(CH₃)₂—O—Si(CH₃)₃ | —CH₂CH₃ | —H |

-continued
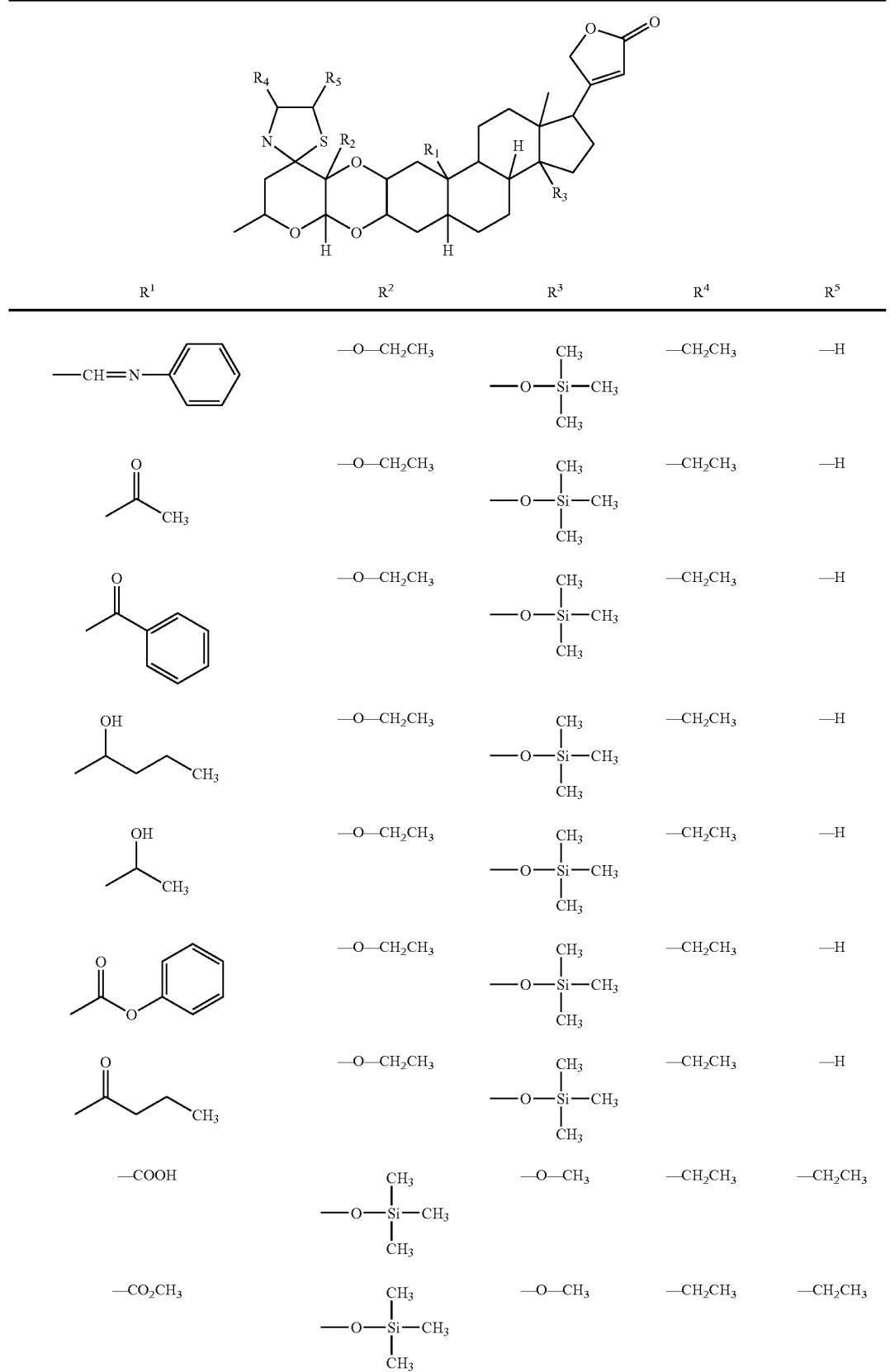

-continued

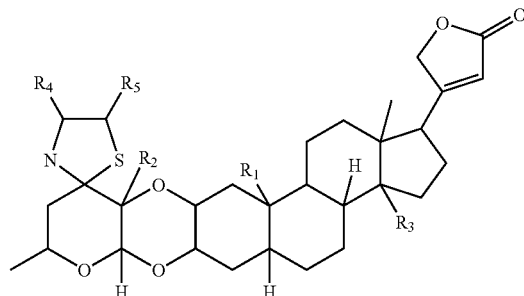

| R¹ | R² | R³ | R⁴ | R⁵ |
|---|---|---|---|---|
| —CO₂C₂H₅ | —O—Si(CH₃)₃ | —O—CH₃ | —CH₂CH₃ | —CH₂CH₃ |
| —CHO | —O—Si(CH₃)₃ | —O—CH₃ | —CH₂CH₃ | —CH₂CH₃ |
| —CH₂OH | —O—Si(CH₃)₃ | —O—CH₃ | —CH₂CH₃ | —CH₂CH₃ |
| —CHOHCH₃ | —O—Si(CH₃)₃ | —O—CH₃ | —CH₂CH₃ | —CH₂CH₃ |
| —CH₂—CH=CH₂ | —O—Si(CH₃)₃ | —O—CH₃ | —CH₂CH₃ | —CH₂CH₃ |
| —COOCH₃ | —O—Si(CH₃)₃ | —O—CH₃ | —CH₂CH₃ | —CH₂CH₃ |
| —CH₂OCH₃ | —O—Si(CH₃)₃ | —O—CH₃ | —CH₂CH₃ | —CH₂CH₃ |
| —CH₂OCH₂CH₃ | —O—Si(CH₃)₃ | —O—CH₃ | —CH₂CH₃ | —CH₂CH₃ |
| —CH₂SCH₃ | —O—Si(CH₃)₃ | —O—CH₃ | —CH₂CH₃ | —CH₂CH₃ |
| —CH=N—OH | —O—Si(CH₃)₃ | —O—CH₃ | —CH₂CH₃ | —CH₂CH₃ |

-continued

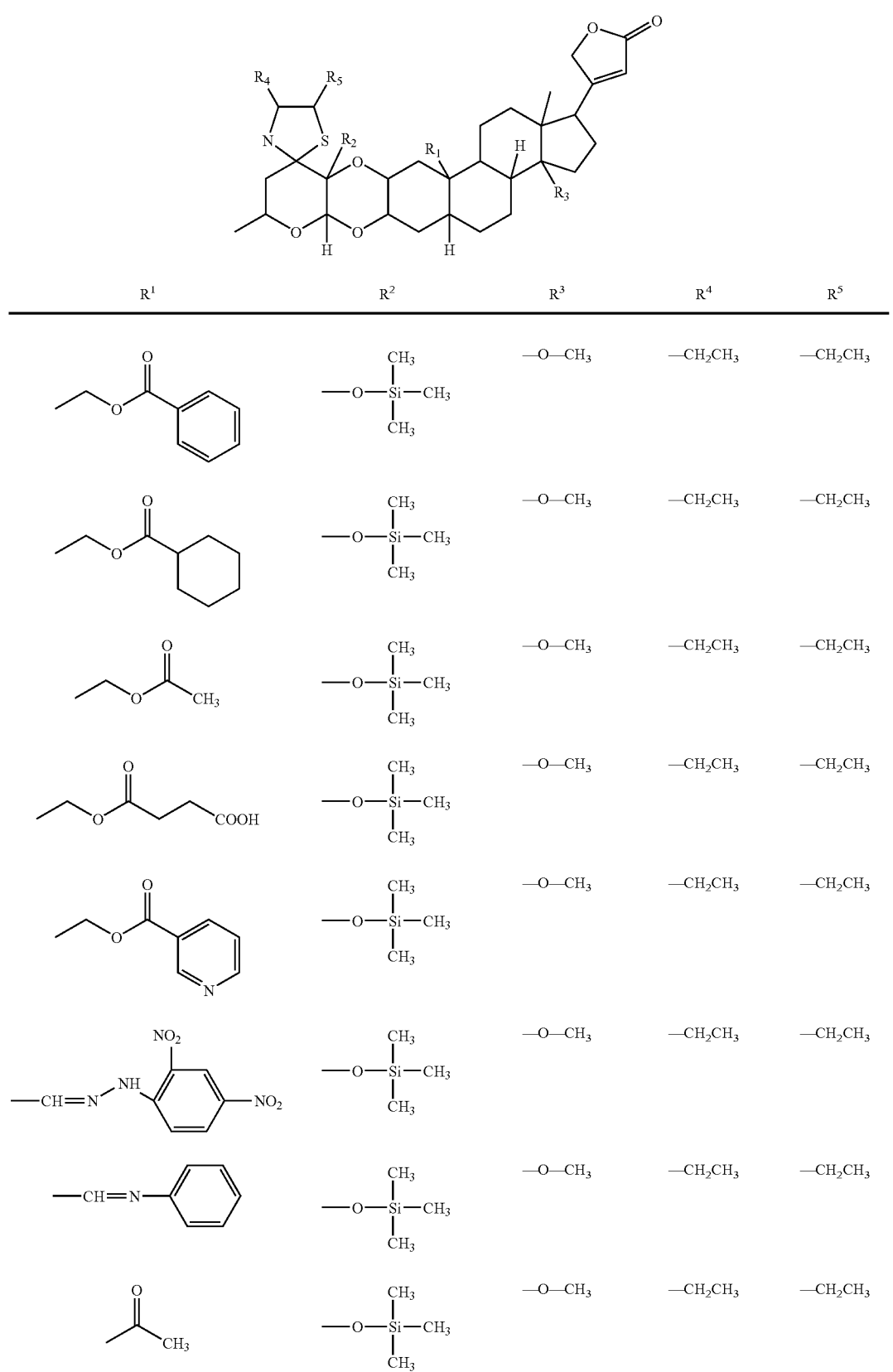

| R¹ | R² | R³ | R⁴ | R⁵ |
|---|---|---|---|---|
| ethyl benzoate | —O—Si(CH₃)₃ | —O—CH₃ | —CH₂CH₃ | —CH₂CH₃ |
| ethyl cyclohexanecarboxylate | —O—Si(CH₃)₃ | —O—CH₃ | —CH₂CH₃ | —CH₂CH₃ |
| ethyl acetate | —O—Si(CH₃)₃ | —O—CH₃ | —CH₂CH₃ | —CH₂CH₃ |
| ethyl succinate (COOH) | —O—Si(CH₃)₃ | —O—CH₃ | —CH₂CH₃ | —CH₂CH₃ |
| ethyl nicotinate | —O—Si(CH₃)₃ | —O—CH₃ | —CH₂CH₃ | —CH₂CH₃ |
| —CH=N—NH—(2,4-dinitrophenyl) | —O—Si(CH₃)₃ | —O—CH₃ | —CH₂CH₃ | —CH₂CH₃ |
| —CH=N—phenyl | —O—Si(CH₃)₃ | —O—CH₃ | —CH₂CH₃ | —CH₂CH₃ |
| acetyl (CH₃C(O)—) | —O—Si(CH₃)₃ | —O—CH₃ | —CH₂CH₃ | —CH₂CH₃ |

-continued

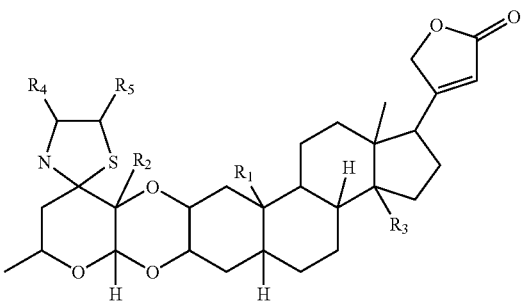

| R¹ | R² | R³ | R⁴ | R⁵ |
|---|---|---|---|---|
| acetophenone group | —O—Si(CH₃)₃ | —O—CH₃ | —CH₂CH₃ | —CH₂CH₃ |
| 2-hydroxypentyl | —O—Si(CH₃)₃ | —O—CH₃ | —CH₂CH₃ | —CH₂CH₃ |
| 2-hydroxypropyl | —O—Si(CH₃)₃ | —O—CH₃ | —CH₂CH₃ | —CH₂CH₃ |
| phenyl acetate | —O—Si(CH₃)₃ | —O—CH₃ | —CH₂CH₃ | —CH₂CH₃ |
| 2-oxobutyl | —O—Si(CH₃)₃ | —O—CH₃ | —CH₂CH₃ | —CH₂CH₃ |
| —COOH | —OH | —OH | Double bond* | —H |
| —CO₂CH₃ | —OH | —OH | Double bond* | —H |
| —CO₂C₂H₅ | —OH | —OH | Double bond* | —H |
| —CH₂OH | —OH | —OH | Double bond* | —H |
| —CHOHCH₃ | —OH | —OH | Double bond* | —H |
| —CH₂—CH₂—CH=CH₂ | —OH | —OH | Double bond* | —H |
| —COOCH₃ | —OH | —OH | Double bond* | —H |
| —CH₂OCH₃ | —OH | —OH | Double bond* | —H |
| —CH₂OCH₂CH₃ | —OH | —OH | Double bond* | —H |
| —CH₂SCH₃ | —OH | —OH | Double bond* | —H |
| —CH=N—OH | —OH | —OH | Double bond* | —H |
| ethyl benzoate | —OH | —OH | Double bond* | —H |
| ethyl cyclohexanecarboxylate | —OH | —OH | Double bond* | —H |

-continued

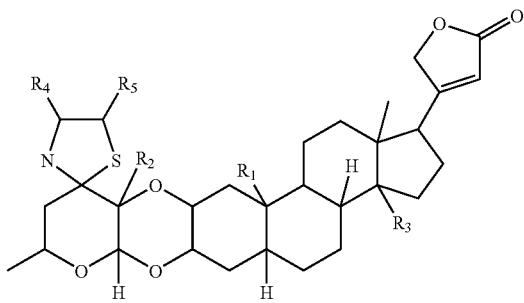

| R¹ | R² | R³ | R⁴ | R⁵ |
|---|---|---|---|---|
| —O—CH₂—C(=O)—CH₃ (ethyl acetate group) | —OH | —OH | Double bond* | —H |
| —O—CH₂—CH₂—C(=O)—CH₂—COOH (ethyl succinate) | —OH | —OH | Double bond* | —H |
| ethyl nicotinate group | —OH | —OH | Double bond* | —H |
| —CH=N—NH—(2,4-dinitrophenyl) | —OH | —OH | Double bond* | —H |
| —CH=N—phenyl | —OH | —OH | Double bond* | —H |
| —C(=O)—CH₃ | —OH | —OH | Double bond* | —H |
| —C(=O)—phenyl | —OH | —OH | Double bond* | —H |
| —CH(OH)—CH₂—CH₂—CH₃ (with methyl) | —OH | —OH | Double bond* | —H |
| —CH(OH)—CH₃ | —OH | —OH | Double bond* | —H |
| —O—C(=O)—CH₂—phenyl | —OH | —OH | Double bond* | —H |

-continued

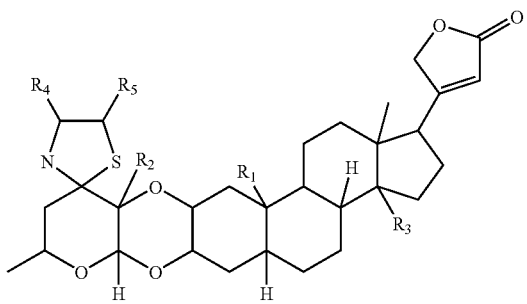

| R¹ | R² | R³ | R⁴ | R⁵ |
|---|---|---|---|---|
| ![pentanone group] (CH₃COCH₂CH₂CH₃-like) | —OH | —OH | Double bond* | —H |
| —H | —OH | —OH | =O | —H |
| —CO₂C₂H₅ | —OH | —OH | —CH₂OH | —H |
| —COH | —OH | —OH | —C₂H₄OH | —H |
| —O—CH₃ | —OH | —OH | —CH₃ | —H |
| —O—C₂H₅ | —OH | —OH | —C₂H₅ | —H |
| —CO₂H | —OH | —OH | —CH=CH₂ | —H |
| —OH | —OH | —OH | —CH₂—CH=CH₂ | —H |
| —CH₂OH | —OH | —OH | —CH(CH₃)CH₃ (isopropyl) | —H |
| —C₂H₄OH | —OH | —OH | —CH₂CH₂CH(CH₃)CH₃ | —H |
| —CH₃ | —OH | —OH | —CH₂CH=C(CH₃)CH₃ | —H |
| —OH | —OH | —OH | ethyl propyl ketone (CH₃CH₂—CO—CH₂CH₂CH₃) | —H |
| —OH | —OH | —OH | ethyl propyl ketone (CH₃CH₂—CO—CH₂CH₂CH₃) | —H |
| —OH | —OH | —OH | propiophenone (C₆H₅—CO—CH₂CH₃) | —H |
| —COOH | —OH | —OH | propiophenone (C₆H₅—CO—CH₂CH₃) | —H |

-continued
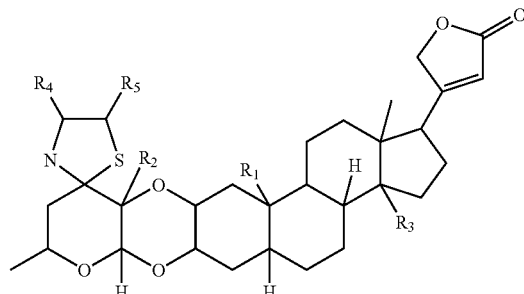
| R¹ | R² | R³ | R⁴ | R⁵ |
|---|---|---|---|---|
| —CO₂CH₃ | —OH | —OH | C(=O)CH₂CH₂-phenyl | —H |
| —CO₂C₂H₅ | —OH | —OH | C(=O)CH₂CH₂-phenyl | —H |
| —CHO | —OH | —OH | C(=O)CH₂CH₂-phenyl | —H |
| —CH₂OH | —OH | —OH | C(=O)CH₂CH₂-phenyl | —H |
| —CHOHCH₃ | —OH | —OH | C(=O)CH₂CH₂-phenyl | —H |
| —CH₂—CH₂—CH=CH₂ | —OH | —OH | C(=O)CH₂CH₂-phenyl | —H |
| —COOCH₃ | —OH | —OH | C(=O)CH₂CH₂-phenyl | —H |
| —CH₂OCH₃ | —OH | —OH | C(=O)CH₂CH₂-phenyl | —H |

-continued
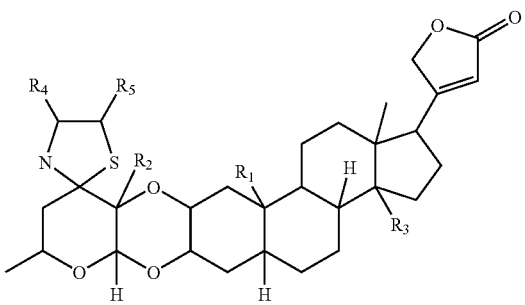
| R¹ | R² | R³ | R⁴ | R⁵ |
|---|---|---|---|---|
|  —CH₂OCH₂CH₃ | —OH | —OH | 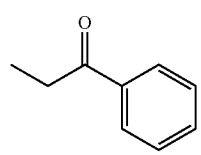 | —H |
|  —CH₂SCH₃ | —OH | —OH | 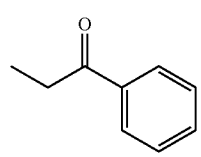 | —H |
| 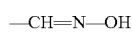 —CH=N—OH | —OH | —OH | 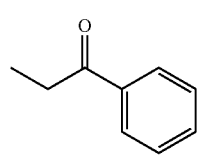 | —H |
| 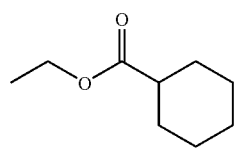 | —OH | —OH | 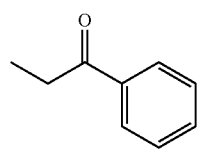 | —H |
| 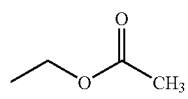 | —OH | —OH | 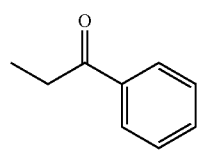 | —H |
| 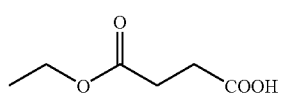 | —OH | —OH | 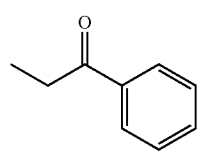 | —H |
| 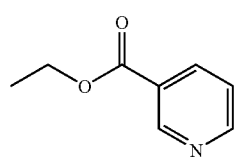 | —OH | —OH | 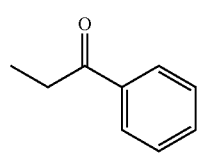 | —H |

-continued
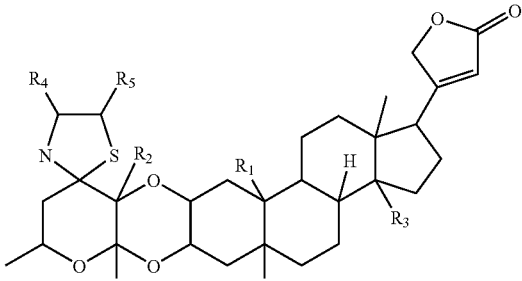
| R¹ | R² | R³ | R⁴ | R⁵ |
|---|---|---|---|---|
| 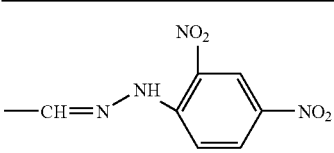 | —OH | —OH | 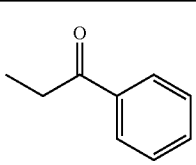 | —H |
| 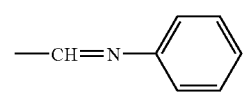 | —OH | —OH | 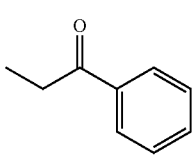 | —H |
| 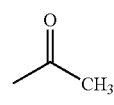 | —OH | —OH | 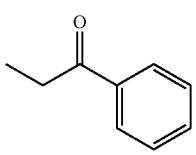 | —H |
| 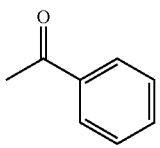 | —OH | —OH | 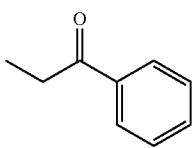 | —H |
| 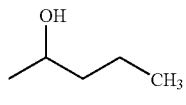 | —OH | —OH | 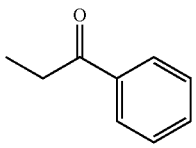 | —H |
| 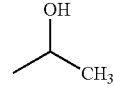 | —OH | —OH | 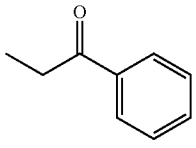 | —H |
| 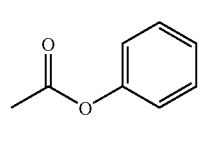 | —OH | —OH | 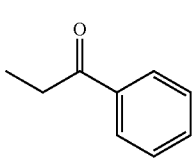 | —H |

-continued

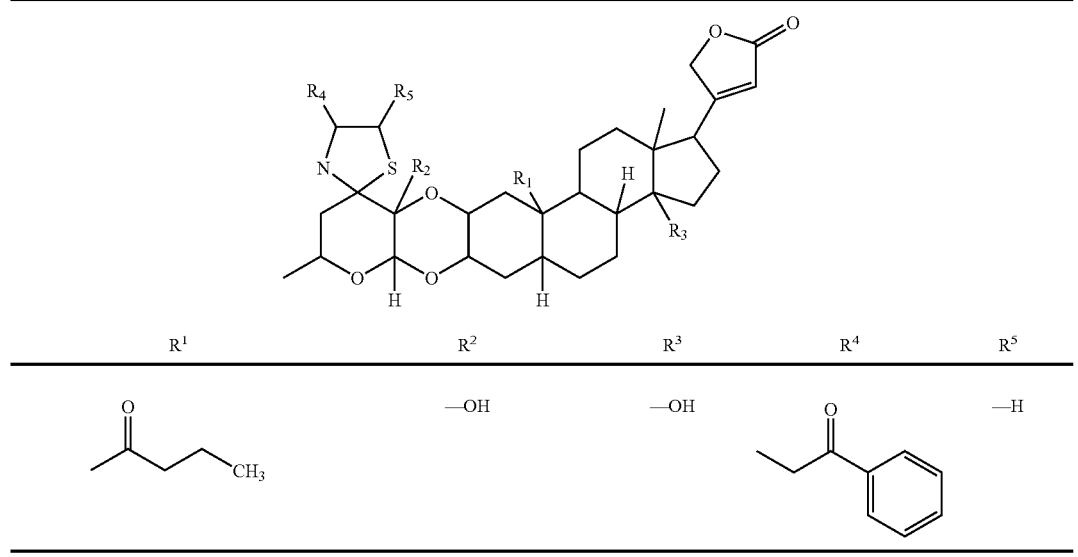

*means a double bond between the N atom and the C carbon atom of the N-containing heterocyclic ring of formula I

Example 2

Preparation of Different Compounds According to the Invention

The following example illustrates the preparation of eight derivatives according to the invention. These compounds are represented in the table B below.

TABLE B

Compounds according to the invention

| | $R_1$ | $R_2$ | $R_3$ | $R_4$ | $R_5$ |
|---|---|---|---|---|---|
| 2″oxo-voruscharin | —COH | —OH | —OH | =O | —H |
| Compound B | —CH$_2$OH | —OH | —OH | =O | —H |
| Compound C | —CH$_2$OAc | —OH | —OH | =O | —H |
| Compound F | —CH$_2$OOCphenyl | —OH | —OH | =O | —H |
| Compound D | —CH$_2$OH | —OH | —OH | Double bond* | —H |
| Compound E | —CH$_2$OAc | —OH | —OH | Double bond* | —H |
| Compound G | —CH$_2$OOCphenyl | —OH | —OH | Double bond* | —H |
| Compound H | —CH$_2$OH | —OH | —OH | (benzoyl group) | —H |
| Compound I | —CH$_2$OH | —OH | —OH | (benzoyl group) | —H |

*means a double bond between the N atom and the C carbon atom of the N-containing heterocyclic ring of formula I.

2″oxo-voruscharin was isolated from *Calotropis procera*. First the leaf blades, stems, barks and roots of the plant were ground into a fine powder. The powder was then extracted with dichloromethane for at least 6, 12, 18 or preferably 24 hours using a soxhlet extractor. The dichloromethane phase was decanted and filtrated using a fritted glass of porosity no 3. The filtrate was evaporated and a dry extract was obtained. The dry extract was suspended in hexane and magnetically stirred at room temperature for at least 12 to 16 hours. The suspension in hexane was then decanted and filtrated with fritted glass of porosity no 3. The insoluble part was then extracted with methanol for at least 6, 12 to 16 hours, and the mixture was fitrated with fritted glass of porosity no 3. The insoluble part of the mixture was then subjected to column chromatography using C18 grafted flash silica gel using a binary eluent methanol/water in proportion varying from 50:50 to 80:20.

Biological activity was observed in the fractions wherein the binary eluent proportions were comprised between 60:40 and 70:30. These fractions were evaporated to dryness and further subjected to flash chromatography on silica gel using as binary eluent dichloromethane/methanol, which permitted the isolation of two pure compounds: 2"oxo-voruscharin and uscharin.

In order to prepare compound B, 5 eq. of $NaBH_4$ (7.5 mg, $1.98\ 10^{-4}$ mol were added to a magnetically stirred solution of 23.9 mg of 2"oxo-voruscharin ($0.39\ 10^{-4}$ mol) in 2 ml of methanol. The mixture was stirred for 1 hour. The solvent was then evaporated under reduced pressure. A flash chromatography on silica gel ($CH_2Cl_2$; $CH_2Cl_2$/MeOH: 95/5) of the crude product provided 15.9 mg of compound B. The yield of this preparation process comprised 66%.

Another derivative consisted of compound C. This compound was prepared by acetylation of compound B, described above. A solution of 3.04 mg of compound B ($5.0\ 10^{-6}$ mol) in 1 ml of a mixture 50/50 acetic anhydride/pyridine was stirred for 1 hour 20 minutes at room temperature. 1 ml of water was subsequently added at 0° C. under stirring. After 15 minutes, the solvent was evaporated under reduced pressure. A flash chromatography on silica gel ($CH_2Cl_2$/MeOH: 9/1) of the crude product provided 3.00 mg of compound C. The yield of this preparation process comprised 92%.

Compound F was prepared by benzoylation of compound B. A solution of 10.05 mg of compound B ($1.66\ 10^{-5}$ mole) and 0.5 ml of pyridine was magnetically stirred and 5 drops of benzoyl chloride were stirred for 25 minutes. The residue was taken up with water and extracted with dichloromethane. After separation, the organic layer was evaporated under vacuum. A flash chromatography on silica gel ($CH_2Cl_2$, $CH_2Cl_2$/MeOH: 99:1, 98:2, 97:3, 96:4) of the crude product provided 8.13 mg of Compound F. The yield of this preparation process comprised 69%.

The compound D was prepared by adding 5.5 eq. of $NaBH_4$ (16.8 mg, $4.44\ 10^{-4}$ mol) to a magnetically stirred solution of 47 mg of uscharin ($0.80\ 10^{-4}$ mol) in 3 ml of methanol. The mixture was stirred for 10 minutes. The solvent was then evaporated under reduced pressure. A flash chromatography on silica gel ($CH_2Cl_2$; $CH_2Cl_2$/MeOH: 95:5) of the crude product provided 31.5 mg of compound D. The yield of this preparation process comprised 67%.

Another hemisynthetic derivative consisted of compound E. This compound was prepared by acetylation of compound D. A solution of 6.09 mg of compound D ($0.10\ 10^{-4}$ mol) in 2 ml of a mixture 50/50 acetic anhydride/pyridine was stirred for 2 hours at room temperature. 2 ml of water was added at 0° C. under stirring. After 15 minutes, the solvent was evaporated under reduced pressure. A flash chromatography on silica gel ($CH_2Cl_2$/MeOH: 9/1) of the crude product provided 5.86 mg of compound E. The yield of this preparation process comprised 90%.

Compound G was prepared by benzoylation of compound D. A solution of 15.13 mg of compound D ($2.57\ 10^{-5}$ mole) and 0.5 ml of pyridine was magnetically stirred, and 5 drops of benzoyl chloride were stirred for 15 minutes. The residue was taken up with water and extract with dichloromethane. After separation, the organic layer was evaporated under vacuum. A flash chromatography on silica gel ($CH_2Cl_2$, $CH_2Cl_2$/MeOH: 9/1) of the crude product provided 12.5 mg of compound G. The yield of this preparation process comprised 70%.

Compound H and I were prepared using compound D as a starting material according to scheme 1:

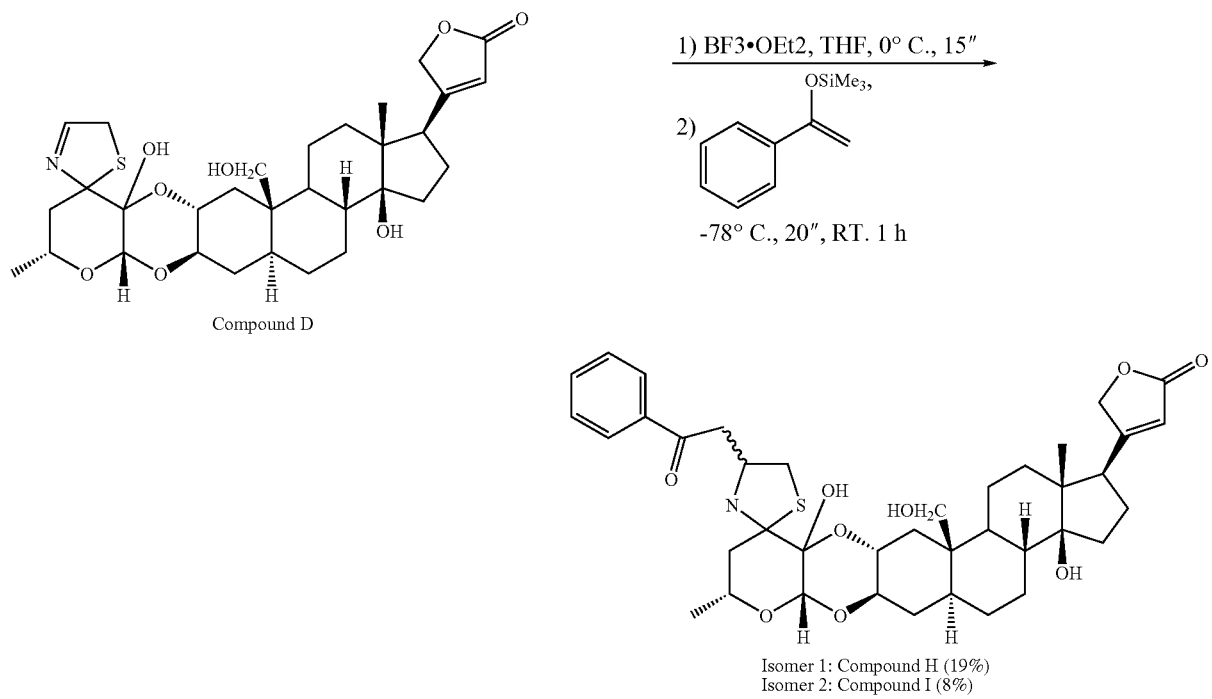

In 2 ml of THF were successively added, 37.3 mg of compound D (589 g/mol, 63.3 $10^{-6}$ mole) and 30 μl of $BF_3.Et_2O$ (141.9 g/mol, 3 eq). The mixture was stirred at 0° C. under $N_2$. After 30 minutes, the mixture was cooled to −78° C. A solution of 75.0 mg of 1-phenyl-1(trimethylsilyloxy)ethylene (4 eq) in 0.5 ml of THF was finally added. The reaction mixture was stirred at −78° C. for 20 minutes and then at room temperature for 1 hour. After neutralization of the solution with a 1N solution of $NaHCO_3$, the mixture was extracted with dichloromethane and the organic layer was evaporated under vacuum. The 2 isomers, compound H and compound I, were isolated by flash chromatography on silica gel ($SiO_2$, length=20 cm, diameter=1 cm, gradient of elution: $CH_2Cl_2$, $CH_2Cl_2$/MeOH 99:1, 98:2). 8.4 mg (709 g/mol) of the pure compound H were obtained (yield=19%) and 3.5 mg (709 g/mol) of compound I were obtained (yield=8%). In addition, 3.3 mg (709 g/mol) of a mixture of compounds H and I were isolated (yield=7%). The global yield of this process was 34% for the 2 isomers. The obtained isomers were analysed by IR spectroscopy and by proton NMR spectrometry.

Example 3

Effect of Different Compounds According to the Invention on Overall Cell Growth of a Cell Line In order to characterize the in vitro activities of the compounds according to the invention, MTT tests were carried out. The MTT test, which is a well-known test in the art, is an indirect technique that rapidly measures, i.e. within 5 days, the effect of a given product on the overall cell growth. This test measures the number of metabolically active living cells that are able to transform the MTT product (3-(4,5-dimethylthiazol-2-yl)-2,5 diphenyl tetrazolium bromide), having a yellowish color, to the blue product formazan dye by mitochondrial reduction. The amount of formazan obtained at the end of the experiment is measured with a spectrophotometer and is directly proportional to the number of living cells. Determination of the optical density enables a quantitative measurement of the effect of the investigated compounds as compared to the control condition (untreated cells) and to compare it to other reference compound. In the following examples different compounds according to the invention were tested and compared to the reference compound being uscharin.

Six human cancer cell lines, described in Table C, were tested in the presence of compounds according to the invention. These cell lines covered four histological cancer types, being Glioma, colon, lung and bladder cancer. The cells were allowed to grow in 96-well micro wells with a flat bottom with an amount of 100 μl of cell suspension per well in reason to 4000 cells/well depending on cell type. Each cell line was seeded in its own cell culture medium (Table C).

TABLE C

Human cancer cell lines and corresponding cell culture medium used for the MTT experiments

| Cell lines | ATCC code | Tissue | Medium | Literature Ref. |
|---|---|---|---|---|
| Hs683 | HTB-138 | Glioma | MEM 5% serum | J. Natl. Cancer Inst. 56: 843-849, 1976; ibid. 58: 1455-1463, 1977 |
| U-373 MG | HTB-17 | Glioma | MEM 5% serum | Acta Pathol. Microbial. Scand. 74: 465-486, 1968 |
| HCT-15 | CCL-225 | Colon | MEM 5% serum | Cancer Res. 39: 1020-1025, 1979 |
| LoVo | CCL-229 | Colon | MEM 5% serum | Exp. Cell Res: 101: 414-416, 1976; J. Natl. Cancer Inst. 61: 75-83, 1978; Cancer Res. 39: 2630-2636, 1979 |
| A549 | CCL-185 | Lung | MEM 5% serum | J. Natl. Cancer Inst. 51: 1417-1423, 1973; Int. J. Cancer 17: 62-70, 1976 |
| J82 | HTB-1 | Bladder | MEM 5% serum | Br. J. Cancer 38: 64-76, 1978; In Vitro models for cancer research Vol iV. CRC Press, 103-125, 1986 |

After a 24-hour period of incubation at 37° C., the culture medium is replaced by 100 μl of fresh medium in which the compound to be tested has been dissolved at different required concentrations. Different compounds were tested at $10^{-9}$ M, $5 \times 10^{-9}$ M, $10^{-8}$ M, $5 \times 10^{-8}$ M, $10^{-7}$ M, $5 \times 10^{-7}$ M, $10^{-6}$ M, $5 \times 10^{-6}$ M et $10^{-5}$ M. Each experimental condition is carried out in hexaplicate. The compounds tested are 2″ oxo-voruscharin, and compounds B, C, D, E, H and I represented in Table B above.

After 72 hours of incubation at 37° C. with the compound (experimental conditions) or without the compound (control condition), the medium was replaced by 100 μl MTT at the concentration of 1 mg/ml dissolved in RPMI. The micro wells were subsequently incubated during 3 hours at 37° C. and centrifuged at 400 g during 10 minutes. The MTT was removed and formazan crystals formed, were dissolved in 100 μl DMSO. The micro wells were shaken for 5 minutes and read on a spectrophotometer at the wavelengths of 570 nm corresponding to the maximum formazan absorbance wavelength, and of 630 nm, which is the background noise wavelength.

For each experimental condition, the mean OD associated with the SEM (standard error of the mean) for each condition (6 wells) was calculated. The percentage of remaining living cells in comparison with the control was calculated. Results of these experiments are represented in FIGS. 2 to 8.

FIG. 1 represents the anti-tumor activity of the known compound uscharin on 5 of the 6 tested cell lines (see Table D). The human tumor cell line issued from bladder (J82) showed a weaker sensitivity to uscharin.

As illustrated on FIG. 2 to 8 the compounds according to the invention also exerted an anti-tumor activity for 5 of the 6 tested cell lines. Only the human tumor cell lines issued from bladder presented weaker sensitivity to the 6 compounds than the remaining 5 cell lines. Among the 7 compounds, the compounds C and E presented the weakest cytotoxic activity.

The concentration at which the compounds according to the invention kill 50% of cell population, i.e. the $IC_{50}$ value, is represented in Table D.

TABLE D

Comparison of the $IC_{50}$ value of uscharin with that of the compounds according to the invention

|  | Hs683 | U-373 | HCT-15 | LoVo | A549 | J82 |
|---|---|---|---|---|---|---|
| uscharin | $5 \times 10^{-9}$-$10^{-9}$ | $5 \times 10^{-8}$-$10^{-8}$ | $5 \times 10^{-8}$-$10^{-8}$ | $10^{-8}$-$5 \times 10^{-9}$ | $5 \times 10^{-8}$-$10^{-8}$ | $10^{-5}$-$5 \times 10^{-6}$ |
| 2"oxo-voruscharin | $5 \times 10^{-9}$-$10^{-9}$ | $5 \times 10^{-8}$-$10^{-8}$ | $5 \times 10^{-8}$-$10^{-8}$ | $10^{-8}$-$5 \times 10^{-9}$ | $5 \times 10^{-8}$-$10^{-8}$ | >$10^{-5}$ |
| Compound B | $5 \times 10^{-6}$-$10^{-6}$ | $5 \times 10^{-8}$-$10^{-8}$ | $5 \times 10^{-8}$-$10^{-8}$ | $5 \times 10^{-9}$-$10^{-9}$ | $10^{-8}$ | $10^{-5}$-$5 \times 10^{-6}$ |
| Compound C | $5 \times 10^{-8}$-$10^{-8}$ | $5 \times 10^{-6}$-$10^{-6}$ | $5 \times 10^{-6}$-$10^{-6}$ | $5 \times 10^{-6}$-$10^{-6}$ | $5 \times 10^{-6}$-$10^{-6}$ | >$10^{-5}$ |
| Compound D | $5 \times 10^{-9}$-$10^{-9}$ | $5 \times 10^{-6}$-$10^{-6}$ | $5 \times 10^{-8}$-$10^{-8}$ | $5 \times 10^{-9}$-$10^{-9}$ | $5 \times 10^{-8}$-$10^{-8}$ | $10^{-5}$-$5 \times 10^{-6}$ |
| Compound E | $5 \times 10^{-6}$-$10^{-6}$ | $5 \times 10^{-6}$-$10^{-6}$ | $5 \times 10^{-6}$-$10^{-6}$ | $5 \times 10^{-6}$-$10^{-6}$ | $5 \times 10^{-6}$-$10^{-6}$ | >$10^{-6}$ |
| Compound H | $5 \times 10^{-9}$-$10^{-9}$ | $5 \times 10^{-8}$-$10^{-8}$ | $5 \times 10^{-8}$-$10^{-8}$ | $5 \times 10^{-8}$-$10^{-8}$ | $5 \times 10^{-9}$-$10^{-9}$ | $5 \times 10^{-6}$-$10^{-6}$ |
| Compound I | $5 \times 10^{-9}$-$10^{-9}$ | $5 \times 10^{-8}$-$10^{-8}$ | $5 \times 10^{-8}$-$10^{-8}$ | $5 \times 10^{-8}$-$10^{-8}$ | $5 \times 10^{-9}$-$10^{-9}$ | $5 \times 10^{-6}$-$10^{-6}$ |

The $IC_{50}$ values for uscharin and 2"oxo-voruscharin ranged between $5 \times 10^{-8}$ and $10^{-9}$ M depending on the tested cell line except for J82 where the $IC_{50}$ value ranged between $10^{-5}$ and $5 \times 10^{-6}$ M for uscharin and higher than $10^{-5}$ M for 2"oxo-voruscharin (see table D).

The $IC_{50}$ value of uscharin and 2"oxo-voruscharin were 1000 fold lower than the $IC_{50}$ value of compound B for the cell line Hs683. The growth of U-373, HCT-15, LoVo, A549 cell lines was affected in the same way by uscharin, 2"oxo-voruscharin and compounds B, D, H and I. Depending on the cell line, the $IC_{50}$ value of uscharin and 2"oxo-voruscharin was 100 to 1000 fold lower than the $IC_{50}$ value of compounds C, and E. The J82 cell line was the less sensitive than the other tested cell lines.

Figure 5:
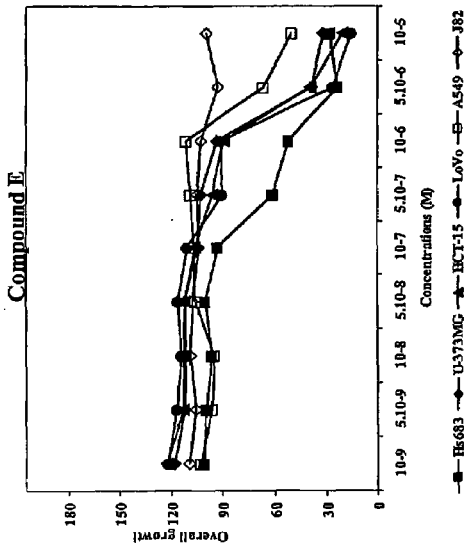
Figure 6:
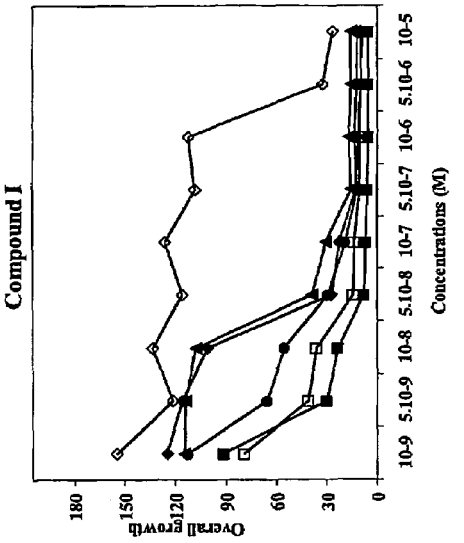
Figure 7:
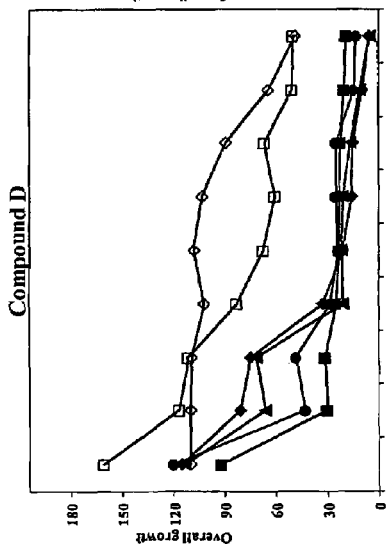
Figure 8:
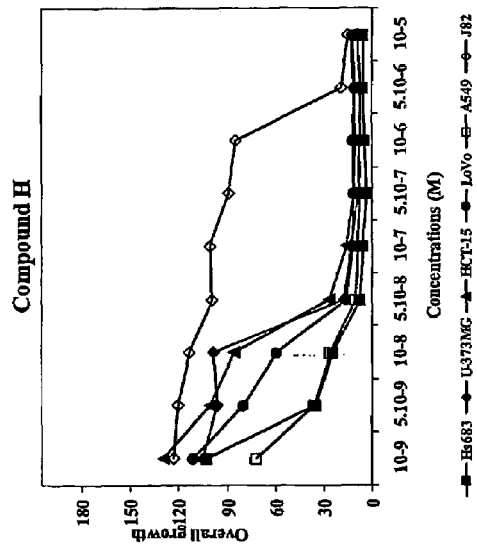
Figure 9:
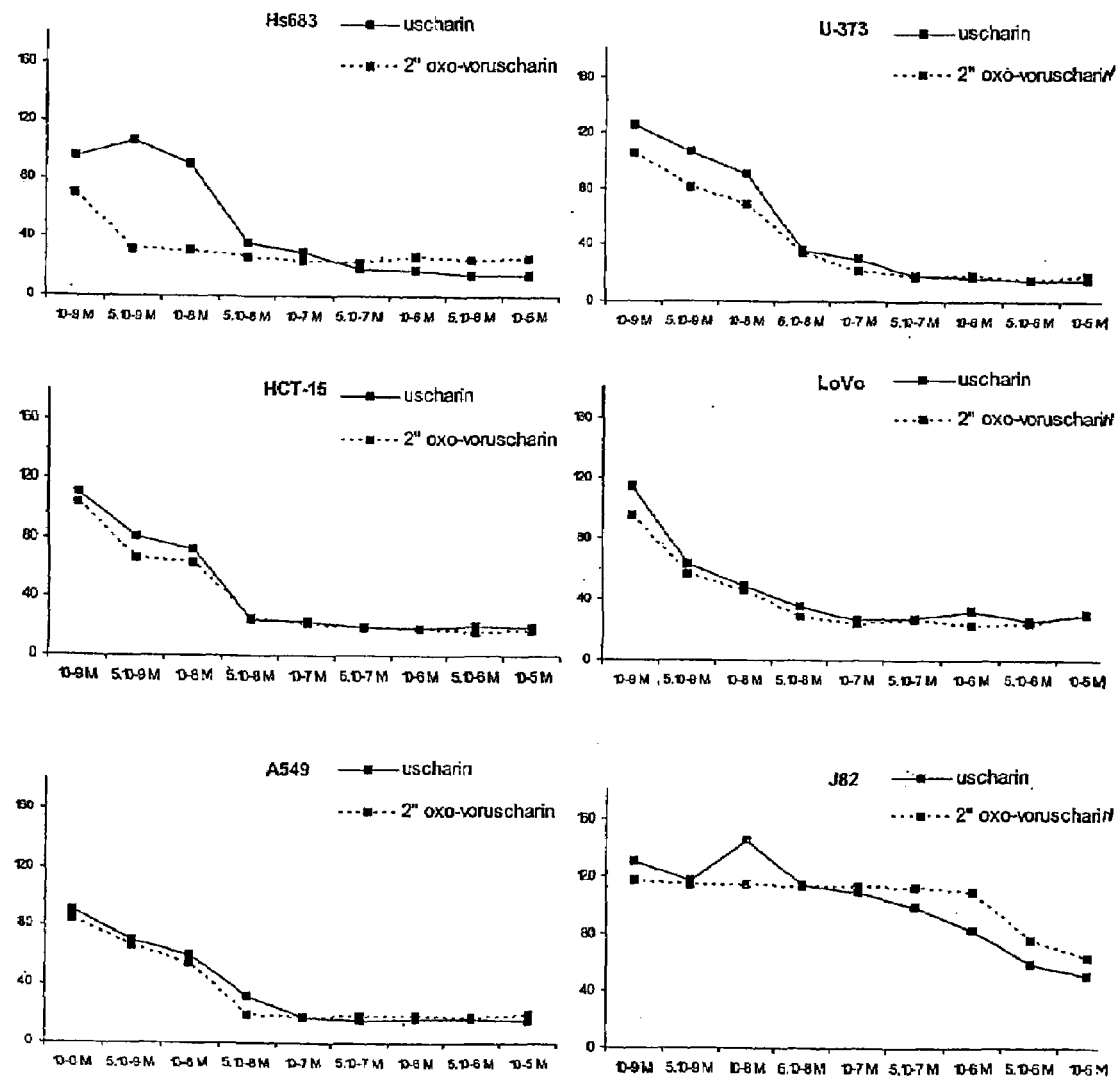
Figure 10:
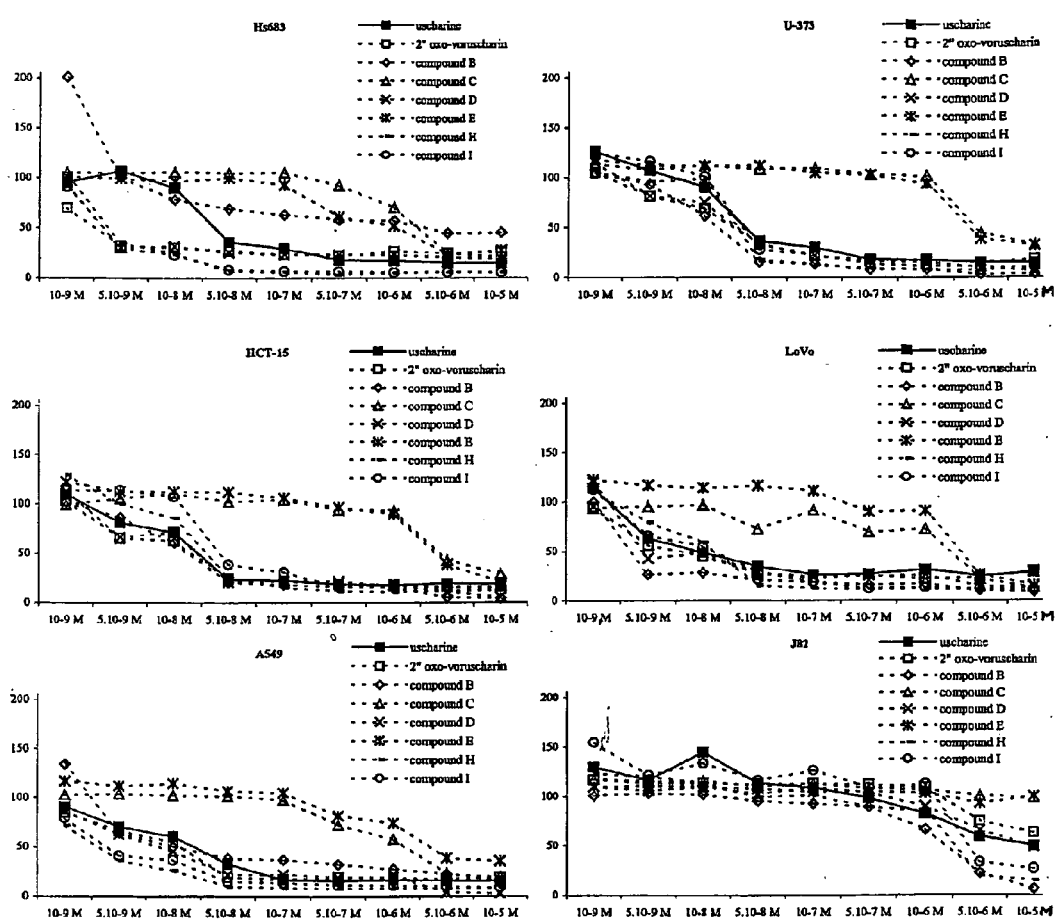

FIG. 9 compares the cytotoxic activity of uscharin and 2"oxo-voruscharin on 6 cell lines. Both compounds induced a similar anti-tumor effect on each tested cell line. The J82 (bladder cancer) cell line was less sensitive than the other cell lines tested. FIG. 10 compares the cytotoxic activity of uscharin, 2"oxo-voruscharin and compounds B, C, D, E, H and I. On Hs683, uscharin and 2"oxo-voruscharin presented a stronger activity than compound B. The growth of U-373, HCT-15, LoVo, A549 cell lines was affected in the same way by uscharin, 2"oxo-voruscharin and compounds B, D, H and I. The J82 cell line was the less sensitive than the other tested cell lines.

In conclusion, the novel compound 2" oxo-voruscharin according to the invention shows dramatic anti-tumor effects on 5 human cancer cell lines assayed in the present experiments. These anti-tumor effects corresponded to marked decreases in the overall growth of these human cancers models belonging to four representative histological types.

Also the uscharin, 2" oxo-voruscharin and compounds B, C, D, E, H and I show anti-tumor activities.

Example 4

Effect of Different Compounds According to the Invention on Cell Kinetics

According to the experiments performed by means of the MTT colorimetric assay described in example 2, it is clear that the compounds according to the invention decrease the overall growth of most of the human cancer cell lines submitted to the MTT assay. In the following example the effect of the compound 2" oxo-voruscharin according to the invention on cell kinetics was tested and compared to the effect of the known compound uscharin.

Cell lines were seeded in flasks (25 cm² area) containing 7 ml of culture medium. After 48 hours incubation at 37° C. the cell culture medium was replaced by a fresh medium in which the substance to be tested had been dissolved at the different concentrations required. Uscharin and 2" oxo-voruscharin were tested at concentrations, which kill 50% and 30% of the cell population, represented by the $IC_{50}$ and $IC_{30}$ values, respectively. After 24 or 72 hours of treatment the cells were harvested in suspension, washed in Phosphate Buffer Saline (PBS) at 4° C. and permeabilized with 70% ethanol (at 4° C.) overnight at −20° C. The cells were then washed with PBS and incubated with propidium iodide solution (80 μg/ml) for 30 minutes at 37° C. and afterward at 4° C. overnight. Ribonuclease A (3% V/V) was added to the PI solution to break doubled-stranded RNA. The portrait of the cell cycle was established for each sample. Software incorporated into the flow cytometer was used to define precisely the percentage of cells in the different cell cycle phases. Each cell cycle phase was reported in terms of peak surface and calculated as a percentage. The surface of the entire cell cycle was 100%. Each experiment was carried out 3 times. The mean percentage of each different phase and the standard error of the related mean were calculated. Each cell cycle phase of a given condition was compared with the same cell cycle phase of control. The non-treated cells constituted control.

Uscharin and 2" oxo-voruscharin are highly toxic to human tumor cell lines. The concentrations used in the flow cytometry experiments were chosen in accordance with the MTT results (example 2). Three human cancer cell lines, Hs683, J82, and HCT-15 were tested and doses that killed 30 and 50 percent of the cells were applied to investigate whether uscharin and 2" oxo-voruscharin promoted an accumulation in one of the cell cycle phases when the cell cultures were treated for 24 or 72 hours with increasing concentrations of the compounds. The $IC_{50}$ and $IC_{30}$ values for uscharin and 2" oxo-voruscharin corresponding to the three tested cell lines are represented in Table E.

TABLE E $IC_{50}$ and $IC_{30}$ values for uscharin and 2" oxo-voruscharin with respect to three human cancer cell lines

|  | Uscharin | | 2"oxo-voruscharin | |
|---|---|---|---|---|
| Cell lines | $IC_{50}$ | $IC_{30}$ | $IC_{50}$ | $IC_{30}$ |
| Hs683 | $1.7 \times 10^{-7}$ M | $4.3 \times 10^{-8}$ M | $1.7 \times 10^{-7}$ M | $8.3 \times 10^{-9}$ M |
| J82 | $4.3 \times 10^{-6}$ M | $1.7 \times 10^{-8}$ M | $4.1 \times 10^{-6}$ M | $1.7 \times 10^{-6}$ M |
| HCT-15 | $4.3 \times 10^{-8}$ M | $8.5 \times 10^{-9}$ M | $1.2 \times 10^{-8}$ M | $4.1 \times 10^{-9}$ M |

Analysis of Hs683 cells treated with uscharin (FIG. 11) showed an accumulation of cells in S-phase when the Hs683 were treated with uscharin at $1.7 \times 10^{-7}$ M for 24 and 72 hours. This effect was statistically significant. A significant accumulation in G2/M-phase was observed when the cells were treated with uscharin at $1.7 \times 10^{-7}$ M for 24 hours. 2"Oxo-voruscharin induced an accumulation in G2/M phase at $8.3 \times 10^{-9}$ M after 24 hours of treatment and at both concentrations for the 72 hours-treatment (FIG. 12). These effects were significant.

Figure 13:
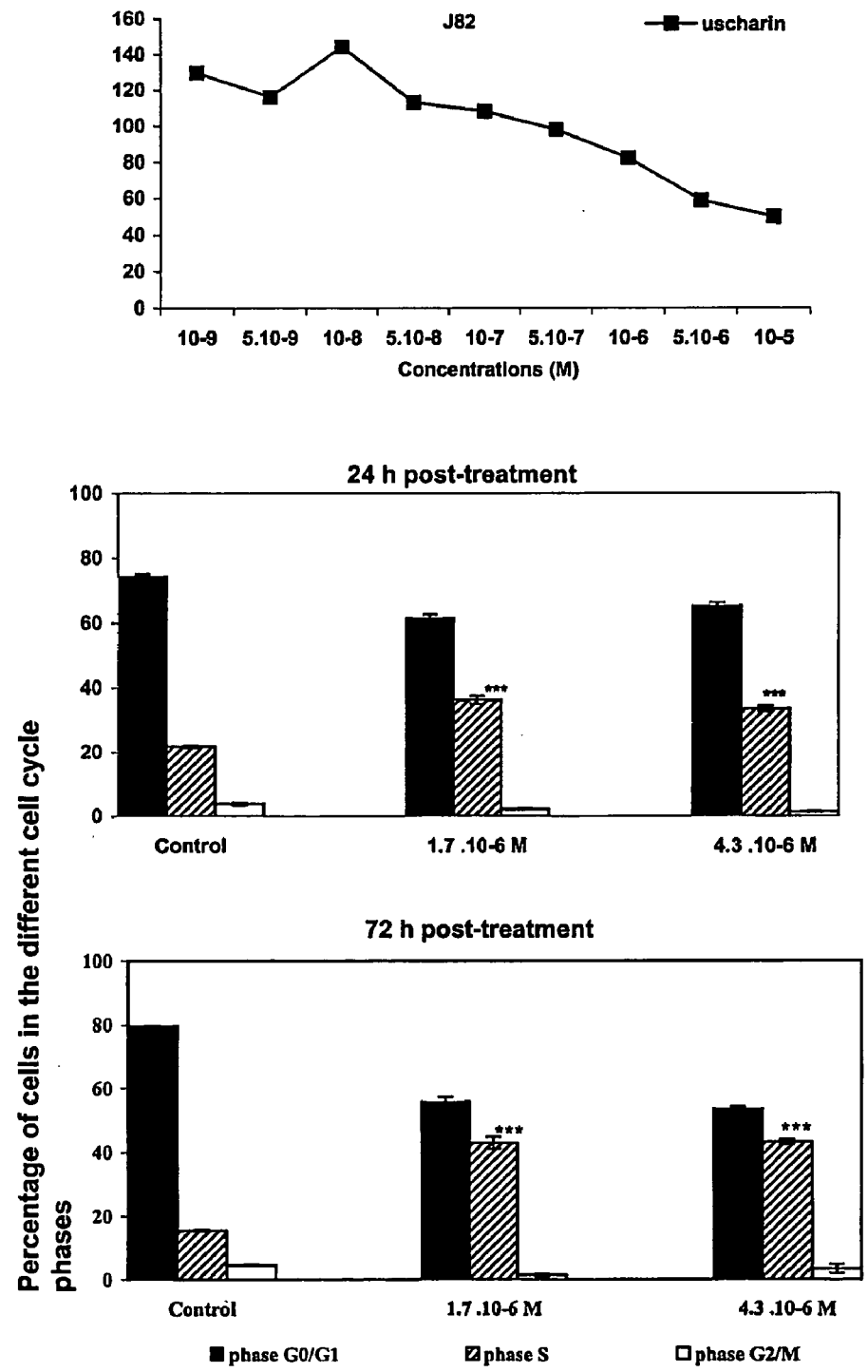
FIGS. 13 and 14 represent the effects of the compound uscharin and 2″ oxo-voruscharin, respectively, on the cell cycle kinetics of J82 human cancer cells.
Figure 14:
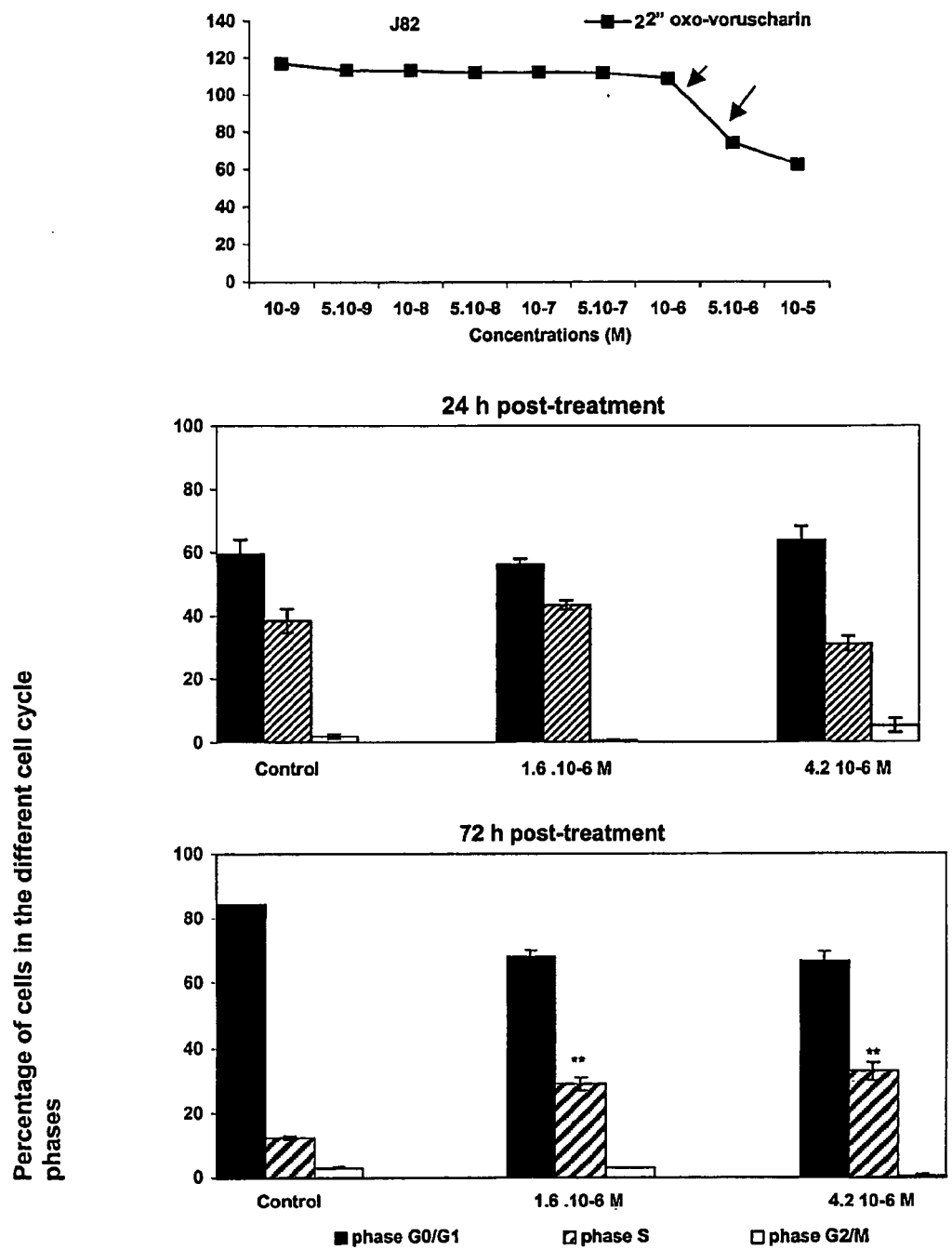

The analyses of cell cycle of the J82 cells treated with uscharin (FIG. 13) showed that, a significant increase in the S-population occurred independent of the concentrations applied or the timing of treatment. 2"oxo-voruscharin induced an increase of S-population only after 72 hours of treatment at both concentrations tested (FIG. 14).

Figure 15:
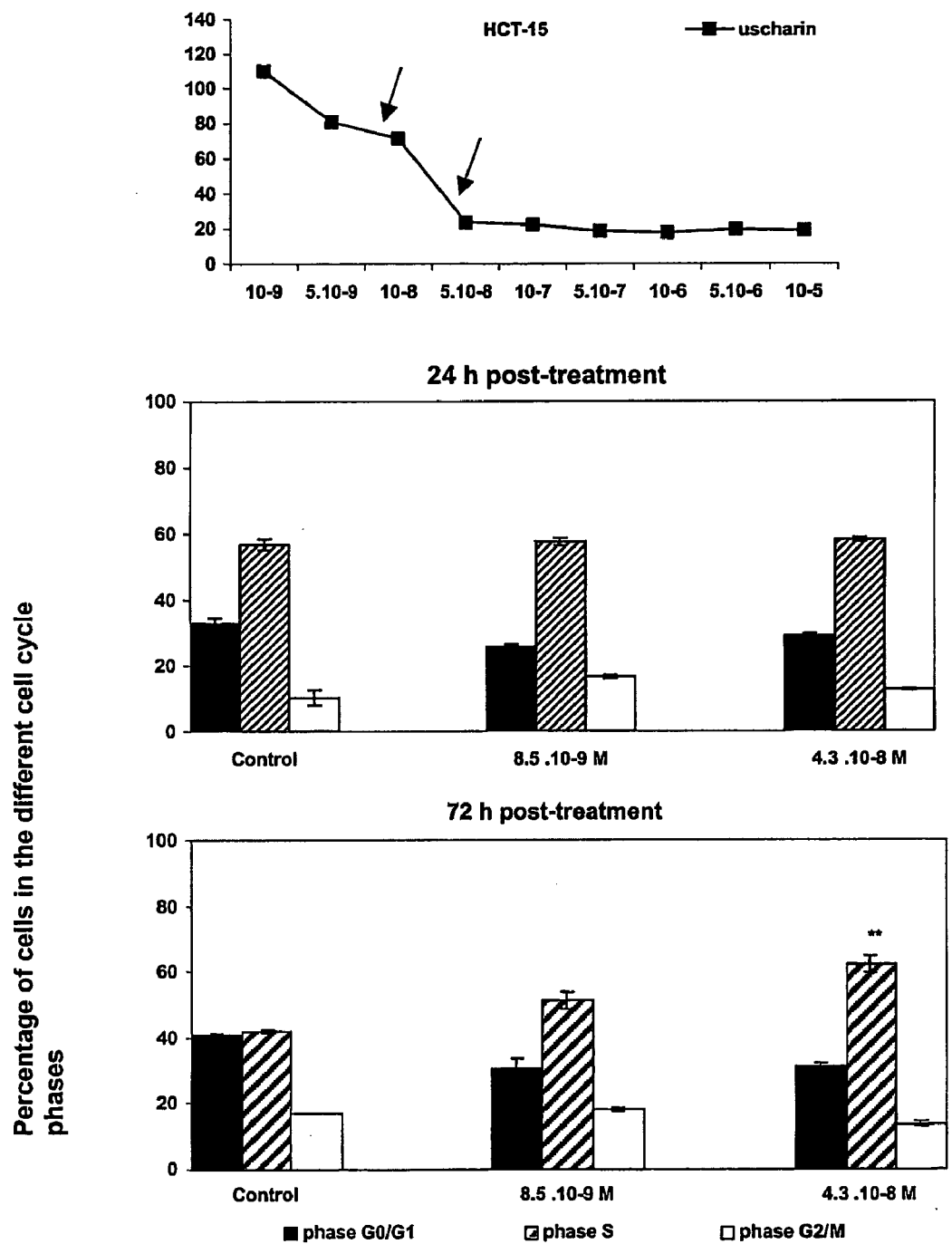
FIGS. 15 and 16 represent the effects of the compound uscharin and 2″ oxo-voruscharin, respectively, on the cell cycle kinetics of HCT-15 human cancer cells.

The analyses of cell cycle of the HCT-15 cells treated with uscharin (FIG. 15) and with 2"oxo-voruscharin (FIG. 16) showed that both compounds induced an accumulation in S-phase after 72 hours of treatment at the highest concentration tested respectively $4.3 \times 10^{-8}$ M and $1.2 \times 10^{-8}$ M.

The following table F recapitulates the most important effects obtained with uscharin and 2" oxo-voruscharin on the cycle kinetics of the 3 cell lines used after 24 and 72 hours-treatment. In conclusion, uscharin induced an accumulation in S-phase in each cell line tested. 2"Oxo-voruscharin induced an accumulation in the S phase and in G2/M phase. These results indicate that uscharin induced more accumulation of the cells in the S phase then 2"oxo-voruscharin. Accumulation of cells in the S phase upon treatment with uscharin indicates that the cells undergo DNA damage or breaks. Thus, a higher accumulation of cells in the S phase during uscharin treatment than during 2"oxo-voruscharin treatments indicates that 2" oxo-voruscharin has a lower toxicity than uscharin and thus may induce less side-effects on healthy cells.

TABLE F

Effects of uscharin and 2" oxo-voruscharin on the cell cycle kinetics of three human cancer cell lines

| Cell lines | Time | uscharin | | | 2" oxo-voruscharin | | |
|---|---|---|---|---|---|---|---|
| | | G0/G1 | S | G2/M | G0/G1 | S | G2/M |
| Hs683 | 24 h | n.s. | *** | *** | n.s. | n.s. | *** |
| | 72 h | n.s. | *** | n.s. | n.s. | n.s. | ** |
| J82 | 24 h | n.s. | *** | n.s. | n.s. | n.s. | n.s. |
| | 72 h | n.s. | *** | n.s. | n.s. | ** | n.s. |
| HCT-15 | 24 h | n.s. | n.s. | n.s. | n.s. | n.s. | n.s. |
| | 72 h | n.s. | ** | n.s. | n.s. | *** | n.s. |

Where n.s. means no significant;
** means highly significant;
*** very highly significant Example 5

Determination of the Maximum Tolerated Dose for the Compounds According to the Present Invention The Maximum Tolerated Dose (MTD) of a given drug is defined as the maximum amount of a drug which can be administered acutely (i.e. in one i.p., i.v., s.c. or per os single dose) to healthy animals, i.e. animals not grafted with tumors. The survival times and weights of the animals are recorded up to 14 days post-injection. Five different doses of each drug are used for the determination of the MTD index. When the MTD index is higher than 160 mg/kg (i.p. administration) the drug is usually considered to be non-toxic, and the highest dose administered to tumor-bearing mice is MTD/2=80 mg/kg. Each experimental group was composed of 3 mice for the determination of the MTD index.

The MTD index was measured for 2" oxo-voruscharin, compound B, compound C, compound D, compound H and compound I. The MTD index measured for a single administration in mice of these compounds were 20 mg/kg for 2" oxo-voruscharin, 80 mg/kg for compound B, superior to 40 mg/kg for compound C, 10 mg/kg for compound D, 80 mg/kg for compound H and 80 mg/kg for compound I.

Example 6

Determination of the In Vivo Anti-tumor Pharmacology for the Compounds According to the Present Invention Three types of results were obtained with in vivo anttumor pharmacology: 1) the cumulative toxicity of chemotherapeutic administrations through recording the weights of the tumor-bearing mice during treatment, 2) the actual anti-tumor effect exerted at tumor growth level. If the tumor models are grafted subcutaneously (s.c.), tumor size is measured three times a week by means of a caliper and expressed as an area ($mm^2$) by multiplying together the two largest perpendicular diameters, and 3) the gain in survival for the animals treated, which is evaluated by means of the T/C index. This index is the ratio between the median survival time of the group of treated animals (T) and that of the control group. The drug is considered to be active if the T/C value is above 130% ($P<0.05$), and toxic for a value lower than 70%.

The antitumoral activity of compound B was evaluated in different xenografted models: sub-cutanous model: MCF-7-TD5 (breast cancer) and C32 (melanoma cancer) and orthotopic model: A549 (lung cancer).

a. Breast Cancer Model:

The MCF-7-TD5 model described herein is a hormonosensitive form of MCF-7 transfected with v-Ha-ras oncogene and with a neomycin-resistance gene. Compound B was assayed at MTD/8 (10 mg/kg) and MTD/16 (5 mg/kg) five times a week.

Addition of oestradiol to the growth medium did not increase the proliferation rate of MCF-7-TD5 in vitro, while it produced a significant stimulation of the parental cells (Int. J. Cancer, 46, 522-532 (1990)). After s.c. injection of MCF-7-TD5 into untreated female nu/nu mice, the MCF-7 TD5 produced tumors after latency periods of 7 to 18 weeks. Treatment of mice with additional oestradiol resulted in a drastic shortening of the latency period and in a more rapid tumor growth. No oestradiol was used during the experiments described in this example.

FIG. 17 shows that 60 administrations of 10 mg/kg and 5 mg/kg of compound B significantly decreased MCF-7-TD5 tumor growth but this effect was not sufficient to significantly increase the survival periods of the MCF-7-TD5 tumor bearing mice. FIG. 18 indicates that the administration schedule of compound B used in the present experiment induced no major toxic-side effects since the MCF-7-TD5 tumor bearing mice did not lose any significant weight during constant compound B administrations. On the FIGS. 17 to 22, ↑Mx or ↓Mx refers to the day where the median mouse dies in each experiment.

Compound B exerts a significant anti-tumor effect on the MCF-7-TD5 breast cancer model without significant side-effects.

b. Melanoma Cancer Model

Experimental melanomas were set up in mice by painting their skins with a carcinogen. These experimental melanomas display certain morphological characteristics close to, those of human melanomas but are less aggressive biologically. Compound B was assayed at DMT/4 (20 mg/kg), DMT/8 (10 mg/kg) and DMT/16 (5 mg/kg) three times a week. Compound B at 25×20 mg/kg, 28×10 mg/kg and 21×5 mg/kg administration schedules did not significantly increase the survival periods of the C32 lung cancer-bearing mice. Indeed the T/C index values measured were respectively 95%, 107% and 81%.

FIGS. 19 and 20 indicate that the administration schedule of compound B used in the present experiment decreased the tumor area and did not induced any major toxic-side effects since the C32-tumor bearing mice did not loose any significant weight during constant administration of compound B. The most important effect was obtained with an administration schedule of 10 mg/kg.

Compound B therefore exerts a significant anti-tumor effect on the C32 melanoma cancer model by decreasing the tumor area.

c. Lung Cancer Model

Lung cancer is the leading cause of cancer deaths worldwide. Most patients die of progressive metastatic disease despite aggressive local and systemic therapies. The pathogenesis of lung cancer remains highly elusive due to its aggressive biologic nature and considerable heterogeneity, as compared to other cancers. Orthotopic lung cancer models are described in the literature using endobronchial, intrathoracic or intravenous injection of tumor cell suspensions and by surgical implantation of fresh tumor tissue. The tumor cells are directly injected into the lung of nude mice. The advantages of orthotopic models include improved tumor take and enhanced invasive and metastatic properties.

Compound B was assayed at DMT/2 (40 mg/kg), DMT/4 (20 mg/kg) and DMT/8 (10 mg/kg) three times a week. Compound B at 3×40 mg/kg administration schedule did not significantly increase the survival periods of the A549 lung cancer-bearing mice following the analysis of the T/C index for which the value was 124%. In contrast, when compound B was administrated at 7×20 mg/kg and 10×10 mg/kg, the T/C indexes were respectively of 152% and 186%. These values are statistically significant.

FIG. 21 represents the death rate of nine mice in each of the control and test groups during the experiment. Kaplan-Meier statistical analysis was used. The statistics value underlines the general fit of the test control in comparison with the general fit of the control group. As it can be seen from FIG. 22, whatever the used dose in this experiment, compound B significantly prolong the survival of the mice as compared to the untreated mice. The level significance was p<0.05.

FIG. 22 indicates that compound B administration schedule used in the present experiment did not induce any major toxic-side effects since the A549-tumor bearing mice did not lose any significant weight during constant compound B administrations, except during the first week of administration at 40 mg/kg where a significant loss of weight was observed.

Compound B exerts a significant anti-tumor effect on the A549 lung cancer, model by increasing significantly the survival period.

In conclusion, compound B has a significant anti-tumor effect on all the models used in the current series of experiments. These models represent a panel of histological tumor types, including breast cancer, lung cancer and melanomas. These models are clinically relevant because they mimic specific clinical stages of human cancers.

What is claimed is:

1. A compound of the formula I or a pharmaceutically acceptable salt thereof,

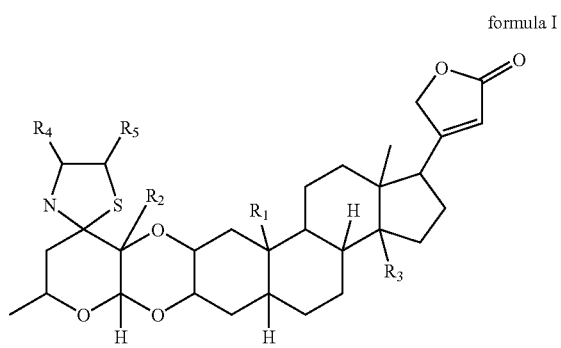

formula I wherein $R^1$ is selected from the group consisting of hydrogen, alkyl, alkenyl, alkynyl, alkyloxy, alkyloxyalkyl, alkylthioalkyl, alkyloxycarbonyl, alkylthiocarbonyl, alkanoyl, cycloalkylalkyl, cycloalkylcarbonyl, cycloalkylalkanoyl, cycloalkyithiocarbonyl, cycloalkylalkoxycarbonyl, cycloalkylalkoxythiocarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, arylthiocarbonyl, aralkoxycarbonyl, arylalkylthiocarbonyl, aryloxyalkyl, arylthioalkyl, haloalkyl, hydroxyalkyl, aralkanoyl, aroyl, aryloxycarbonylalkyl, aryloxyalkanoyl, carboxyl, formyl, alkenylcarbonyl, alkynylcarbonyl, $Het^1$, $Het^1$alkyl, $Het^1$oxyalkyl, $Het^1$aryl, $Het^1$aralkyl, $Het^1$cycloalkyl, $Het^1$carbonyl, $Het^1$alkoxycarbonyl, $Het^1$alkylthiocarbonyl, $Het^1$oxycarbonyl, $Het^1$thiocarbonyl, $Het^1$alkanoyl, $Het^1$aralkanoyl, $Het^1$aryloxyalkyl, $Het^1$alkyloxyalkyl, $Het^1$arylthioalkyl, $Het^1$aryloxycarbonyl, $Het^1$aralkoxycarbonyl, $Het^1$aroyl, $Het^1$oxyalkylcarbonyl, $Het^1$alkyloxyalkylcarbonyl, $Het^1$aryloxyalkylcarbonyl, $Het^1$carbonyloxyalkyl, $Het^1$alkylcarbonyloxyalkyl, $Het^1$aralkylcarbonyloxyalkyl, $Het^2$alkyl; $Het^2$oxyalkyl, $Het^2$alkyloxyalkyl, $Het^2$aralkyl, $Het^2$carbonyl, $Het^2$oxycarbonyl, $Het^2$thiocarbonyl, $Het^2$alkanoyl, $Het^2$alkylthiocarbonyl, $Het^2$alkoxycarbonyl, $Het^2$aralkanoyl, $Het^2$aralkoxycarbonyl, $Het^2$aryloxycarbonyl, $Het^2$aroyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $Het^2$carbonyloxyalkyl, $Het^2$alkylcarbonyloxyalkyl, $Het^2$aralkylcarbonyloxyalkyl, cyano, aminocarbonyl, aminoalkanoyl, aminoalkyl, $CR^6=NR^7$ and $CR^6=N$ (OR⁷), with R⁶ and R⁷ being independently selected from the group consisting of hydrogen, hydroxyl, alkyl, aryl, Het¹, Het¹alkyl, Het¹aryl, alkenyl, alkynyl, amino alkyl, aminoaryl, alkylcarbonylamino, arylcarbonylamino, alkylthiocarbonylamino and arylthiocarbonylamino;

wherein R² and R³ are independently selected from the group consisting of hydroxyl, alkyloxy, alkylsilyloxy, arylsilyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, haloalkyloxy, hydroxyalkyloxy, aralkanoyloxy, aroyloxy, aryloxycarbonylalkyloxy, formyloxy, Het¹alkyloxy, Het¹oxy, Het¹oxyalkyloxy, Het¹aryloxy, Het¹aralkyloxy, Het¹cycloalkyloxy, Het¹carbonyloxy, Het¹oxycarbonyloxy, Het¹alkanoyloxy, Het¹aralkanoyloxy, Het¹aryloxyalkyloxy, Het¹aroyl, Het²oxy, Het²alkyloxy; Het²oxyalkyloxy, Het²aralkyloxy, Het²cycloalkyloxy, Het²alkanoyloxy, Het²aralkanoyloxy, Het²carbonyloxyl, Het²aryloxy, and Het²aryloxyalkyloxy, wherein R¹ R² and R³ are unsubstituted or substituted by one or more substituents independently selected from the group consisting of alkyl, aralkyl, aryl, Het¹, Het², cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het¹, Het², Het¹alkyl, Het²alkyl, Het¹amino, Het²amino, Het¹alkylamino, Het²alkylamino, Het¹thio, Het²thio, Het¹alkylthio, Het²alkylthio, Het¹oxy and Het²oxy, OR⁸, SR⁸, SO₂NR⁸R⁹, SO₂N(OH)R⁸, CN, CR⁸=NR⁹, S(O)R⁸, SO₂R⁸, CR⁸=N(OR⁹), N₃, NO₂, NR⁸R⁹, N(OH)R⁸, C(O)R⁸, C(S)R⁸, CO₂R⁸, C(O)SR⁸, C(O)NR⁸R⁹, C(S)NR⁸R⁹, C(O)N(OH)R⁹, C(S)N(OH)R⁹, NR⁸C(O)R⁹, NR⁸C(S)R⁹, N(OH)C(O)R⁸, N(OH)C(S)R⁸, NR⁸CO₂R⁹, NR⁸C(O)NR⁹R¹⁰, NR⁸C(S)NR⁹R¹⁰, N(OH)CO₂R⁸, NR⁸C(O)SR⁹, N(OH)C(O)NR⁸R⁹, N(OH)C(S)NR⁸R⁹, NR⁸C(O)N(OH)R⁹, NR⁸C(S)N(OH)R⁹, NR⁸SO₂NHR⁹, NHSO₂NR⁸R⁹, NR⁸SO₂NHR⁹, and P(O)(OR⁸)(OR⁹), with t being an integer between 1 and 2, and R⁸ R⁹ and R¹⁰ being each independently selected from the group consisting of hydrogen, hydroxyl, alkyl, aryl, Het¹, Het¹alkyl, Het¹aryl, alkenyl, alkynyl, aminoalkyl, amino aryl, alkylcarbonylamino, arylcarbonylamino, alkylthiocarbonylamino and arylthiocarbonylamino;

wherein R⁴ is selected from the group consisting of oxo, hydroxyl, alkyl, alkenyl, alkynyl, alkanediyl, alkyloxy, alklylthio, alkylamino, alkyloxyalkyl, arylcarbonylalkyl, alkylcarbonylalkyl, alkanoyl, cycloalkylcarbonylalkyl, cycloalkyl, cycloalkyloxy, cycloalkylthio, cycloalkylamino, cycloalkylalkyl, cycloalkylalkanoyl, aryl, aralkyl, arylalkenyl, arylcarbonyloxy, aryloxycarbonyloxy, aralkoxycarbonyloxy, aryloxyalkyl, haloalkyloxy, haloalkylthio, haloalkylamino, hydroxyalkyl, aralkanoyl, aryloxycarbonylalkyl, aryloxyalkanoyl, Het¹, Het¹alkyl, Het¹oxy, Het¹oxyalkyl, Het¹aryl, Het¹aralkyl, Het¹cycloalkyl, Het¹aryloxyalkyl, Het¹aroyl, Het², Het²oxy, Het²alkyl; Het²oxyalkyl, Het²aralkyl, Het²cycloalkyl, Het²aryl, Het²alkanoyl, Het²aralkanoyl, Het²aroyl, Het²aryloxyalkyl, aminocarbonyl, aminoalkanoyl, and aminoalkyl, unsubstituted or substituted by one or more substituents independently selected from the group consisting of alkyl, aralkyl, aryl, Het¹, Het², cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het¹, Het², Het¹alkyl, Het²alkyl, Het¹amino, Het²amino, Het¹alkylamino, Het²alkylamino, Het¹thio, Het²thio, Het¹alkylthio, Het²alkylthio, Het¹oxy and Het²oxy, OR¹¹, SR¹¹, SO₂NR¹¹R¹², SO₂N(OH)R¹¹, CN, CR¹¹=NR¹², S(O)R¹¹, SO₂R¹¹, CR¹¹=N(OR¹²), N₃, NO₂, NR¹¹R¹², N(OH)R¹¹, C(O)R¹¹, C(S)R¹¹, CO₂R¹¹, C(O)SR¹¹, C(O)NR¹¹R¹², C(S)NR¹¹R¹², C(O)N(OH)R¹², C(S)N(OH)R¹¹, NR¹¹C(O)R¹², NR¹¹C(S)R¹², N(OH)C(O)R¹², N(OH)C(S)R¹¹, NR¹¹CO₂R¹², NR¹¹C(O)NR¹²R¹³, and NR¹¹C(S)NR¹²R¹³, N(OH)CO₂R¹¹, NR¹¹C(O)SR¹², N(OH)C(O)NR¹¹R¹², N(OH)C(S)NR¹¹R¹², NR¹¹C(O)N(OH)R¹², NR¹¹C(S)N(OH)R¹², NR¹¹SO₂R¹², MHSO₂NR¹¹R¹², NR¹¹SO₂NHR¹², P(O)(OR¹¹)(OR¹²), wherein t is an integer between 1 and 2, R¹¹, R¹² and R¹³ are each independently selected from the group consisting of hydrogen, alkyl, alkenyl, and alkynyl; and wherein R⁵ is selected from the group consisting of hydrogen, oxo, hydroxyl, alkyl, alkenyl, alkynyl, alkanediyl, alkyloxy, alkyloxyalkyl, arylcarbonylalkyl, alkylcarbonylalkyl, alkanoyl, cycloalkylcarbonylalkyl, cycloalkyl, cycloalkylalkyl, cycloalkylalkanoyl, aryl, aralkyl, arylalkenyl, arylcarbonyloxy, aryloxycarbonyloxy, aralkoxycarbonyloxy, aryloxyalkyl, halo alkyl, hydroxyalkyl, aralkanoyl, aryloxycarbonylalkyl, aryloxyalkanoyl, Het¹, Het¹alkyl, Het¹oxy, Het¹oxyalkyl, Het¹aryl, Het¹aralkyl, Het¹cycloalkyl, Het¹aryloxyalkyl, Het¹aroyl, Het², Het²oxy, Het²alkyl; Het²oxyalkyl, Het²aralkyl, Het²cycloalkyl, Het²aryl, Het²alkanoyl, Het²aralkanoyl, Het²aroyl, Het²aryloxyalkyl, aminocarbonyl, amino alkanoyl, and amino alkyl, unsubstituted or substituted by one or more substituents independently selected from the group consisting of alkyl, aralkyl, aryl, Het¹, Het², cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, aylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het$^1$, Het$^2$, Het$^1$alkyl, Het$^2$alkyl, Het$^1$amino, Het$^2$amino, Het$^1$alkylamino, Het$^2$alkylamino, Het$^1$thio, Het$^2$thio, Het$^1$alkylthio, Het$^2$alkylthio, Het$^1$oxy and Het$^2$oxy, OR$^{11}$, SR$^{11}$, SO$_2$NR$^{11}$R$^{12}$, SO$_2$N(OH)R$^{11}$, CN, CR$^{11}$=NR$^{12}$, S(O)R$^{11}$, SO$_2$R$^{11}$, CR$^{11}$=N(OR$^{12}$), N$_3$, NO$_2$, NR$^{11}$R$^{12}$, N(OH)R$^{11}$, C(O)R$^{11}$, C(S)R$^{11}$, CO$_2$R$^{11}$, C(O)SR$^{11}$, C(O)NR$^{11}$R$^{12}$, C(S)NR$^{11}$R$^{12}$, C(O)N(OH)R$^{12}$, C(S)N(OH)R$^{11}$, NR$^{11}$C(O)R$^{12}$, NR$^{11}$C(S)R$^{12}$, N(OH)C(O)R$^{12}$, N(OH)C(S)R$^{11}$, NR$^{11}$CO$_2$R$^{12}$, NR$^{11}$C(O)NR$^{12}$R$^{13}$, and NR$^{11}$C(S) NR$^{12}$R$^{13}$, N(OH)CO$_2$R$^{11}$, NR$^{11}$C(O)SR$^{12}$, N(OH)C (O)NR$^{11}$R$^{12}$, N(OH)C(S)NR$^{11}$R$^{12}$, NR$^{11}$C(O)N(OH) R$^{12}$, NR$^{11}$C(S)N(OH)R$^{12}$, NR$^{11}$SO$_2$R$^{12}$, NHSO$_2$NR$^{11}$R$^{12}$, NR$^{11}$SO$_2$NHR$^{12}$, and P(O)(OR$^{11}$) (OR$^{12}$), wherein t is an integer between 1 and 2, R$^{11}$, R$^{12}$ and R$^{13}$ are each independently selected from the group consisting of hydrogen, alkyl, alkenyl, and alkynyl;

wherein Het$^1$ is defined as a saturated or partially unsaturated monocyclic, bicyclic or polycyclic heterocycle consisting of 3 to 12 ring members which comprise one or more heteroatom ring members selected from nitrogen, oxygen or sulfur, optionally substituted on one or more carbon atoms by alkyl, alkyloxy, halogen, hydroxyl, oxo, optionally mono- or disubstituted amino, nitro, cyano, haloalkyl, carboxyl, alkoxycarbonyl cycloalkyl, optionally mono- or disubstituted aminocarbonyl, methylthio, methylsulfonyl, aryl and a saturated or partially unsaturated monocyclic, bicyclic or tricyclic heterocycle consisting of 3 to 12 ring members which contain one or more heteroatom ring members selected from nitrogen, oxygen or sulfur and whereby the optional substituents on any amino function are independently selected from alkyl, alkyloxy, Het$^2$, Het$^2$alkyl, Het$^2$oxy, Het$^2$oxyalkyl, aryl, aryloxy, aryloxyalkyl, aralkyl, alkyloxycarbonylamino, amino and aminoalkyl whereby each of the amino groups may optionally be mono- or disubstituted with alkyl;

wherein Het$^2$ is defined as an aromatic monocyclic, bicyclic or tricyclic heterocycle consisting of 3 to 12 ring members comprising one or more heteroatom ring members selected from nitrogen, oxygen or sulfur and optionally substituted on one or more carbon atoms by alkyl, alkyloxy, halogen, hydroxyl, optionally mono- or disubstituted amino, nitro, cyano, haloalkyl, carboxyl, alkoxycarbonyl, cycloalkyl, optionally mono- or disubstituted aminocarbonyl, methylthio, methylsulfonyl, aryl, Het$^1$ and an aromatic monocyclic, bicyclic, or tricyclic heterocycle consisting of 3 to 12 ring members, whereby the optional substituents on any amino function are independently selected from alkyl, alkyloxy, Het$^1$, Het$^1$alkyl, Het$^1$oxy, Het$^1$oxyalkyl, aryl, aryloxy, aryloxyalkyl, aralkyl, alkyloxycarbonylamino, amino, and amionalkyl whereby each of the amino groups may optionally be mono- or disubstituted with alkyl.

2. A compound according to claim 1, having the formula I or a pharmaceutically acceptable salt thereof,

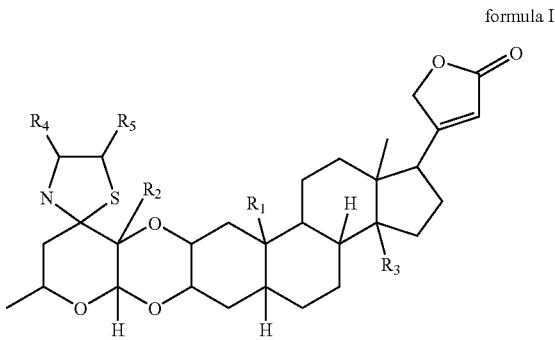

formula I wherein R$^1$ is selected from the group consisting of alkyl, alkenyl, alkynyl, alkyloxy, alkyloxyalkyl, alkylthioalkyl, alkyloxycarbonyl, alkylthiocarbonyl, alkanoyl, cycloalkylalkyl, cycloalkylcarbonyl, cycloalkylalkanoyl, cycloalkyithiocarbonyl, cycloalkylalkoxycarbonyl, cycloalkylalkoxythiocarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, arylthiocarbonyl, aralkoxycarbonyl, arylalkylthiocarbonyl, aryloxyalkyl, arylthioalkyl, haloalkyl, hydroxyalkyl, aralkanoyl, aroyl, aryloxycarbonylalkyl, aryloxyalkanoyl, carboxyl, formyl, alkenylcarbonyl, alkynylcarbonyl, Het$^1$, Het$^1$alkyl, Het$^1$oxyalkyl, Het$^1$aryl, Het$^1$aralkyl, Het$^1$cycloalkyl, Het$^1$carbonyl, Het$^1$alkoxycarbonyl, Het$^1$alkylthiocarbonyl, Het$^1$oxycarbonyl, Het$^1$thiocarbonyl, Het$^1$alkanoyl, Het$^1$aralkanoyl, Het$^1$aryloxyalkyl, Het$^1$alkyloxyalkyl, Het$^1$arylthioalkyl, Het$^1$aryloxycarbonyl, Het$^1$aralkoxycarbonyl, Het$^1$aroyl, Het$^1$oxyalkylcarbonyl, Het$^1$alkyloxyalkylcarbonyl, Het$^1$aryloxyalkylcarbonyl, Het$^1$carbonyloxyalkyl, Het$^1$alkylcarbonyloxyalkyl, Het$^1$aralkylcarbonyloxyalkyl, Het$^2$alkyl; Het$^2$oxyalkyl, Het$^2$alkyloxyalkyl, Het$^2$aralkyl, Het$^2$carbonyl, Het$^2$oxycarbonyl, Het$^2$thiocarbonyl, Het$^2$alkanoyl, Het$^2$alkylthiocarbonyl, Het$^2$alkoxycarbonyl, Het$^2$aralkanoyl, Het$^2$aralkoxycarbonyl, Het$^2$aryloxycarbonyl Het$^2$aroyl, Het$^2$aryloxyalkyl, Het$^2$arylthioalkyl, Het$^2$oxyalkylcarbonyl, Het$^2$alkyloxyalkylcarbonyl, Het$^2$aryloxyalkylcarbonyl, Het$^2$carbonyloxyalkyl, Het$^2$alkylcarbonyloxyalkyl, Het$^2$aralkylcarbonyloxyalkyl, cyano, aminocarbonyl, amino alkanoyl, aminoalkyl, CR$^6$=NR$^7$ and CR$^6$=N (OR$^7$), with R$^6$ and R$^7$ being independently selected from the group consisting of hydrogen, hydroxyl, alkyl, aryl, Het$^1$, Het$^1$alkyl, Het$^1$aryl, alkenyl, alkynyl, amino alkyl, amino aryl, alkylcarbonylamino, arylcarbonylamino, alkylthiocarbonylamino and arylthiocarbonylamino;

wherein R$^2$ and R$^3$ are independently selected from the group consisting of hydroxyl, alkyloxy, alkylsilyloxy, arylsilyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, halo alkyloxy, hydroxyalkyloxy, aralkanoyloxy, aroyloxy, aryloxycarbonylalkyloxy, formyloxy, Het$^1$alkyloxy, Het$^1$oxy, Het$^1$oxyalkyloxy, Het$^1$aryloxy, Het$^1$aralkyloxy, Het$^1$cycloalkyloxy, Het$^1$carbonyloxy, Het$^1$oxycarbonyloxy, Het$^1$alkanoyloxy, Het$^1$aralkanoyloxy, Het$^1$aryloxyalkyloxy, Het$^1$aroyl, Het$^2$oxy, Het$^2$alkyloxy; Het$^2$oxyalkyloxy, Het$^2$aralkyloxy, Het$^2$cycloalkyloxy, Het$^2$alkanoyloxy, Het$^2$aralkanoyloxy, Het$^2$carbonyloxyl, Het$^2$aryloxy, and Het$^2$aryloxyalkyloxy, wherein R$^1$ R$^2$ and R$^3$ are unsubstituted or substituted by one or more substituents independently selected from the group consisting of alkyl, aralkyl, aryl, Het$^1$, Het$^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het$^1$, Het$^2$, Het$^1$alkyl, Het$^2$alkyl, Het$^1$amino, Het$^2$amino, Het$^1$alkylamino, Het$^2$alkylamino, Het$^1$thio, Het$^2$thio, Het$^1$alkylthio, Het$^2$alkylthio, Het$^1$oxy and Het$^2$oxy, OR$^8$, SR$^8$, SO$_2$NR$^8$R$^9$, SO$_2$N(OH)R$^8$, CN, CR$^8$=NR$^9$, S(O)R$^8$, SO$_2$R$^8$, CR$^8$=N(OR$^9$), N$_3$, NO$_2$, NR$^8$R$^9$, N(OH)R$^8$, C(O)R$^8$, C(S)R$^8$, CO$_2$R$^8$, C(O)SR$^8$, C(O)NR$^8$R$^9$, C(S)NR$^8$R$^9$, C(O)N(OH)R$^9$, C(S)N(OH)R$^8$, NR$^8$C(O)R$^9$, NR$^8$C(S)R$^9$, N(OH)C(O)R$^9$, N(OH)C(S)R$^8$, NR$^8$CO$_2$R$^9$, NR$^8$C(O)NR$^9$R$^{10}$, NR$^8$C(S)NR$^9$R$^{10}$, N(OH)CO$_2$R$^8$, NR$^8$C(O)SR$^9$, N(OH)C(O)NR$^8$R$^9$, N(OH)C(S)NR$^8$R$^9$, NR$^8$C(O)N(OH)R$^9$, NR$^8$C(S)N(OH)R$^9$, NR$^8$SO$_2$R$^9$, NHSO$_2$NR$^8$R$^9$, NR$^8$SO$_2$NHR$^9$, and P(O)(OR$^8$)(OR$^9$), with t being an integer between 1 and 2, and R$^8$ R$^9$ and R$^{10}$ being each independently selected from the group consisting of hydrogen, hydroxyl, alkyl, aryl, Het$^1$, Het$^1$alkyl, Het$^1$aryl, alkenyl, alkynyl, amino alkyl, amino aryl, alkylcarbonylamino, arylcarbonylamino, alkyithiocarbonylamino and arylthiocarbonylamino;

wherein R$^4$ is oxo and R$^5$ is hydrogen or alkyl.

3. A compound according to claim 1, wherein R$^1$ is selected from the group consisting of hydrogen, alkyl, hydroxyalkyl, alkenyl, alkynyl, alkyloxyalkyl, alkylthioalkyl, alkyloxycarbonyl, alkanoyl, cycloalkylalkyl, cycloalkylcarbonyl, cycloalkylalkanoyl, cycloalkylalkoxycarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, aralkoxycarbonyl, arylthioalkyl, aralkanoyl, aroyl, carboxyl, formyl, alkenylcarbonyl, alkynylcarbonyl, Het$^1$oxyalkyl, Het$^1$alkoxycarbonyl, Het$^1$oxycarbonyl, Het$^1$aryloxyalkyl, Het$^1$alkyloxyalkyl, Het$^1$arylthioalkyl, Het$^1$aryloxycarbonyl, Het$^1$aralkoxycarbonyl, Het$^1$oxyalkylcarbonyl, Het$^1$alkyloxyalkylcarbonyl, Het$^1$aryloxyalkylcarbonyl, Het$^1$carbonyloxyalkyl, Het$^1$alkylcarbonyloxyalkyl, Het$^1$aralkylcarbonyloxyalkyl, Het$^2$oxyalkyl, Het$^2$alkyloxyalkyl, Het$^2$oxyalkyl, Het$^2$oxycarbonyl, Het$^2$alkoxycarbonyl, Het$^2$aralkoxycarbonyl, Het$^2$aryloxycarbonyl, Het$^2$aryloxyalkyl, Het$^2$arylthioalkyl, Het$^2$oxyalkylcarbonyl, Het$^2$alkyloxyalkylcarbonyl, Het$^2$aryloxyalkylcarbonyl, Het$^2$carbonyloxyalkyl, Het$^2$alkylcarbonyloxyalkyl, Het$^2$aralkylcarbonyloxyalkyl, CR$^6$=NR$^7$, and CR$^6$=N(OR$^7$), with R$^6$ and R$^7$ independently selected from the group consisting of hydrogen, hydroxyl, alkyl, aryl, Het$^1$, Het$^1$alkyl, Het$^1$aryl, alkenyl, alkynyl, aminoalkyl, aminoaryl, alkylcarbonylamino, arylcarbonylamino, alkylthiocarbonylamino and arylthiocarbonylamino;

wherein R$^2$ and R$^3$ are independently selected from the group consisting of hydroxyl, alkyloxy, alkyloxyalkyloxy, cycloalkyloxy, cycloalkylalkyloxy, aralkyloxy, aryloxyalkyloxy, silyloxy, alkylcarbonyloxy, arylcarbonyloxy, cycloalkylcarbonyloxy, aryloxycarbonylalkyloxy, formyloxy, Het$^1$alkyloxy, Het$^1$oxy, Het$^1$oxyalkyloxy, Het$^1$aryloxy, Het$^1$aralkyloxy, Het$^1$cycloalkyloxy, Het$^1$carbonyloxy, Het$^1$alkanoyloxy, Het$^1$aralkanoyloxy, Het$^1$aryloxyalkyloxy, Het$^2$oxy, Het$^2$alkyloxy, Het$^2$oxyalkyloxy, Het$^2$aralkyloxy, Het$^2$cycloalkyloxy, Het$^2$alkanoyloxy, Het$^2$aralkanoyloxy, Het$^2$carbonyloxyl, Het$^2$aryloxy, and Het$^2$aryloxyalkyloxy, wherein R$^1$ R$^2$ and R$^3$ are unsubstituted or substituted by one or more substituents independently selected from the group consisting of alkyl, aralkyl, aryl, Het$^1$, Het$^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het$^1$, Het$^2$, Het$^1$alkyl, Het$^2$alkyl, Het$^1$amino, Het$^2$amino, Het$^1$alkylamino, Het$^2$alkylamino, Het$^1$thio, Het$^2$thio, Het$^1$alkylthio, Het$^2$alkylthio, Het$^1$oxy and Het$^2$oxy, OR$^8$, SR$^8$, SO$_2$NR$^8$R$^9$, SO$_2$N(OH)R$^8$, CN, CR$^8$=NR$^9$, S(O)R$^8$, SO$_2$R$^8$, CR$^8$=N(OR$^9$), N$_3$, NO$_2$, NR$^8$R$^9$, N(OH)R$^8$, C(O)R$^8$, C(S)R$^8$, CO$_2$R$^8$, C(O)SR$^8$, C(O)NR$^8$R$^9$, C(S)NR$^8$R$^9$, C(O)N(OH)R$^9$, C(S)N(OH)R$^8$, NR$^8$C(O)R$^9$, NR$^8$C(S)R$^9$, N(OH)C(O)R$^9$, N(OH)C(S)R$^8$, NR$^8$CO$_2$R$^9$, NR$^8$C(O)NR$^9$R$^{10}$, NR$^8$C(S)NR$^9$R$^{10}$, N(OH)CO$_2$R$^8$, NR$^8$C(O)SR$^9$, N(OH)C(O)NR$^8$R$^9$, N(OH)C(S)NR$^8$R$^9$, NR$^8$C(O)N(OH)R$^9$, NR$^8$C(S)N(OH)R$^9$, NR$^8$SO$_2$R$^9$, NHSO$_2$NR$^8$R$^9$, NR$^8$SO$_2$NHR$^9$, and P(O)(OR$^8$)(OR$^9$), with t being an integer between 1 and 2, and R$^8$ R$^9$ and R$^{10}$ being each independently selected from the group consisting of hydrogen, hydroxyl, alkyl, aryl, Het$^1$, Het$^1$alkyl, Het$^1$aryl, alkenyl, alkynyl, aminoalkyl, aminoaryl, alkylcarbonylamino, arylcarbonylamino, alkylthiocarbonylamino and arylthiocarbonylamino; and wherein R$^4$ is selected from the group consisting of, oxo, hydroxyalkyl, alkyl, alkenyl, alkylcarbonylalkyl, arylcarbonylalkyl and R$^5$ is hydrogen, oxo, hydroxyl, hydroxyalkyl, alkyl, alkenyl, alkylcarbonylalkyl, arylcarbonylalkyl.

4. A compound according to claim 1 or 2, wherein R$^1$ is selected from the group consisting of alkyl, alkenyl, alkynyl, alkyloxyalkyl, alkylthioalkyl, alkyloxycarbonyl, alkanoyl, cycloalkylalkyl, cycloalkylcarbonyl, cycloalkylalkanoyl, cycloalkylalkoxycarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, aralkoxycarbonyl, arylthioalkyl, aralkanoyl, aroyl, carboxyl, formyl, alkenylcarbonyl, alkynylcarbonyl, $Het^1$oxyalkyl, $Het^1$alkoxycarbonyl, $Het^1$oxycarbonyl, $Het^1$aryloxyalkyl, $Het^1$alkyloxyalkyl, $Het^1$arylthioalkyl, $Het^1$aryloxycarbonyl, $Het^1$aralkoxycarbonyl, $Het^1$oxyalkylcarbonyl, $Het^1$alkyloxyalkylcarbonyl, $Het^1$aryloxyalkylcarbonyl, $Het^1$carbonyloxyalkyl, $Het^1$alkylcarbonyloxyalkyl, $Het^1$aralkylcarbonyloxyalkyl, $Het^2$oxyalkyl, $Het^2$alkyloxyalkyl, $Het^2$oxycarbonyl, $Het^2$alkoxycarbonyl, $Het^2$aralkoxycarbonyl, $Het^2$aryloxycarbonyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $Het^2$carbonyloxyalkyl, $Het^2$alkylcarbonyloxyalkyl, $Het^2$aralkylcarbonyloxyalkyl, $CR^6=NR^7$, and $CR^6=N(OR^7)$, with $R^6$ and $R^7$ being independently selected from the group consisting of hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkylthiocarbonylamino and arylthiocarbonylamino;

wherein $R^2$ and $R^3$ are independently selected from the group consisting of hydroxyl, alkyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, aryloxycarbonylalkyloxy, formyloxy, $Het^1$alkyloxy, $Het^1$oxy, $Het^1$oxyalkyloxy, $Het^1$aryloxy, $Het^1$aralkyloxy, $Het^1$cycloalkyloxy, $Het^1$carbonyloxy, $Het^1$alkanoyloxy, $Het^1$aralkanoyloxy, $Het^1$aryloxyalkyloxy, $Het^2$oxy, $Het^2$alkyloxy, $Het^2$oxyalkyloxy, $Het^2$aralkyloxy, $Het^2$cycloalkyloxy, $Het^2$alkanoyloxy, $Het^2$aralkanoyloxy, $Het^2$carbonyloxyl, $Het^2$aryloxy, and $Het^2$aryloxyalkyloxy, wherein $R^1$ $R^2$ and $R^3$ are unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, CN, $CR^8=NR^9$, $S(O)R^8$, $SO_2R^8$, $CR^8=N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^8$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$, with t being an integer between 1 and 2, and $R^8$ $R^9$ and $R^{10}$ being each independently selected from the group consisting of hydrogen, hydroxyl, alkyl, aryl, $Het^1$, $Het^1$alkyl, $Het^1$aryl, alkenyl, alkynyl, amino alkyl, amino aryl, alkylcarbonylamino, arylcarbonylamino, alkylthiocarbonylamino and arylthiocarbonylamino; and wherein $R^4$ is oxo and $R^5$ is hydrogen or alkyl.

5. A compound according to claim 1 or 2, wherein $R^1$ is selected from the group consisting of alkyl, alkenyl, alkynyl, alkyloxyalkyl, alkylthioalkyl, alkanoyl, cycloalkylalkyl, cycloalkylcarbonyl, cycloalkylalkanoyl, cycloalkylthioalkyl, silyloxyalkyl, aralkyl, arylalkenyl, arylcarbonyl, arylthioalkyl, aralkanoyl, aroyl, carboxyl, formyl, alkenylcarbonyl, alkynylcarbonyl, $Het^1$oxyalkyl, $Het^1$aryloxyalkyl, $Het^1$alkyloxyalkyl, $Het^1$arylthioalkyl, $Het^1$oxyalkylcarbonyl, $Het^1$alkyloxyalkylcarbonyl, $Het^1$aryloxyalkylcarbonyl, $Het^2$oxyalkyl, $Het^2$alkyloxyalkyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $CR^6=NR^7$, and $CR^6=N(OR^7)$, with $R^6$ and $R^7$ being independently selected from the group consisting of hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkyithiocarbonylamino and arylthiocarbonylamino;

wherein $R^2$ and $R^3$ are independently selected from the group consisting of hydroxyl, alkylcarbonyloxy, arylcarbonyloxy, cycloalkylcarbonyloxy, formyloxy, $Het^1$carbonyloxy, $Het^1$alkanoyloxy, $Het^1$aralkanoyloxy, $Het^2$carbonyloxyl, $Het^2$alkanoyloxy, and $Het^2$aralkanoyloxy, wherein $R^1$ $R^2$ and $R^3$ are unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, CN, $CR^8=NR^9$, $S(O)R^8$, $SO_2R^8$, $CR^8=N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^8$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$, with t being an integer between 1 and 2, and $R^8$ $R^9$ and $R^{10}$ being each independently selected from the group consisting of hydrogen, hydroxyl, alkyl, aryl, $Het^1$, Het$^1$alkyl, Het$^1$aryl, alkenyl, alkynyl, amino alkyl, aminoaryl, alkylcarbonylamino, arylcarbonylamino, alkyithiocarbonylamino and arylthiocarbonylamino; and wherein R$^4$ is oxo and R$^5$ is hydrogen or alkyl.

6. A compound according to claims 1 or 2 wherein R$^1$ is selected from the group consisting of alkyl, alkenyl, alkynyl, alkyloxyalkyl, alkylthioalkyl, cycloalkylalkyl, cycloalkylthioalkyl, silyloxyalkyl, aralkyl, arylalkenyl, arylthioalkyl, carboxyl, formyl, Het$^1$oxyalkyl, Het$^1$aryloxyalkyl, Het$^1$alkyloxyalkyl, Het$^1$arylthioalkyl, Het$^2$oxyalkyl, Het$^2$alkyloxyalkyl, Het$^2$aryloxyalkyl, and Het$^2$arylthioalkyl, unsubstituted or substituted by one or more substituents independently selected from the group consisting of alkyl, aralkyl, aryl, Het$^1$, Het$^2$, cycloalkyl, alkyloxycarbonyl, carboxyl, aminocarbonyl, mono- or di(alkyl)aminocarbonyl, aminosulfonyl, alkylS($\equiv$O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het$^1$, Het$^2$, Het$^1$alkyl, Het$^2$alkyl, Het$^1$amino, Het$^2$amino, Het$^1$alkylamino, Het$^2$alkylamino, Het$^1$thio, Het$^2$thio, Het$^1$alkylthio, Het$^2$alkylthio, Het$^1$oxy and Het$^2$oxy, OR$^8$, SR$^8$, SO$_2$NR$^8$R$^9$, SO$_2$N(OH)R$^8$, CN, CR$^8$=NR$^9$, S(O)R$^8$, SO$_2$R$^8$, CR$^8$=N(OR$^9$), N$_3$, NO$_2$, NR$^8$R$^9$, N(OH)R$^8$, C(O)R$^8$, C(S)R$^8$, CO$_2$R$^8$, C(O)SR$^8$, C(O)NR$^8$R$^9$, C(S)NR$^8$R$^9$, C(O)N(OH)R$^8$, C(S)N(OH)R$^8$, NR$^8$C(O)R$^9$, NR$^8$C(S)R$^9$, N(OH)C(O)R$^9$, N(OH)C(S)R$^8$, NR$^8$CO$_2$R$^9$, NR$^8$C(O)NR$^9$R$^{10}$, NR$^8$C(S)NR$^9$R$^{10}$, N(OH)CO$_2$R$^8$, NR$^8$C(O)SR$^9$, N(OH)C(O)NR$^8$R$^9$, N(OH)C(S)NR$^8$R$^9$, NR$^8$C(O)N(OH)R$^9$, NR$^8$C(S)N(OH)R$^9$, NR$^8$SO$_2$R$^9$, NHSO$_2$NR$^8$R$^9$, NR$^8$SO$_2$NHR$^9$, and P(O)(OR$^8$)(OR$^9$), with t being an integer between 1 and 2, and R$^8$ R$^9$ and R$^{10}$ being each independently selected from the group consisting of hydrogen, hydroxyl, alkyl, aryl, Het$^1$, Het$^1$alkyl, Het$^1$aryl, alkenyl, alkynyl, amino alkyl, aminoaryl, alkylcarbonylamino, arylcarbonylamino, alkyithiocarbonylamino and arylthiocarbonylamino; wherein R$^2$ and R$^3$ are hydroxyl and wherein R$^4$ is oxo and R$^5$ is hydrogen.

7. A compound according to claims 1 or 2, wherein R$^1$ is selected from the group consisting of alkyl, alkenyl, alkynyl, alkyloxyalkyl, cycloalkylalkyl, silyloxyalkyl, aralkyl, arylalkenyl, carboxyl, formyl, Het$^1$oxyalkyl, Het$^1$aryloxyalkyl, Het$^1$alkyloxyalkyl, Het$^2$oxyalkyl, Het$^2$alkyloxyalkyl, and Het$^2$aryloxyalkyl, unsubstituted or substituted by one or more substituents independently selected from the group consisting of alkyl, aralkyl, aryl, Het$^1$, Het$^2$, cycloalkyl, alkyloxycarbonyl, carboxyl, aminocarbonyl, mono- or di(alkyl)aminocarbonyl, aminosulfonyl, alkylS($\equiv$O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het$^1$, Het$^2$, Het$^1$alkyl, Het$^2$alkyl, Het$^1$amino, Het$^2$amino, Het$^1$alkylamino, Het$^2$alkylamino, Het$^1$thio, Het$^2$thio, Het$^1$alkylthio, Het$^2$alkylthio, Het$^1$oxy and Het$^2$oxy, OR$^8$, SR$^8$, SO$_2$NR$^8$R$^9$, SO$_2$N(OH)R$^8$, CN, CR$^8$=NR$^9$, S(O)R$^8$, SO$_2$R$^8$, CR$^8$=N(OR$^9$), N$_3$, NO$_2$, NR$^8$R$^9$, N(OH)R$^8$, C(O)R$^8$, C(S)R$^8$, CO$_2$R$^8$, C(O)SR$^8$, C(O)NR$^8$R$^9$, C(S)NR$^8$R$^9$, C(O)N(OH)R$^8$, C(S)N(OH)R$^8$, NR$^8$C(O)R$^9$, NR$^8$C(S)R$^9$, N(OH)C(O)R$^9$, N(OH)C(S)R$^8$, NR$^8$CO$_2$R$^9$, NR$^8$C(S)NR$^9$R$^{10}$, N(OH)CO$_2$R$^8$, NR$^8$C(O)SR$^9$, N(OH)C(O)NR$^8$R$^9$, N(OH)C(S)NR$^8$R$^9$, NR$^8$C(O)N(OH)R$^9$, NR$^8$C(S)N(OH)R$^9$, NR$^8$SO$_2$R$^9$, NHSO$_2$NR$^8$R$^9$, NR$^8$SO$_2$NHR$^9$, and P(O)(OR$^8$)(OR$^9$), with t being an integer between 1 and 2, and R$^8$ R$^9$ and R$^{10}$ being each independently selected from the group consisting of hydrogen, hydroxyl, alkyl, aryl, Het$^1$, Het$^1$alkyl, Het$^1$aryl, alkenyl, alkynyl, amino alkyl, amino aryl, alkylcarbonylamino, arylcarbonylamino, alkylthiocarbonylamino and arylthiocarbonylamino; wherein R$^2$ and R$^3$ are hydroxyl, R$^4$ is oxo and R$^5$ is hydrogen.

8. A compound according to claims 1 or 2, wherein R$^1$ is selected from the group consisting of alkyl, carboxyl, formyl; wherein R$^2$ and R$^3$ are hydroxyl, and wherein R$^4$ is oxo and R$^5$ is hydrogen.

9. A compound according to claim 8, wherein R$^1$ is formyl, R$^2$ and R$^3$ are hydroxyl R$^4$ is oxo and R$^5$ is hydrogen.

10. A compound according to claim 1 or 3, wherein R$^1$ is selected from the group consisting of hydrogen, alkyl, alkenyl, alkynyl, alkyloxyalkyl, hydroxyalkyl, alkylthioalkyl, alkanoyl, cycloalkylalkyl, cycloalkylcarbonyl, cycloalkylalkanoyl, cycloalkylthioalkyl, silyloxyalkyl, aralkyl, arylalkenyl, arylcarbonyl, arylthioalkyl, aralkanoyl, aroyl, carboxyl, formyl, alkenylcarbonyl, alkynylcarbonyl, Het$^1$oxyalkyl, Het$^1$aryloxyalkyl, Het$^1$alkyloxyalkyl, Het$^1$arylthioalkyl, Het$^1$oxyalkylcarbonyl, Het$^1$alkyloxyalkylcarbonyl, Het$^1$aryloxyalkylcarbonyl, Het$^2$oxyalkyl, Het$^2$alkyloxyalkyl, Het$^2$aryloxyalkyl, Het$^2$arylthioalkyl, Het$^2$oxyalkylcarbonyl, Het$^2$alkyloxyalkylcarbonyl, Het$^2$aryloxyalkylcarbonyl, CR$^6$=NR$^7$, and CR$^6$=N(OR$^7$), with R$^6$ and R$^7$ being independently selected from the group consisting of hydrogen, hydroxyl, alkyl, aryl, Het$^1$, Het$^1$alkyl, Het$^1$aryl, alkenyl, alkynyl, aminoalkyl, aminoaryl, alkylcarbonylamino, arylcarbonylamino, alkylthiocarbonylamino and arylthiocarbonylamino;

wherein R$^2$ and R$^3$ are independently selected from the group consisting of hydroxyl, alkylcarbonyloxy, arylcarbonyloxy, cycloalkylcarbonyloxy, formyloxy, Het$^1$carbonyloxy, Het$^1$alkanoyloxy, Het$^1$aralkanoyloxy, Het$^2$carbonyloxyl, Het$^2$alkanoyloxy, and Het$^2$aralkanoyloxy, wherein R$^1$ R$^2$ and R$^3$ are unsubstituted or substituted by one or more substituents independently selected from the group consisting of alkyl, aralkyl, aryl, Het$^1$, Het$^2$, cycloalkyl, alkyloxycarbonyl, carboxyl, aminocarbonyl, mono- or di(alkyl)aminocarbonyl, aminosulfonyl, alkylS($\equiv$O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, $CN$, $CR^8=NR^9$, $S(O)R^8$, $SO_2R^8CR^8=N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$, with t being an integer between 1 and 2, and $R^8$ $R^9$ and $R^{10}$ being each independently selected from the group consisting of hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkythiocarbonylamino and arylthiocarbonylamino; and wherein $R^4$ is oxo, hydroxyalkyl, alkyl, alkenyl, arylcarbonylaryl, or alkylcarbonylalkyl and $R^5$ is hydrogen or alkyl.

11. A compound according to claim 1 or 3, wherein $R^1$ is hydroxyalkyl, $R^2$ and $R^3$ are hydroxyl, $R^4$ is oxo and $R^5$ is hydrogen.

12. A compound according to claim 1 or 3, wherein $R^1$ is selected from the group consisting of hydrogen, alkyl, alkenyl, alkynyl, hydroxyalkyl, alkyloxyalkyl, alkylthioalkyl, cycloalkylalkyl, cycloalkylthioalkyl, silyloxyalkyl, aralkyl, arylalkenyl, arylthioalkyl, carboxyl, formyl, $Het^1$oxyalkyl, $Het^1$aryloxyalkyl, $Het^1$alkyloxyalkyl, $Het^1$arylthioalkyl, $Het^2$oxyalkyl, $Het^2$alkyloxyalkyl, $Het^2$aryloxyalkyl, and $Het^2$arylthioalkyl, unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, $alkylS(=O)_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, $CN$, $CR^8=NR^9$, $S(O)R^8$, $SO_2R^8$, $CR^8=N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)$ $NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$, with t being an integer between 1 and 2, and $R^8$ $R^9$ and $R^{10}$ being each independently selected from the group consisting of hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkyithiocarbonylamino and arylthiocarbonylamino; wherein $R^2$ and $R^3$ are hydroxyl and wherein $R^4$ is hydroxyalkyl, arylcarbonylalkyl, or alkylcarbonylalkyl and $R^5$ is hydrogen.

13. A compound according to claim 1 or 3, wherein $R^1$ is selected from the group consisting of hydrogen, alkyl, alkenyl, alkynyl, hydroxyalkyl, alkyloxyalkyl, cycloalkylalkyl, silyloxyalkyl, aralkyl, arylalkenyl, carboxyl, formyl, $Het^1$oxyalkyl, $Het^1$aryloxyalkyl, $Het^1$alkyloxyalkyl, $Het^2$oxyalkyl, $Het^2$alkyloxyalkyl, and $Het^2$aryloxyalkyl, unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, $alkylS(=O)_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, $CN$, $CR^8=NR^9$, $S(O)R^8$, $SO_2R^8$, $CR^8=N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$, with t being an integer between 1 and 2, and $R^8$ $R^9$ and $R^{10}$ being each independently selected from the group consisting of hydrogen, hydroxyl, alkyl, aryl, $Het^1$, $Het^1$alkyl, $Het^1$aryl, alkenyl, alkynyl, aminoalkyl, aminoaryl, alkylcarbonylamino, arylcarbonylamino, alkyithiocarbonylamino and arylthiocarbonylamino; wherein $R^2$ and $R^3$ are hydroxyl, $R^4$ is hydroxyalkyl, arylcarbonylalkyl, or alkylcarbonylalkyl and $R^5$ is hydrogen.

14. A compound according to claim 1 or 3, wherein $R^1$ is selected from the group consisting of alkyl, hydroxyalkyl, carboxyl, and formyl; wherein $R^2$ and $R^3$ are hydroxyl, and wherein $R^4$ is arylcarbonylalkyl and $R^5$ is hydrogen.

15. A compound according to claim 14, wherein $R^1$ is hydroxyalkyl, $R^2$ and $R^3$ are hydroxyl, $R^4$ is arylcarbonylalkyl and $R^5$ is hydrogen.

16. A compound according to claim 15, wherein $R^1$ is hydroxymethylene, $R^2$ and $R^3$ are hydroxyl, $R^4$ is phenylcarbonylmethylene and $R^5$ is hydrogen.

17. A compound having the formula Ia or a pharmaceutically acceptable salt or ester thereof, formula Ia

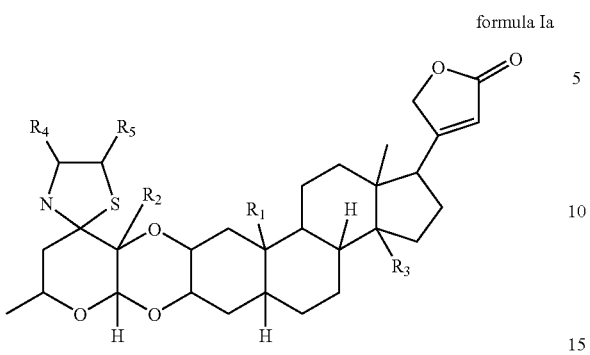

wherein R¹ is selected from the group consisting of alkyl, alkenyl, alkynyl, alkyloxyalkyl, alkylthioalkyl, alkyloxycarbonyl, alkanoyl, cycloalkylalkyl, cycloalkylcarbonyl, cycloalkylalkanoyl, cycloalkylalkoxycarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, aralkoxycarbonyl, arylthioalkyl, aralkanoyl, aroyl, silyloxyalkyl, carboxyl, alkenylcarbonyl, alkynylcarbonyl, Het¹oxyalkyl, Het¹alkoxycarbonyl, Het¹oxycarbonyl, Het¹aryloxyalkyl, Het¹alkyloxyalkyl, Het¹arylthioalkyl, Het¹aryloxycarbonyl, Het¹aralkoxycarbonyl, Het¹oxyalkylcarbonyl, Het¹alkyloxyalkylcarbonyl, Het¹aryloxyalkylcarbonyl, Het¹carbonyloxyalkyl, Het¹alkylcarbonyloxyalkyl, Het¹aralkylcarbonyloxyalkyl, Het²oxyalkyl, Het²alkyloxyalkyl, Het²oxycarbonyl, Het²alkoxycarbonyl, Het²aralkoxycarbonyl, Het²aryloxycarbonyl, Het²aryloxyalkyl, Het²arylthioalkyl, Het²oxyalkylcarbonyl, Het²alkyloxyalkylcarbonyl, Het²aryloxyalkylcarbonyl, Het²carbonyloxyalkyl, Het²alkylcarbonyloxyalkyl, Het²aralkylcarbonyloxyalkyl, CR⁶=NR⁷, and CR⁶=N(OR⁷), with R⁶ and R⁷ being independently selected from the group consisting of hydrogen, hydroxyl, alkyl, aryl, Het¹, Het¹alkyl, Het¹aryl, alkenyl, alkynyl, aminoalkyl, aminoaryl, alkylcarbonylamino, arylcarbonylamino, alkylthiocarbonylamino and arylthiocarbonylamino;

wherein R² and R³ are independently selected from the group consisting of hydroxyl, alkyloxy, alkylsilyloxy, arylsilyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, haloalkyloxy, hydroxyalkyloxy, aralkanoyloxy, aroyloxy, aryloxycarbonylalkyloxy, formyloxy, Het¹alkyloxy, Het oxy, Het oxyalkyloxy, Het¹aryloxy, Het¹aralkyloxy, Het¹cycloalkyloxy, Het¹carbonyloxy, Het¹oxycarbonyloxy, Het¹alkanoyloxy, Het¹aralkanoyloxy, Het¹aryloxyalkyloxy, Het¹aroyl, Het²oxy, Het²alkyloxy; Hetoxyalkyloxy, Het²aralkyloxy, Het²cycloalkyloxy, Het²alkanoyloxy, Het²aralkanoyloxy, Het²carbonyloxyl, Het²aryloxy, and Het²aryloxyalkyloxy;

wherein R¹ R² and R³ are unsubstituted or substituted by one or more substituents independently selected from the group consisting of alkyl, aralkyl, aryl, Het¹, Het², cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het¹, Het², Het¹alkyl, Het²alkyl, Het¹amino, Het²amino, Het¹alkylamino, Het²alkylamino, Het¹thio, Het²thio, Het¹alkylthio, Het²alkylthio, Het¹oxy and Het²oxy, OR⁸, SR⁸, SO₂NR⁸R⁹, SO₂N(OH)R⁸, CN, CR⁸=NR⁹, S(O)R⁸, SO₂R⁸, CR⁸=N(OR⁹), N₃, NO₂, NR⁸R⁹, N(OH)R⁸, C(O)R⁸, C(S)R⁸, CO₂R⁸, C(O)SR⁸, C(O)NR⁸R⁹, C(S)NR⁸R⁹, C(O)N(OH)R⁹, C(S)N(OH)R⁸, NR⁸C(O)R⁹, NR⁸C(S)R⁹, N(OH)C(O)R⁹, N(OH)C(S)R⁸, NR⁸CO₂R⁹, NR⁸C(O)NR⁹R¹⁰, NR⁸C(S)NR⁹R¹⁰, N(OH)CO₂R⁸, NR⁸C(O)SR⁹, N(OH)C(O)NR⁸R⁹, N(OH)C(S)NR⁸R⁹, NR⁸C(O)N(OH)R⁹, NR⁸C(S)N(OH)R⁹, NR⁸SO₂R⁹, NHSO₂NR⁸R⁹, NR⁸SO₂NHR⁹, and P(O)(OR⁸)(OR⁹), with t being an integer between 1 and 2, and R⁸ R⁹ and R¹⁰ being each independently selected from the group consisting of hydrogen, hydroxyl, alkyl, aryl, Het¹, Het¹alkyl, Het¹aryl, alkenyl, alkynyl, aminoalkyl, aminoaryl, alkylcarbonylamino, arylcarbonylamino, alkyithiocarbonylamino and arylthiocarbonylamino;

wherein R⁴ and R⁵ are hydrogen or alkyl;

wherein Het¹ is defined as a saturated or partially unsaturated monocyclic, bicyclic or polycyclic heterocycle consisting of 3 to 12 ring members which comprise one or more heteroatom ring members selected from nitrogen, oxygen or sulfur, optionally substituted on one or more carbon atoms by alkyl, alkyloxy, halogen, hydroxyl, oxo, optionally mono- or disubstituted amino, nitro, cyano, haloalkyl, carboxyl, alkoxycarbonyl cycloalkyl, optionally mono- or disubstituted aminocarbonyl, methylthio, methylsulfonyl, aryl and a saturated or partially unsaturated monocyclic, bicyclic or tricyclic heterocycle consisting of 3 to 12 ring members which contain one or more heteroatom ring members selected from nitrogen, oxygen or sulfur and whereby the optional substituents on any amino function are independently selected from alkyl, alkyloxy, Het², Het²alkyl, Het²oxy, Het²oxyalkyl, aryl, aryloxy, aryloxyalkyl, aralkyl, alkyloxycarbonylamino, amino and aminoalkyl whereby each of the amino groups may optionally be mono- or disubstituted with alkyl;

wherein Het² is defined as an aromatic monocyclic, bicyclic or tricyclic heterocycle consisting of 3 to 12 ring members comprising one or more heteroatom ring members selected from nitrogen, oxygen or sulfur and optionally substituted on one or more carbon atoms by alkyl, alkyloxy, halogen, hydroxyl, optionally mono- or disubstituted amino, nitro, cyano, haloalkyl, carboxyl, alkoxycarbonyl, cycloalkyl, optionally mono- or disubstituted aminocarbonyl, methylthio, methylsulfonyl, aryl, Het¹ and an aromatic monocyclic, bicyclic, or tricyclic heterocycle consisting of 3 to 12 ring members, whereby the optional substituents on any amino function are independently selected from alkyl, alkyloxy, Het¹, Het¹alkyl, Het¹oxy, Het¹oxyalkyl, aryl, aryloxy, aryloxyalkyl, aralkyl, alkyloxycarbonylamino, amino, and amionalkyl whereby each of the amino groups may optionally be mono- or disubstituted with alkyl.

18. A compound according to claim 17,
wherein $R^1$ is selected from the group consisting of alkyl, alkenyl, alkynyl, alkyloxyalkyl, alkylthioalkyl, alkanoyl, cycloalkylalkyl, cycloalkylcarbonyl, cycloalkylalkanoyl, cycloalkylthioalkyl, silyloxyalkyl, aralkyl, arylalkenyl, arylcarbonyl, arylthioalkyl, aralkanoyl, aroyl, silyloxyalkyl, carboxyl, alkenylcarbonyl, alkynylcarbonyl, $Het^1$oxyalkyl, $Het^1$aryloxyalkyl, $Het^1$alkyloxyalkyl, $Het^1$arylthioalkyl, $Het^1$oxyalkylcarbonyl, $Het^1$alkyloxyalkylcarbonyl, $Het^1$aryloxyalkylcarbonyl, $Het^2$oxyalkyl, $Het^2$alkyloxyalkyl, $Het^2$aryloxyalkyl, $Het^2$arylthioalkyl, $Het^2$oxyalkylcarbonyl, $Het^2$alkyloxyalkylcarbonyl, $Het^2$aryloxyalkylcarbonyl, $CR^6{=}NR^7$, and $CR^6{=}N(OR^7)$, with $R^6$ and $R^7$ being independently selected from the group consisting of hydrogen, hydroxyl, alkyl, aryl, $Het^1$, $Het^1$alkyl, $Het^1$aryl, alkenyl, alkynyl, amino alkyl, aminoaryl, alkylcarbonylamino, arylcarbonylamino, alkylthiocarbonylamino and arylthiocarbonylamino;
wherein $R^2$ and $R^3$ are independently selected from the group consisting of hydroxyl, alkyloxy, alkylsilyloxy, arylsilyloxy, alkyloxyalkyloxy, cycloalkyloxy cycloalkylalkyloxy, aralkyloxy, aryloxyalkyloxy, silyloxy, alkylcarbonyloxy, arylcarbonyloxy, cycloalkylcarbonyloxy, halo alkyloxy, hydroxyalkyloxy, aralkanoyloxy, aroyloxy, aryloxycarbonylalkyloxy, formyloxy, $Het^1$alkyloxy, $Het^1$oxy, $Het^1$oxyalkyloxy, $Het^1$aryloxy, $Het^1$aralkyloxy, $Het^1$cycloalkyloxy, $Het^1$carbonyloxy, $Het^1$oxycarbonyloxy, $Het^1$alkanoyloxy, $Het^1$aralkanoyloxy, $Het^1$aryloxyalkyloxy, $Het^1$aroyl, $Het^2$oxy, $Het^2$alkyloxy; $Het^2$oxyalkyloxy, $Het^2$aralkyloxy, $Het^2$cycloalkyloxy, $Het^2$alkanoyloxy, $Het^2$aralkanoyloxy, $Het^2$carbonyloxyl, $Het^2$aryloxy, and $Het^2$aryloxyalkyloxy;
wherein $R^1$ $R^2$ and $R^3$ are unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, $alkylS({=}O)_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, CN, $CR^8{=}NR^9$, $S(O)R^8$, $SO_2R^8$, $CR^8{=}N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$,
with t being an integer between 1 and 2, and $R^8$ $R^9$ and $R^{10}$ being each independently selected from the group consisting of hydrogen, hydroxyl, alkyl, aryl, $Het^1$, $Het^1$alkyl, $Het^1$aryl, alkenyl, alkynyl, amino alkyl, aminoaryl, alkylcarbonylamino, arylcarbonylamino, alkylthiocarbonylamino and arylthiocarbonylamino; and
wherein $R^4$ and $R^5$ are hydrogen or alkyl.

19. A compound according to claim 17 or 18, wherein $R^1$ is selected from the group consisting of alkyl, alkenyl, alkynyl, alkyloxyalkyl, alkylthioalkyl, cycloalkylalkyl, cycloalkylthioalkyl, silyloxyalkyl, aralkyl, arylalkenyl, arylthioalkyl, silyloxyalkyl, carboxyl, $Het^1$oxyalkyl, $Het^1$aryloxyalkyl, $Het^1$alkyloxyalkyl, $Het^1$arylthioalkyl, $Het^2$oxyalkyl, $Het^2$alkyloxyalkyl, $Het^2$aryloxyalkyl, and $Het^2$arylthioalkyl, unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, $alkylS({=}O)_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, CN, $CR^8{=}NR^9$, $S(O)R^8$, $SO_2R^8$, $CR^8{=}N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)$ $NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$,
with t being an integer between 1 and 2, and $R^8$ $R^9$ and $R^{10}$ being each independently selected from the group consisting of hydrogen, hydroxyl, alkyl, aryl, $Het^1$, $Het^1$alkyl, $Het^1$aryl, alkenyl, alkynyl, aminoalkyl, amino aryl, alkylcarbonylamino, arylcarbonylamino, alkyithiocarbonylamino and arylthiocarbonylamino;
wherein $R^2$ and $R^3$ are hydroxyl and wherein $R^4$ and $R^5$ are hydrogen or alkyl.

20. A compound according to claim 17 or 18, wherein $R^1$ is selected from the group consisting of alkyl, alkenyl, alkynyl, alkyloxyalkyl, cycloalkylalkyl, silyloxyalkyl, aralkyl, arylalkenyl, carboxyl, $Het^1$oxyalkyl, $Het^1$aryloxyalkyl, $Het^1$alkyloxyalkyl, $Het^2$oxyalkyl, $Het^2$alkyloxyalkyl, and $Het^2$aryloxyalkyl, unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, $alkylS({=}O)_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, Het², Het¹alkyl, Het²alkyl, Het¹amino, Het²amino, Het¹alkylamino, Het²alkylamino, Het¹thio, Het²thio, Het¹alkylthio, Het²alkylthio, Het¹oxy and Het²oxy, OR⁸, SR⁸, SO₂NR⁸R⁹, SO₂N(OH)R⁸, CN, CR⁸=NR⁹, S(O)R⁸, SO₂R⁸, CR⁸=N(OR⁹), N₃, NO₂, NR⁸R⁹, N(OH)R⁸, C(O)R⁸, C(S)R⁸, CO₂R⁸, C(O)SR⁸, C(O)NR⁸R⁹, C(S)NR⁸R⁹, C(O)N(OH)R⁹, C(S)N(OH)R⁸, NR⁸C(O)R⁹, NR⁸C(S)R⁹, N(OH)C(O)R⁹, N(OH)C(S)R⁸, NR⁸CO₂R⁹, NR⁸C(O)NR⁹R¹⁰, NR⁸C(S)NR⁹R¹⁰, N(OH)CO₂R⁸, NR⁸C(O)SR⁹, N(OH)C(O)NR⁸R⁹, N(OH)C(S)NR⁸R⁹, NR⁸C(S)N(OH)R⁹, NR⁸C(S)N(OH)R⁹, NR⁸SO₂R⁹, NHSO₂NR⁸R⁹, NR⁸SO₂NHR⁹, and P(O)(OR⁸)(OR⁹), with t being an integer between 1 and 2, and R⁸ R⁹ and R¹⁰ being each independently selected from the group consisting of hydrogen, hydroxyl, alkyl, aryl, Het¹, Het¹alkyl, Het¹aryl, alkenyl, alkynyl, amino alkyl, aminoaryl, alkylcarbonylamino, arylcarbonylamino, alkyithiocarbonylamino and arylthiocarbonylamino; wherein R² and R³ are hydroxyl and wherein R⁴ and R⁵ are hydrogen.

21. A compound having the formula Ib or a pharmaceutically acceptable salt or ester thereof,

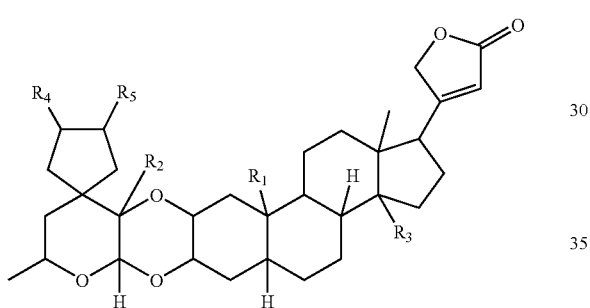

formula Ib wherein R¹ is selected from the group consisting of alkenyl, alkynyl, alkyloxyalkyl, alkylthioalkyl, alkyloxycarbonyl, alkanoyl, cycloalkylalkyl, cycloalkylcarbonyl, cycloalkylalkanoyl, cycloalkylalkoxycarbonyl, cycloalkylthioalkyl, alkylcarbonyloxyalkyl, arylcarbonyloxyalkyl, cycloalkylcarbonyloxyalkyl, silyloxyalkyl, aralkyl, arylalkenyl, arylcarbonyl, aryloxycarbonyl, aralkoxycarbonyl, arylthioalkyl, aralkanoyl, aroyl, silyloxyalkyl, carboxyl, alkenylcarbonyl, alkynylcarbonyl, Het¹oxyalkyl, Het¹alkoxycarbonyl, Het¹oxycarbonyl, Het¹aryloxyalkyl, Het¹alkyloxyalkyl, Het¹arylthioalkyl, Het¹aryloxycarbonyl, Het¹aralkoxycarbonyl, Het¹oxyalkylcarbonyl, Het¹alkyloxyalkylcarbonyl, Het¹aryloxyalkylcarbonyl, Het¹carbonyloxyalkyl, Het¹alkylcarbonyloxyalkyl, Het¹aralkylcarbonyloxyalkyl, Het²oxyalkyl, Het²alkyloxyalkyl, Het²oxycarbonyl, Het²alkoxycarbonyl, Het²aralkoxycarbonyl, Het²aryloxycarbonyl, Het²aryloxyalkyl, Het²arylthioalkyl, Het²oxyalkylcarbonyl, Het²alkyloxyalkylcarbonyl, Het²aryloxyalkylcarbonyl, Het²carbonyloxyalkyl, Het²alkylcarbonyloxyalkyl, Het²aralkylcarbonyloxyalkyl, CR⁶=NR⁷, and CR⁶=N(OR⁷), with R⁶ and R⁷ being independently selected from the group consisting of hydrogen, hydroxyl, alkyl, aryl, Het¹, Het¹alkyl, Het¹aryl, alkenyl, alkynyl, aminoalkyl, amino aryl, alkylcarbonylamino, arylcarbonylamino, alkylthiocarbonylamino and arylthiocarbonylamino;

wherein R¹ is unsubstituted or substituted by one or more substituents independently selected from the group consisting of alkyl, aralkyl, aryl, Het¹, Het², cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, Het¹, Het², Het¹alkyl, Het²alkyl, Het¹amino, Het²amino, Het¹alkylamino, Het²alkylamino, Het¹thio, Het²thio, Het¹alkylthio, Het²alkylthio, Het¹oxy and Het²oxy, OR⁸, SR⁸, SO₂NR⁸R⁹, SO₂N(OH)R⁸, CN, CR⁸=NR⁹, S(O)R⁸, SO₂R⁸, CR⁸=N(OR⁹), N₃, NO₂, NR⁸R⁹, N(OH)R⁸, C(O)R⁸, C(S)R⁸, CO₂R⁸, C(O)SR⁸, C(O)NR⁸R⁹, C(S)NR⁸R⁹, C(O)N(OH)R⁹, C(S)N(OH)R⁸, NR⁸C(O)R⁹, NR⁸C(S)R⁹, N(OH)C(O)R⁹, N(OH)C(S)R⁸, NR⁸CO₂R⁹, NR⁸C(O)NR⁹R¹⁰, NR⁸C(S)NR⁹R¹⁰, N(OH)CO₂R⁸, NR⁸C(O)SR⁹, N(OH)C(O)NR⁸R⁹, N(OH)C(S)NR⁸R⁹, NR⁸C(O)N(OH)R⁹, NR⁸C(S)N(OH)R⁹, NR⁸SO₂R⁹, NHSO₂NR⁸R⁹, NR⁸SO₂NHR⁹, and P(O)(OR⁸)(OR⁹), with t being an integer between 1 and 2, and R⁸ R⁹ and R¹⁰ being each independently selected from the group consisting of hydrogen, hydroxyl, alkyl, aryl, Het¹, Het¹alkyl, Het¹aryl, alkenyl, alkynyl, amino alkyl, aminoaryl, alkylcarbonylamino, arylcarbonylamino, alkylthiocarbonylamino and arylthiocarbonylamino, and wherein R² and R³ are hydroxyl and wherein R⁴ is replaced by a double bond between the N atom and the C carbon atom of the N-containing heterocyclic ring of formula Ib; and wherein R⁵ is hydrogen;

wherein Het¹ is defined as a saturated or partially unsaturated monocyclic, bicyclic or polycyclic heterocycle consisting of 3 to 12 ring members which comprise one or more heteroatom ring members selected from nitrogen, oxygen or sulfur, optionally substituted on one or more carbon atoms by alkyl, alkyloxy, halogen, hydroxyl, oxo, optionally mono- or disubstituted amino, nitro, cyano, haloalkyl, carboxyl, alkoxycarbonyl cycloalkyl, optionally mono- or disubstituted aminocarbonyl, methylthio, methylsulfonyl, aryl and a saturated or partially unsaturated monocyclic, bicyclic or tricyclic heterocycle consisting of 3 to 12 ring members which contain one or more heteroatom ring members selected from nitrogen, oxygen or sulfur and whereby the optional substituents on any amino function are independently selected from alkyl, alkyloxy, Het², Het²alkyl, Het²oxy, Het²oxyalkyl, aryl, aryloxy, aryloxyalkyl, aralkyl, alkyloxycarbonylamino, amino and aminoalkyl whereby each of the amino groups may optionally be mono- or disubstituted with alkyl;

wherein Het² is defined as an aromatic monocyclic, bicyclic or tricyclic heterocycle consisting of 3 to 12 ring members comprising one or more heteroatom ring members selected from nitrogen, oxygen or sulfur and optionally substituted on one or more carbon atoms by alkyl, alkyloxy, halogen, hydroxyl, optionally mono- or disubstituted amino, nitro, cyano, haloalkyl, carboxyl, alkoxycarbonyl, cycloalkyl, optionally mono- or disubstituted aminocarbonyl, methylthio, methylsulfonyl, aryl, $Het^1$ and an aromatic monocyclic, bicyclic, or tricyclic heterocycle consisting of 3 to 12 ring members, whereby the optional substituents on any amino function are independently selected from alkyl, alkyloxy, $Het^1$, $Het^1$alkyl, $Het^1$oxy, $Het^1$oxyalkyl, aryl, aryloxy, aryloxyalkyl, aralkyl, alkyloxycarbonylamino, amino, and amionalkyl whereby each of the amino groups may optionally be mono- or disubstituted with alkyl.

22. A compound according to claim 21, wherein $R^1$ is selected from the group consisting of alkenyl, alkynyl, alkyloxyalkyl, cycloalkylalkyl, silyloxyalkyl, aralkyl, arylalkenyl, carboxyl, $Het^1$oxyalkyl, $Het^1$aryloxyalkyl, $Het^1$alkyloxyalkyl, $Het^2$oxyalkyl, $Het^2$alkyloxyalkyl, and $Het^2$aryloxyalkyl, unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, CN, $CR^8$=$NR^9$, $S(O)R^8$, $SO_2R^8$, $CR^8$=$N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$, with t being an integer between 1 and 2, and $R^8$ $R^9$ and $R^{10}$ being each independently selected from the group consisting of hydrogen, hydroxyl, alkyl, aryl, $Het^1$, $Het^1$alkyl, $Het^1$aryl, alkenyl, alkynyl, aminoalkyl, amino aryl, alkylcarbonylamino, arylcarbonylamino, alkylthiocarbonylamino and arylthiocarbonylamino; wherein $R^2$ and $R^3$ are hydroxyl and wherein $R^4$ and $R^5$ are hydrogen.

23. A compound according to claim 22, wherein $R^1$ is selected from the group consisting of alkyl, alkenyl, alkynyl, alkyloxyalkyl, cycloalkylalkyl, silyloxyalkyl, aralkyl, arylalkenyl, carboxyl, $Het^1$oxyalkyl, $Het^1$aryloxyalkyl, $Het^1$alkyloxyalkyl, $Het^2$oxyalkyl, $Het^2$alkyloxyalkyl, and $Het^2$aryloxyalkyl, unsubstituted or substituted by one or more substituents independently selected from the group consisting of alkyl, aralkyl, aryl, $Het^1$, $Het^2$, cycloalkyl, alkyloxycarbonyl, carboxyl, aminocarbonyl, mono- or di(alkyl)aminocarbonyl, aminosulfonyl, alkylS(=O)$_t$, hydroxy, cyano, halogen and amino, unsubstituted, mono- or disubstituted wherein the substituents are independently selected from the group consisting of alkyl, aryl, aralkyl, aryloxy, arylamino, arylthio, aryloxyalkyl, arylaminoalkyl, aralkoxy, alkylthio, alkoxy, aryloxyalkoxy, arylaminoalkoxy, aralkylamino, aryloxyalkylamino, arylaminoalkylamino, arylthioalkoxy, arylthioalkylamino, aralkylthio, aryloxyalkylthio, arylaminoalkylthio, arylthioalkylthio, alkylamino, cycloalkyl, cycloalkylalkyl, $Het^1$, $Het^2$, $Het^1$alkyl, $Het^2$alkyl, $Het^1$amino, $Het^2$amino, $Het^1$alkylamino, $Het^2$alkylamino, $Het^1$thio, $Het^2$thio, $Het^1$alkylthio, $Het^2$alkylthio, $Het^1$oxy and $Het^2$oxy, $OR^8$, $SR^8$, $SO_2NR^8R^9$, $SO_2N(OH)R^8$, CN, $CR^8$=$NR^9$, $S(O)R^8$, $SO_2R^8$, $CR^8$=$N(OR^9)$, $N_3$, $NO_2$, $NR^8R^9$, $N(OH)R^8$, $C(O)R^8$, $C(S)R^8$, $CO_2R^8$, $C(O)SR^8$, $C(O)NR^8R^9$, $C(S)NR^8R^9$, $C(O)N(OH)R^9$, $C(S)N(OH)R^8$, $NR^8C(O)R^9$, $NR^8C(S)R^9$, $N(OH)C(O)R^9$, $N(OH)C(S)R^8$, $NR^8CO_2R^9$, $NR^8C(O)NR^9R^{10}$, $NR^8C(S)NR^9R^{10}$, $N(OH)CO_2R^8$, $NR^8C(O)SR^9$, $N(OH)C(O)NR^8R^9$, $N(OH)C(S)NR^8R^9$, $NR^8C(O)N(OH)R^9$, $NR^8C(S)N(OH)R^9$, $NR^8SO_2R^9$, $NHSO_2NR^8R^9$, $NR^8SO_2NHR^9$, and $P(O)(OR^8)(OR^9)$, with t being an integer between 1 and 2, and $R^8$ $R^9$ and $R^{10}$ being each independently selected from the group consisting of hydrogen, hydroxyl, alkyl, aryl, $Het^1$, $Het^1$alkyl, $Het^1$aryl, alkenyl, alkynyl, amino alkyl, amino aryl, alkylcarbonylamino, arylcarbonylamino, alkyithiocarbonylamino and arylthiocarbonylamino, wherein $R^2$ and $R^3$ are hydroxyl; wherein $R^4$ replaced by a double bond between the N atom and the C carbon atom of the N-containing heterocyclic ring of formula Ib; and wherein $R^5$ is hydrogen.

24. A pharmaceutical composition comprising a pharmaceutically acceptable excipient and a therapeutically effective amount of a compound according to any one of claims 1, 17 and 21.

25. A pharmaceutical composition comprising a pharmaceutically acceptable excipient and a therapeutically effective amount of a compound according to claim 9.

26. A pharmaceutical composition comprising a pharmaceutically acceptable excipient and a therapeutically effective amount of a compound according to claim 11.

27. A method of treating cancer comprising administering a compound according to any one of claims 1, 17, and 21 to an individual in need of such treatment, wherein the cancer is selected from the group consisting of lung cancer, breast cancer, melanoma cancer, glioma, colon cancer, bladder cancer, and prostate cancer.

28. A method of treating cancer comprising administrating to an individual in need of such treatment a pharmaceutical composition according to claim 24, wherein the cancer is selected from the group consisting of lung cancer, breast cancer, melanoma cancer, glioma, colon cancer, bladder cancer, and prostate cancer.

* * * * *

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

Figure 11:
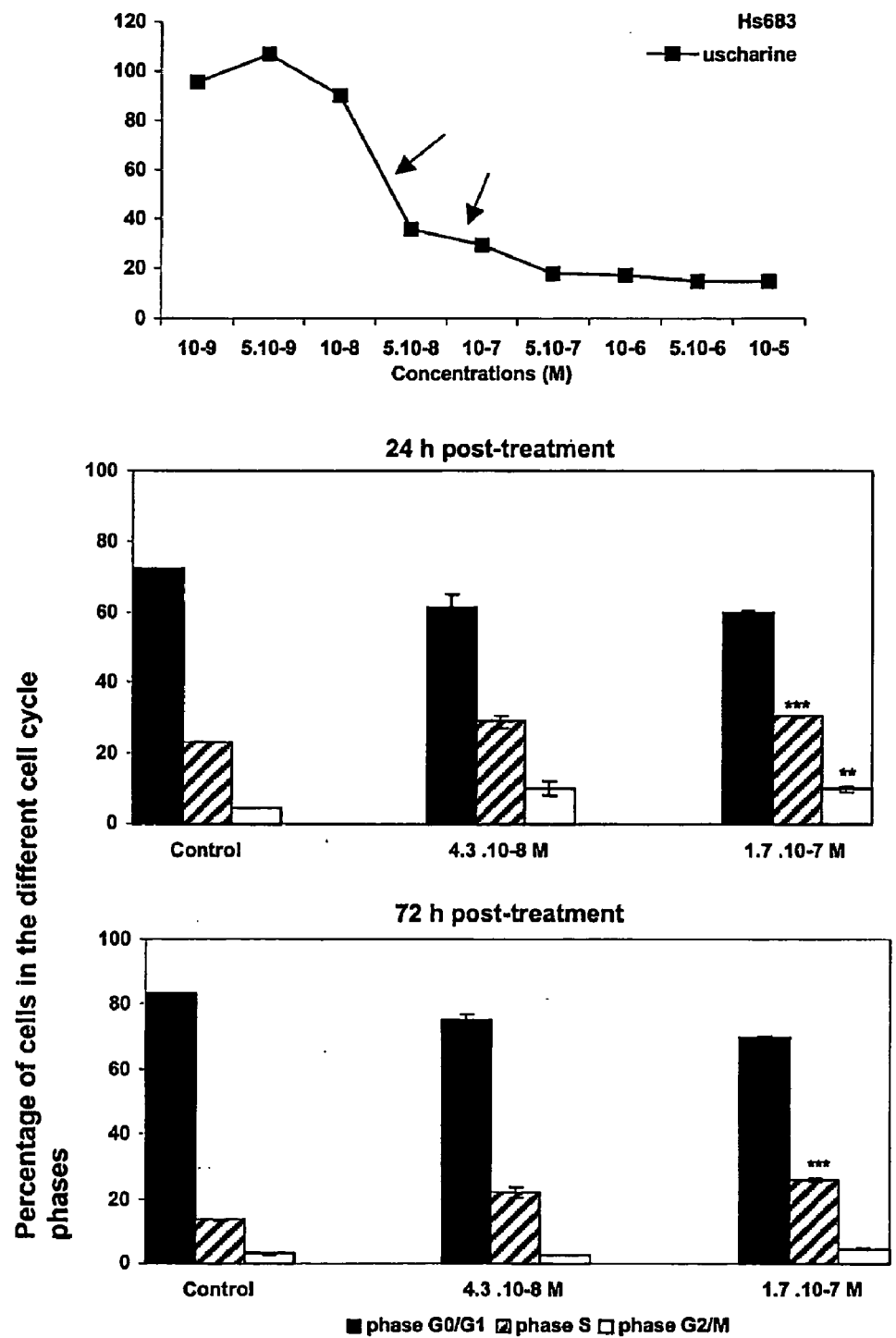
FIGS. 11 and 12 represent the effects of the compound uscharin and 2″ oxo-voruscharin, respectively on the cell cycle kinetics of Hs683 human cancer cells.
Figure 12:
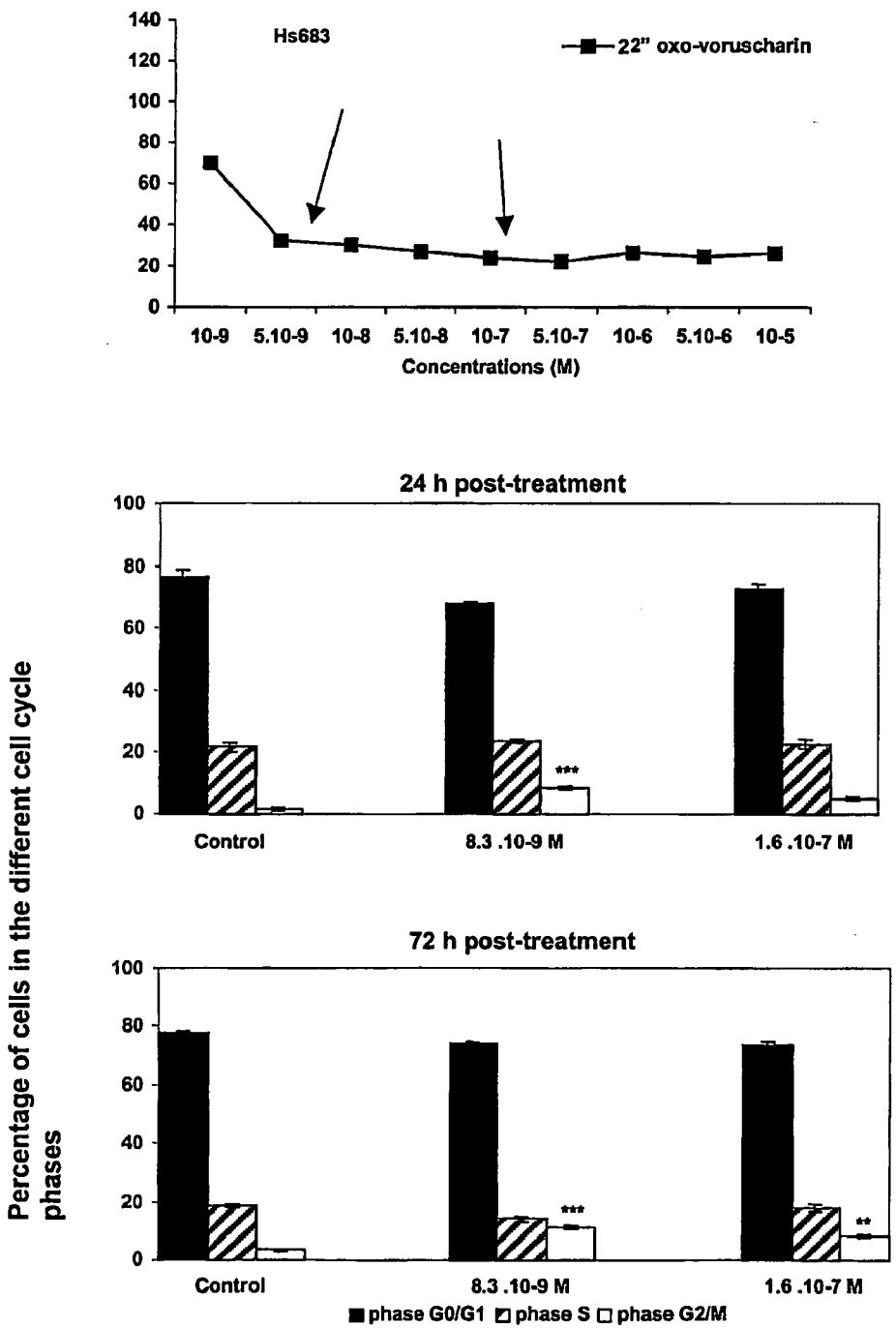

It is certified that error appears in the above-identified patent and that said Letters Patent is hereby corrected as shown below:

Sheet 5, Fig. 11, Line 2, "uscharine" should be changed to --uscharin--

Sheet 6, Fig. 12, Line 1, "22" oxo-voruscharin" should be changed to --2" oxo-voruscharin--

Sheet 8, Fig. 14, Line 1, "22" oxo-voruscharin" should be changed to --2" oxo-voruscharin--

Figure 16:
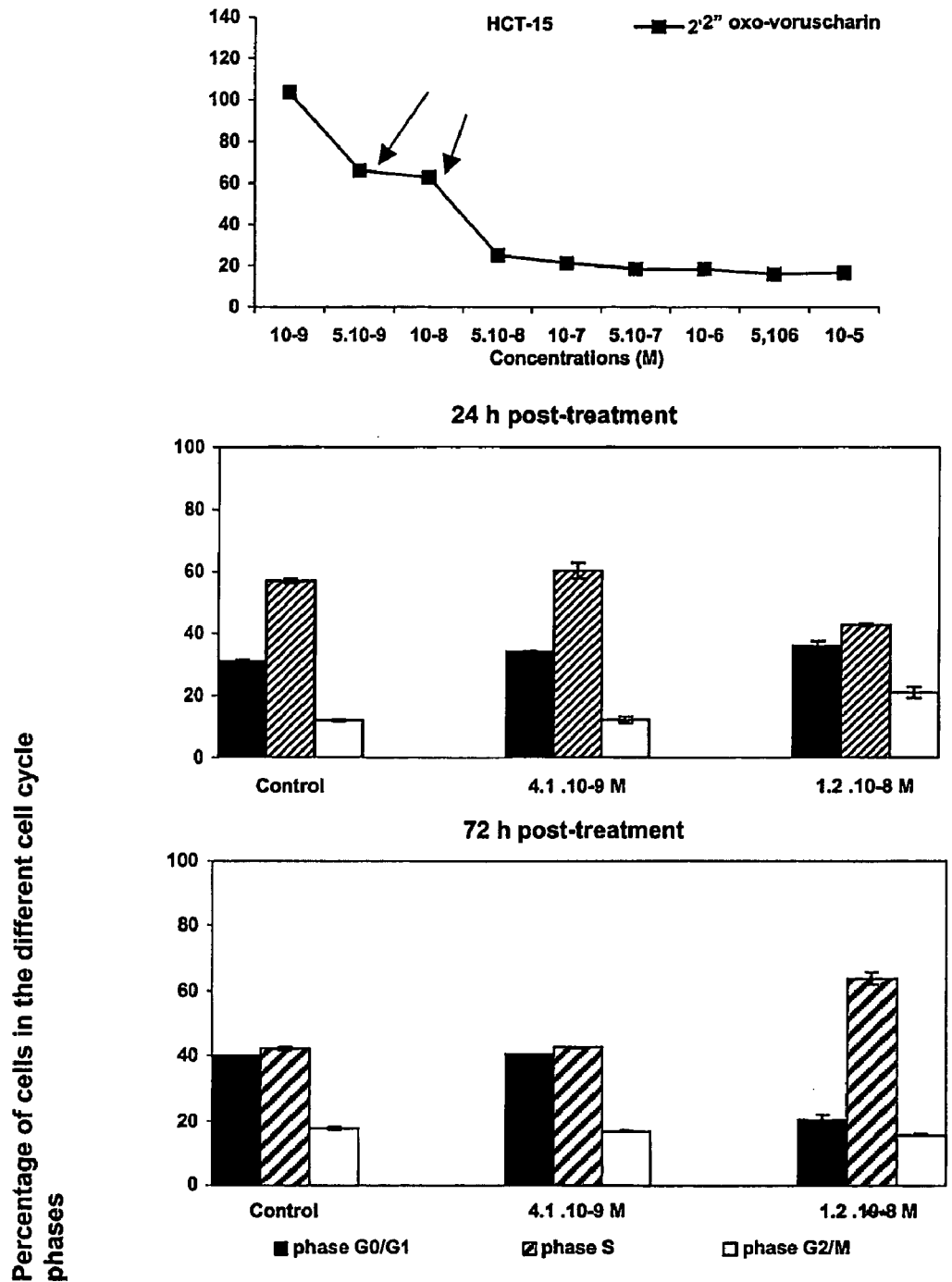

Sheet 10, Fig. 16, Line 1, "2'2" oxo-voruscharin" should be changed to --2" oxo-voruscharin--

Sheet 10, Fig. 16, Line 9, "5,106" should be changed to --5.10-6--

Column 2, Line 1, "f.e. calotropin" should be changed to --i.e., calotropin--

Column 3, Lines 47-48, "aryithioalkoxy," should be changed to --arylthioalkoxy,--

Column 4, Line 7, "alklylthio," should be changed to --alkylthio,--

Column 5, Line 11, "aylaminoalkoxy," should be changed to --arylaminoalkoxy,--

Column 6, Line 60, "and Its" should be changed to --and its--

Column 6, Line 67, "the present Invention" should be changed to --the present invention--

Column 7, Line 12, "FIG. 2 to 8" should be change to --FIGS. 2 to 8--

Column 9, Line 27, "alklylthio," should be changed to --alkylthio,--

Column 9, Line 51, "aylaminoalkoxy," should be changed to --arylaminoalkoxy,--

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

It is certified that error appears in the above-identified patent and that said Letters Patent is hereby corrected as shown below:

Column 10, Line 31, "aylaminoalkoxy," should be changed to --arylaminoalkoxy,--

Column 12, Line 7, "and $R^6$ is hydrogen" should be changed to --and $R^5$ is hydrogen--

Column 13, Line 6, "$Het^1$alkyl, $Het^1$alkyl, $Het^1$oxy," should be changed to -- $Het^1$alkyl, $Het^1$oxy,--

Column 13, Line 16, "2,4dimethyl-3-aminophenyl," should be changed to

--2,4-dimethyl-3-aminophenyl,--

Column 13, Line 17, "3-methyl-4hydroxyphenyl," should be changed to

--3-methyl-4-hydroxyphenyl,--

Column 15, Lines 16-17, "3-(benzyloxyformamidol-2-naphthoyl," should be changed to --3-(benzyloxyformamido)-2-naphthoyl--

Column 15, Line 52, "4-(3-aminophenoxy-butyl," should be changed to

--4-(3-aminophenoxy)-1-butyl--

Column 15, Lines 61 and 62, "4 (2-fluorophenoxy)-butylthio," should be changed to --4-(2-fluorophenoxy)-butylthio,--

Column 16, Line 27, "by a Het as" should be changed to --by a $Het^2$ as--

Column 16, Line 28, "3 (4-thiazolyl)-propylthio," should be changed to

--3-(4-thiazolyl)-propylthio,--

Column 16, Line 33, "3-(2-furanyl)-propylamino," should be changed to

--3-(2-furanyl)-propylamino--

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

It is certified that error appears in the above-identified patent and that said Letters Patent is hereby corrected as shown below:

Column 19, Line 9, "an wherein" should be changed to --and wherein--

Column 23, Line 51, "terms "Compounds of the" should be changed to --terms "compounds of the--

Column 24, Line 56, "such a sarginine," should be changed to --such as arginine,--

Column 25, Line 11, "according to the invenbon" should be changed to --according to the invention--

Column 26, Line 56, "has-an apparent" should be changed to --has an apparent--

Column 30, Line 45, "Asclepiadacaeae family," should be changed to --Asclepiadaceae family,--

Column 40, Last Line, "H" should be changed to -- —H--

Column 42, 3$^{rd}$ Line from Bottom, "H" should be changed to -- —H--

Column 57, 5$^{th}$ Line from Top, "—CH$_2$—CH$_2$CH==CH$_2$" should be changed to -- —CH$_2$—CH$_2$—CH==CH$_2$--

Column 74, Line 29, "of porosity no" should be changed to --of porosity n°--

Column 74, Line 34, "porosity no 3." should be changed to --porosity n° 3.--

Column 74, Line 66, "mixture was fitrated" should be changed to --mixture was filtrated--

Column 74, Line 67, "porosity no 3." should be changed to --porosity n° 3.--

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

It is certified that error appears in the above-identified patent and that said Letters Patent is hereby corrected as shown below:

Column 76, Scheme.1, First Line, "BF3·OEt2, THF, 0° C., 15''" should be changed to --$BF_3$·$OEt_2$, THF, 0° C., 15"--

Column 77, Line 3, "$BF_3$.$Et_2O$" should be changed to --$BF_3$·$Et_2O$--

Column 78, Line 58, "on FIG. 2 to 8" should be changed to --on FIGS. 2 to 8--

Column 79, Line 9, Table D, "Compound C   $5 \times 10^{-8}$-$10^{-8}$" should be changed to --Compound C   $5 \times 10^{-6}$-$10^{-6}$--

Column 79, Line 10, Table D, "Compound D   $5 \times 10^{-9}$-$10^{-9}$   $5 \times 10^{-6}$-$10^{-6}$" should be changed to --Compound D   $5 \times 10^{-9}$-$10^{-9}$   $5 \times 10^{-8}$-$10^{-8}$--

Column 82, Line 19, "in vivo ant-" should be changed to --in vivo anti- --

Column 82, Line 36, "sub-cutaneous model:" should be changed to --subcutaneous model:--

Column 82, Line 41, "is a hormono-" should be changed to --is a hormone- --

Column 83, Line 66, "A549 lung cancer," should be changed to --A549 lung cancer--

Column 84, Line 34, "cycloalkyithiocarbonyl," should be changed to --cycloalkylthiocarbonyl,--

Column 85, Lines 3-4, "amino alkyl," should be changed to --aminoalkyl,--

Column 85, Line 42, "$NR^{8R9}$," should be changed to --$NR^8R^9$,--

Column 85, Line 44, "$C(S)NR^6R^9$," should be changed to --$C(S)NR^8R^9$,--

Column 85, Line 49, "$NR^8SO_2NHR^9$," should be changed to --$NR^8SO_2R^9$,--

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

It is certified that error appears in the above-identified patent and that said Letters Patent is hereby corrected as shown below:

Column 85, Line 55, "amino aryl," should be changed to --aminoaryl,--

Column 85, Line 59, "alklylthio," should be changed to --alkylthio,--

Column 86, Line 26, "$SO_2NR^{11R12}$," should be changed to --$SO_2NR^{11}R^{12}$,--

Column 86, Line 35, "$MHSO_2NR^{11}R^{12}$," should be changed to --$NHSO_2NR^{11}R^{12}$,--

Column 86, Line 47, "halo alkyl," should be changed to --haloalkyl,--

Column 86, Line 54, "amino alkanoyl," should be changed to --aminoalkanoyl,--

Column 86, Line 55, "amino alkyl," should be changed to --aminoalkyl,--

Column 86, Line 66, "aylaminoalkoxy," should be changed to --arylaminoalkoxy,--

Column 87, Line 65, "amionalkyl" should be changed to --aminoalkyl--

Column 88, Line 23, "cycloalkyithiocarbonyl," should be changed to

--cycloalkylthiocarbonyl,--

Column 88, Line 47, "$Het^2$aryloxycarbonyl $Het^2$aroyl," should be changed to

--$Het^2$aryloxycarbonyl, $Het^2$aroyl,--

Column 88, Line 52, "amino alkanoyl," should be changed to --aminoalkanoyl,--

Column 88, Lines 55-56, "amino alkyl," should be changed to --aminoalkyl,--

Column 88, Line 56, "amino aryl," should be changed to --aminoaryl,--

Column 88, Line 64, "halo alkyloxy," should be changed to --haloalkyloxy,--

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

It is certified that error appears in the above-identified patent and that said Letters Patent is hereby corrected as shown below:

Column 89, Line 41, "amino alkyl," should be changed to --aminoalkyl,--

Column 89, Line 42, "amino aryl," should be changed to --aminoaryl,--

Column 89, Line 43, "alkyithiocarbonylamino," should be changed to

--alkylthiocarbonylamino,--

Column 90, Line 4, "and $R^7$ independently" should be changed to --and $R^7$ being independently--

Column 92, Line 6, "amino alkyl," should be changed to --aminoalkyl,--

Column 92, Line 7, "amino aryl," should be changed to --aminoaryl,--

Column 92, Line 30, "alkyithiocarbonylamino," should be changed to

--alkylthiocarbonylamino,--

Column 93, Line 1, "amino alkyl," should be changed to --aminoalkyl,--

Column 93, Line 3, "alkyithiocarbonylamino" should be changed to

--alkylthiocarbonylamino--

Column 93, Line 42, "amino alkyl," should be changed to --aminoalkyl,--

Column 93, Line 44, "alkyithiocarbonylamino" should be changed to

--alkylthiocarbonylamino--

Column 94, Line 5, "$C(O)N(OH)R^8$," should be changed to --$C(O)N(OH)R^9$,--

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

It is certified that error appears in the above-identified patent and that said Letters Patent is hereby corrected as shown below:

Column 94, Line 15, "amino alkyl," should be changed to --aminoalkyl,--

Column 94, Line 16, "amino aryl," should be changed to --aminoaryl,--

Column 94, Line 26, "and $R^3$ are hydroxyl" should be changed to --and $R^3$ are hydroxyl,--

Column 95, Line 6, "$SO_2R^8CR^8$==$N(OR^9)$," should be changed to --$SO_2R^8$, $CR^8$==$N(OR^9)$,--

Column 96, Line 4, "alkyithiocarbonylamino" should be changed to --alkylthiocarbonylamino--

Column 96, Line 50, "alkyithiocarbonylamino" should be changed to --alkylthiocarbonylamino--

Column 97, Lines 54-55, "$Het^1$alkyloxy, Het oxy, Het oxyalkyloxy," should be changed to --$Het^1$alkyloxy, $Het^1$oxy, $Het^1$oxyalkyloxy,--

Column 97, Line 59, "$Het^2$alkyloxy; Hetoxyalkyloxy," should be changed to --$Het^2$alkyloxy, $Het^2$oxyalkyloxy,--

Column 98, Line 31, "alkyithiocarbonylamino" should be changed to --alkylthiocarbonylamino--

Column 99, Line 1, "and amionalkyl" should be changed to --and aminoalkyl--

Column 99, Line 21, "amino alkyl," should be changed to --aminoalkyl,--

Column 99, Line 29, "halo alkyloxy," should be changed to --aminoalkyloxy,--

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

It is certified that error appears in the above-identified patent and that said Letters Patent is hereby corrected as shown below:

Column 100, Line 4, "amino alkyl," should be changed to --aminoalkyl,--

Column 100, Line 45, "amino aryl," should be changed to --aminoaryl,--

Column 100, Line 46, "alkyithiocarbonylamino" should be changed to

--alkylthiocarbonylamino--

Column 101, Line 10, "$NR^8C(S)N(OH)R^9$," should be changed to

--$NR^8C(O)N(OH)R^9$,--

Column 101, Line 16, "amino alkyl," should be changed to --aminoalkyl,--

Column 101, Line 18, "alkyithiocarbonylamino" should be changed to

--alkylthiocarbonylamino--

Column 102, Line 1, "amino aryl," should be changed to --aminoaryl,--

Column 102, Line 35, "amino alkyl," should be changed to --aminoalkyl,--

Column 103, Line 10, "and amionalkyl" should be changed to --and aminoalkyl--

Column 103, Line 48, "amino aryl," should be changed to --aminoaryl,--

UNITED STATES PATENT AND TRADEMARK OFFICE
CERTIFICATE OF CORRECTION

PATENT NO. : 7,320,971 B2
APPLICATION NO. : 10/530904
DATED : January 22, 2008
INVENTOR(S) : Van Quaquebeke et al.

It is certified that error appears in the above-identified patent and that said Letters Patent is hereby corrected as shown below:

Column 104, Line 28, "amino alkyl," should be changed to --aminoalkyl,--

Column 104, Line 29, "amino aryl," should be changed to --aminoaryl,--

Column 104, Line 30, "alkyithiocarbonylamino" should be changed to

--alkylthiocarbonylamino--

Column 104, Line 31, "wherein $R^4$" should be changed to --wherein $R^4$ is--

Signed and Sealed this

Fifteenth Day of July, 2008

JON W. DUDAS
*Director of the United States Patent and Trademark Office*